(12) United States Patent
Schroeder et al.

(10) Patent No.: US 7,314,046 B2
(45) Date of Patent: Jan. 1, 2008

(54) APPARATUS AND METHOD FOR RESPIRATORY TRACT THERAPY

(75) Inventors: Gary Schroeder, Londonderry, NH (US); Dirk Ten Broeck, Nashua, NH (US); Owen S. Bamford, Linthicum Heights, MD (US); William F. Niland, Arnold, MD (US); Felino V. Cortez, Jr., Bowie, MD (US)

(73) Assignee: Vapotherm, Inc., Stevensville, MD (US)

( * ) Notice: Subject to any disclaimer, the term of this patent is extended or adjusted under 35 U.S.C. 154(b) by 724 days.

(21) Appl. No.: 10/149,356

(22) PCT Filed: Dec. 8, 2000

(86) PCT No.: PCT/US00/33346

§ 371 (c)(1),
(2), (4) Date: Jan. 29, 2003

(87) PCT Pub. No.: WO01/41854

PCT Pub. Date: Jun. 14, 2001

(65) Prior Publication Data

US 2003/0209246 A1 Nov. 13, 2003

(51) Int. Cl.
*A61M 16/00* (2006.01)
*A61M 15/00* (2006.01)

(52) U.S. Cl. ............................ 128/200.14; 128/203.16

(58) Field of Classification Search ........... 128/200.14, 128/203.16, 203.17, 203.24, 203.26, 203.27, 128/911, 912, 204.14, 204.17, 200.24, 206.11, 128/207.18, 204.18, 204.24, 205.18
See application file for complete search history.

(56) References Cited

U.S. PATENT DOCUMENTS

| 3,491,754 A | | 1/1970 | Weese |
| 3,616,796 A | * | 11/1971 | Jackson ................. 128/203.27 |
| 3,864,440 A | | 2/1975 | Glocoechea |
| 3,871,373 A | | 3/1975 | Jackson ...................... 128/193 |
| 3,912,795 A | * | 10/1975 | Jackson ..................... 261/36.1 |
| 3,923,057 A | | 12/1975 | Chalon |

(Continued)

FOREIGN PATENT DOCUMENTS

EP 0 009 543 A1 4/1980

(Continued)

OTHER PUBLICATIONS

Abstract—Effect of Vapothermr, A High-Flow Humidified O2 Delivery Device, On Breathing in COPD Patterns During Exercise, Nugent T. Vance, G. Criner GJ, Chatlia W. Div Pulm & Crit Care, Temple School of Medicine, Phila., Pa, (Reprinted from American Journal of Respiratory and Critical Care Medicine vol. 165, No. 8, Part 2, Apr. 2002, p. A592.

(Continued)

*Primary Examiner*—Teena Mitchell
(74) *Attorney, Agent, or Firm*—RatnerPrestia

(57) ABSTRACT

An apparatus is provided for delivering heated and humidified air to the respiratory tract of a human patient for respiratory tract therapy and treatment. The apparatus includes a supply unit (11) and a delivery tube (28) that can be releasably connected to the supply unit (11). Methods of respiratory tract therapy and treatment are also provided.

24 Claims, 40 Drawing Sheets

U.S. PATENT DOCUMENTS

| | | | |
|---|---|---|---|
| 3,944,635 A | | 3/1976 | Siegenthaler |
| 4,026,285 A | | 5/1977 | Jackson |
| 4,110,419 A | | 8/1978 | Miller |
| 4,134,940 A | | 1/1979 | Sherman |
| 4,137,940 A | * | 2/1979 | Faisandier ................... 137/486 |
| 4,201,204 A | * | 5/1980 | Rinne et al. ............ 128/203.27 |
| 4,204,535 A | | 5/1980 | Pohlmann |
| 4,232,667 A | | 11/1980 | Chalon et al. |
| 4,249,527 A | | 2/1981 | Ko et al. |
| 4,324,238 A | | 4/1982 | Genese et al. ............... 128/214 |
| 4,328,793 A | | 5/1982 | Martin |
| 4,338,267 A | | 7/1982 | Riuli et al. |
| 4,350,647 A | | 9/1982 | de la Cruz |
| 4,372,306 A | | 2/1983 | Genese et al. ............... 128/214 |
| 4,381,267 A | * | 4/1983 | Jackson ....................... 261/104 |
| 4,401,114 A | | 8/1983 | Lwoff et al. |
| 4,463,755 A | | 8/1984 | Suzuki |
| 4,481,944 A | | 11/1984 | Bunnell |
| 4,621,633 A | | 11/1986 | Bowles et al. |
| 4,632,677 A | | 12/1986 | Blackmer ..................... 55/158 |
| 4,682,010 A | | 7/1987 | Drapeau et al. |
| 4,686,354 A | | 8/1987 | Makin |
| 4,708,831 A | * | 11/1987 | Elsworth et al. ............ 261/130 |
| 4,722,334 A | | 2/1988 | Blackmer et al. ...... 128/203.16 |
| 4,773,410 A | | 9/1988 | Blackmer et al. ...... 128/203.26 |
| 4,801,385 A | | 1/1989 | Sachtler et al. |
| 4,829,998 A | | 5/1989 | Jackson |
| 4,886,055 A | | 12/1989 | Hoppough |
| 4,911,157 A | | 3/1990 | Miller |
| 4,953,546 A | | 9/1990 | Blackmer et al. ...... 128/203.16 |
| 4,955,372 A | | 9/1990 | Blackmer et al. ...... 128/203.16 |
| 4,967,744 A | | 11/1990 | Chua |
| 5,062,145 A | * | 10/1991 | Zwaan et al. ............... 392/396 |
| 5,063,994 A | | 11/1991 | Verkaart ..................... 165/154 |
| 5,097,898 A | | 3/1992 | Verkaart ..................... 165/154 |
| 5,101,820 A | | 4/1992 | Christopher |
| 5,218,833 A | | 6/1993 | Newbold |
| 5,236,586 A | | 8/1993 | Antoni et al. |
| 5,255,674 A | | 10/1993 | Oftedal et al. |
| 5,348,691 A | | 9/1994 | McElroy et al. |
| 5,349,946 A | | 9/1994 | McComb |
| 5,396,884 A | | 3/1995 | Bagwell et al. |
| 5,738,808 A | | 4/1998 | Iwamoto |
| 5,769,071 A | * | 6/1998 | Turnbull ................. 128/203.12 |
| 5,890,490 A | | 4/1999 | Aylsworth et al. |
| 6,050,260 A | | 4/2000 | Daniell et al. |
| 6,332,462 B1 | | 12/2001 | Krohn |
| 6,367,472 B1 | | 4/2002 | Koch |
| 6,457,472 B1 | | 10/2002 | Schwartz et al. |
| 6,653,012 B2 | | 11/2003 | Suzuki et al. |
| 6,739,338 B2 | | 5/2004 | Tanhehco et al. |
| 6,786,475 B2 | | 9/2004 | Salter et al. |
| 6,877,510 B2 | * | 4/2005 | Nitta ...................... 128/203.17 |
| 6,904,911 B2 | * | 6/2005 | Gibertoni ............... 128/201.13 |
| 6,976,489 B2 | * | 12/2005 | Mantell et al. ......... 128/204.17 |
| 6,988,497 B2 | * | 1/2006 | Levine .................. 128/203.27 |
| 2002/0195104 A1 | * | 12/2002 | Fini et al. .............. 128/203.17 |
| 2003/0209246 A1 | | 11/2003 | Schroeder et al. |
| 2005/0121038 A1 | | 6/2005 | Christopher |
| 2005/0178383 A1 | | 8/2005 | Mackie et al. |

FOREIGN PATENT DOCUMENTS

| | | |
|---|---|---|
| EP | 0 062 913 A1 | 10/1982 |
| EP | 0 359 531 A2 | 3/1990 |
| FR | 2 164 873 | 8/1973 |
| FR | 2 311 558 | 12/1976 |
| WO | 86/02276 | 4/1986 |

OTHER PUBLICATIONS

International Search Report for PCT/US/00/33346, search date May 29, 2001.

International Search Report for PCT/US05/09556, search date Jul. 6, 2005.

* cited by examiner

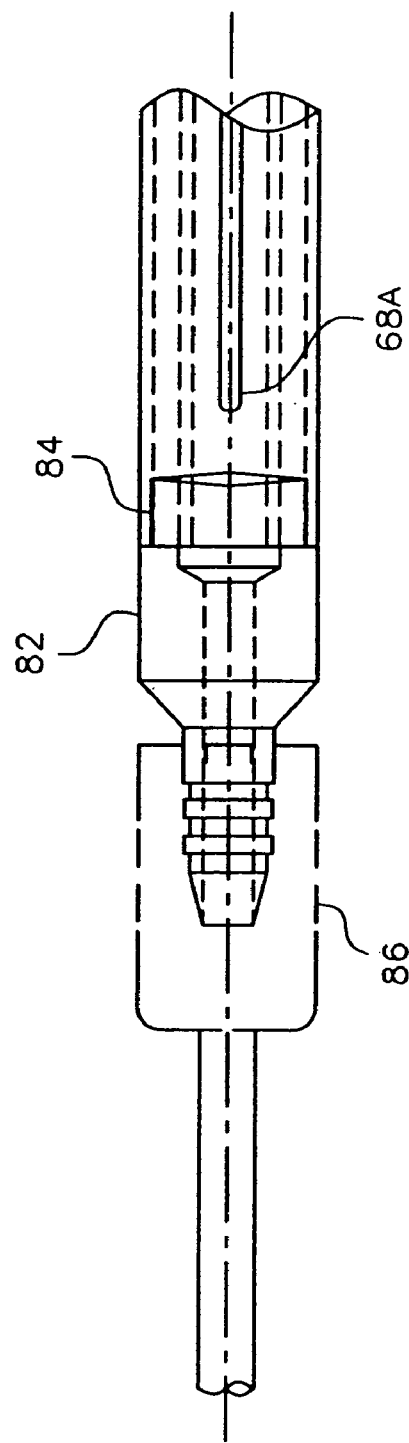

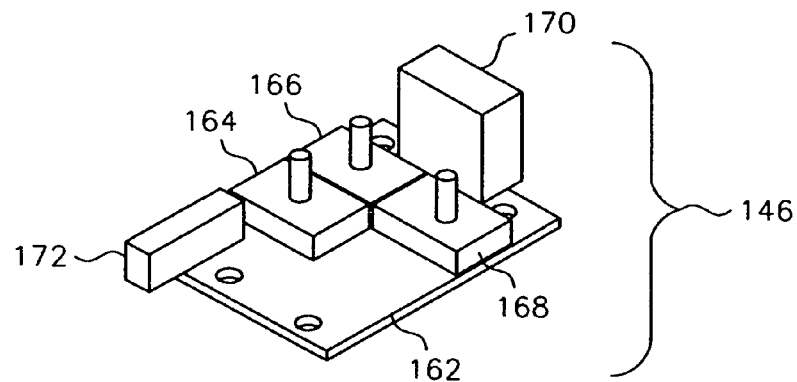
FIG. 12
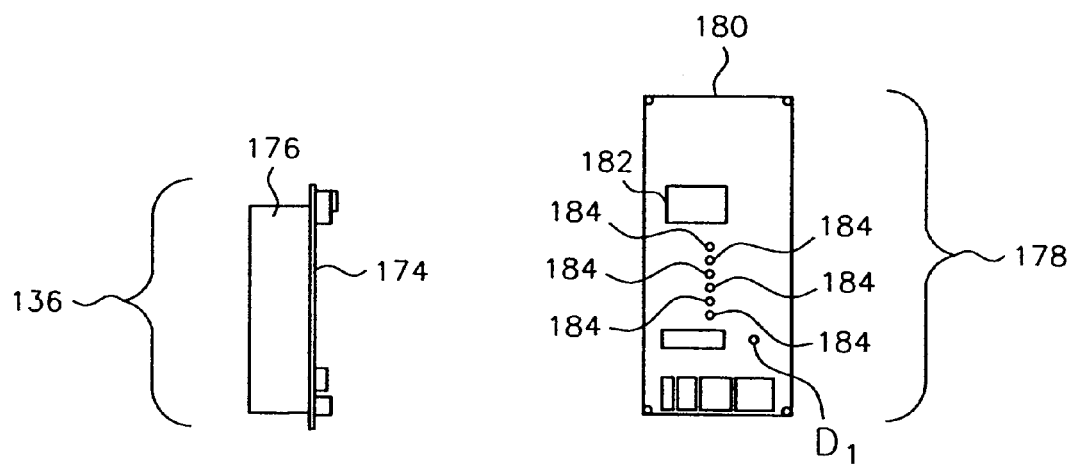
FIG. 13     FIG. 14

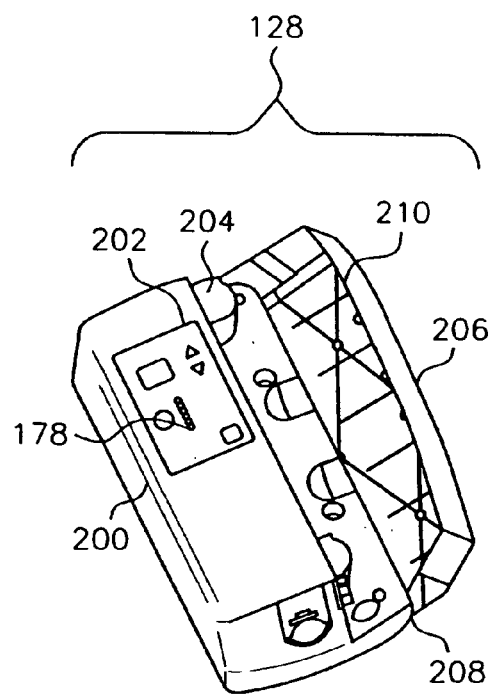
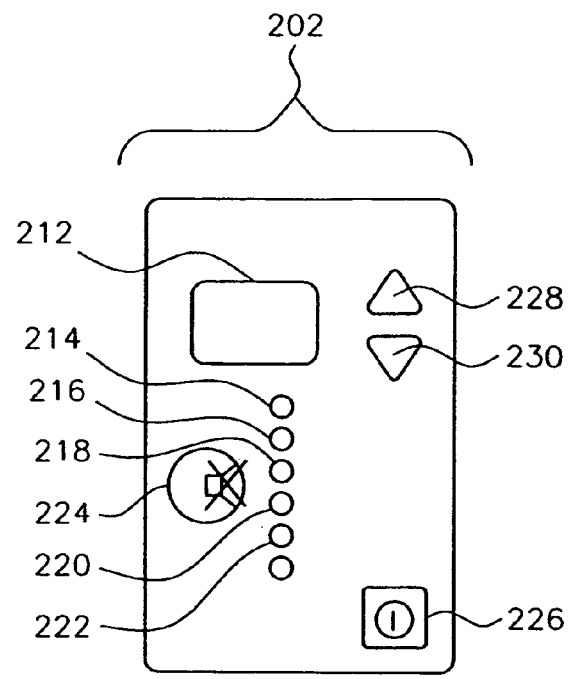
FIG. 18
FIG. 19
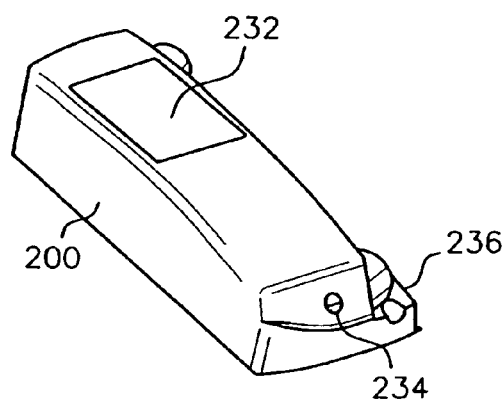
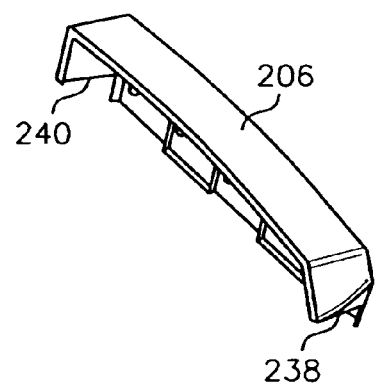
FIG. 20
FIG. 21

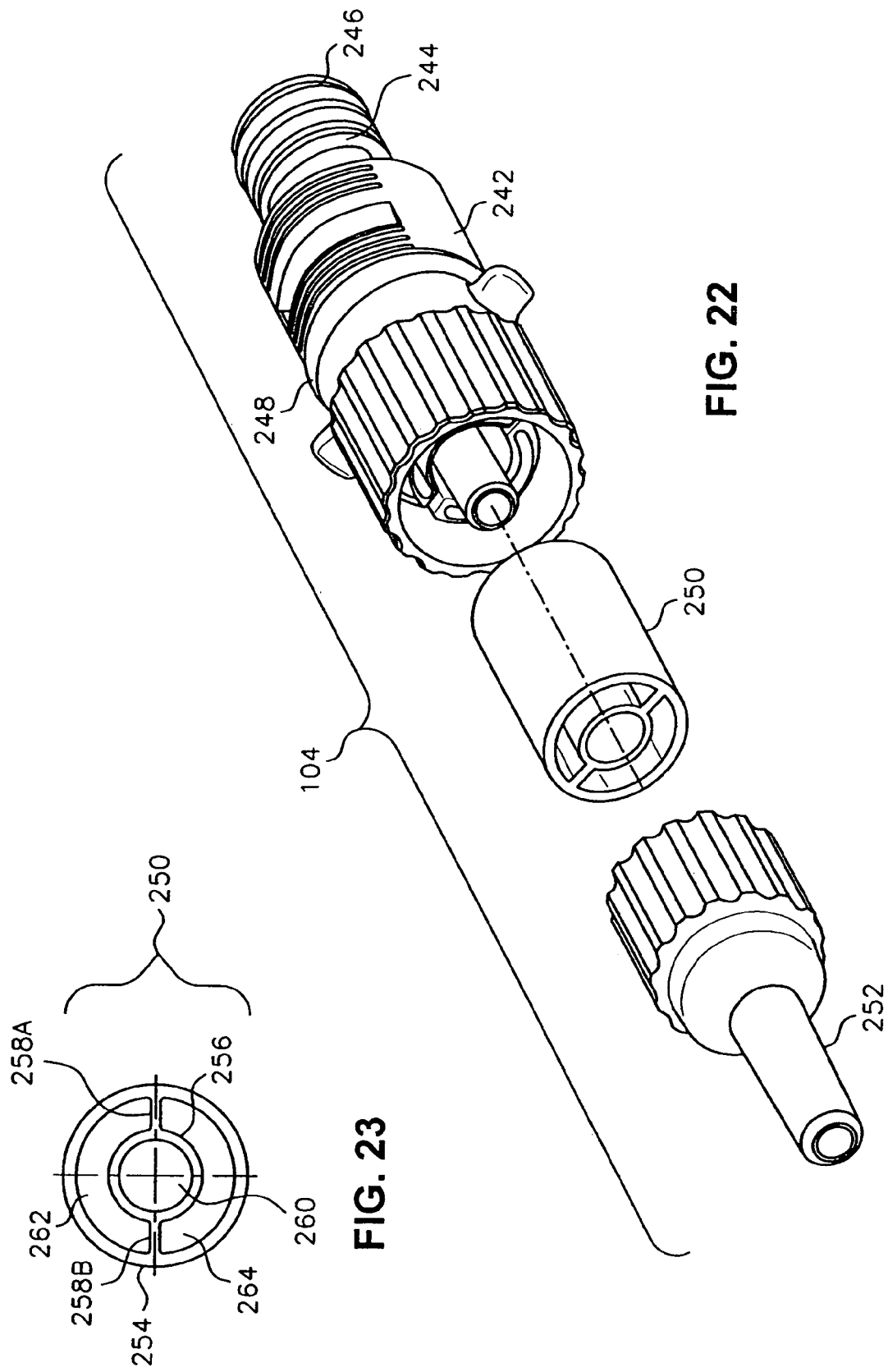

APPARATUS AND METHOD FOR RESPIRATORY TRACT THERAPY

FIELD OF THE INVENTION

This invention relates to an apparatus and method for respiratory tract therapy. More particularly, this invention relates to an apparatus adapted to heat and humidify air and to deliver heated and humidified air to the respiratory tract of a human patient. This invention also relates to methods for respiratory tract therapy.

BACKGROUND OF THE INVENTION

It has been recognized that the delivery of oxygen and oxygen-enriched air to the respiratory tract of a patient often results in discomfort to the patient, especially when the air is delivered over an extended period of time. It has also been recognized that the delivery of air having relatively low absolute humidity can result in respiratory irritation.

Several devices have been proposed to overcome these problems. U.S. Pat. No. 4,632,677, issued to Richard H. Blackmer, the disclosure of which is incorporated herein by reference, describes an oxygen-enriching apparatus including means for increasing or regulating the humidity of the air. The Blackmer apparatus employs an array of membrane cells, a vacuum pump to draw a flow of humidity-and-oxygen-enriched air from each cell, low- and high-temperature condensers connected to receive air drawn from the cells, and a proportioning valve connected to the condensers for providing a desired humidity level of the air.

According to the Blackmer '677 patent, air supplied to the patient may be heated by circulation of warm air over delivery tubing, use of electric resistance heaters, and circulating warm liquid co-linearly with the delivery tubing. With regard to warm liquid heating, warm water is circulated through a tubing jacket comprised of feed and return tubes, which trace the delivery air line, by means of a motor-driven pump. A feed tube extends from the pump and a return tube connects to a water reservoir. Regarding warm air circulation, a blower delivers warmed air to a tube which co-axially surrounds the oxygen-enriched air delivery tubing. Electrical resistance heating may also be used according to the Blackmer '677 patent.

Another system is described in U.S. Pat. No. 4,773,410, issued to Richard H. Blackmer et al., the disclosure of which is incorporated herein by reference. The apparatus described by the Blackmer et al. '410 patent includes a permeable membrane to permit a liquid-vapor boundary, as well as means for delivering a substantially condensation-free saturated vapor-gas stream to a respiratory tract. In one embodiment described in the Blackmer et al. '410 patent, the apparatus uses a delivery tube with electrical heating elements that heat the air as it passes through the tube. In another embodiment, a heater heats water which is then delivered through a separate tube that is connected to the delivery tube near the delivery tube's exit port. The heated water then flows counter-current to the air flow to heat the air and exits the delivery tube near its opposite end.

Nevertheless, there remains a need for an improved apparatus for respiratory tract therapy that can be used in various settings including clinical, hospital, and home settings. There also remains a need for improved methods of respiratory tract therapy.

SUMMARY OF THE INVENTION

A tubing assembly is provided for delivering gas to a patient from a supply unit having a port defining a gas outlet, a fluid outlet, and a fluid inlet. The tubing assembly includes a tube having a gas passage to deliver gas toward a patient and a fluid passage to circulate fluid and transfer heat to gas in the gas passage. The tubing assembly also includes a fitting connected to the tube. The fitting has a gas inlet oriented to provide gas flow between the gas outlet of the supply unit and the gas passage of the tube. The fitting also includes a fluid inlet oriented to provide fluid flow between the fluid outlet of the supply unit and the fluid passage of the tube. Finally, the fitting further includes a fluid outlet oriented to provide fluid flow between the fluid passage of the tube and the fluid inlet of the supply unit. The fitting of the tubing assembly is configured to provide flow communication between the gas outlet, the fluid outlet, and the fluid inlet of the supply unit and the gas passage and the fluid passage of the tube upon insertion of the fitting of the tubing assembly into the port of the supply unit.

In combination with the tubing assembly, this invention also provides a supply unit configured to supply gas for delivery to a patient and to supply fluid for heating the gas. The supply unit includes a port defining a gas outlet, a fluid outlet, and a fluid inlet, wherein the fitting of the tubing assembly is releasably engaged in the port of the supply unit. The gas outlet of the supply unit is in flow communication with the gas inlet of the fitting of the tubing assembly. The fluid outlet of the supply unit is in flow communication with the fluid inlet of the fitting of the tubing assembly. Finally, the fluid inlet of the supply unit is in flow communication with the fluid outlet of the fitting of the tubing assembly.

According to another aspect of this invention, an apparatus is provided for removing air from a circulating liquid. The apparatus includes a chamber having an inlet for introducing circulating liquid into the chamber, an inlet for introducing supplemental liquid into the chamber, and an outlet for delivering circulating liquid and supplemental liquid from the chamber. The chamber is configured to accumulate air from circulating liquid entering the chamber through the circulating liquid inlet. The supplemental liquid inlet is positioned to discharge accumulated air from the chamber.

This invention also provides methods for treatment or therapy of the respiratory tract. For example, this invention provides a method for warming a patient comprising delivering heated and humidified oxygen to the nasal passageway of the patient through a nasal cannula. This invention also provides methods for enhancing athletic performance, reducing the work of breathing, weaning a patient from mechanical ventilation, for treating asthma patients, and for improving vocal function, for example.

BRIEF DESCRIPTION OF THE DRAWINGS

Aspects of the present invention will now be described by non-limiting example with reference to the following drawings, of which:

FIG. 7 is a side view of an end portion of the delivery tube assembly illustrated in FIGS. 4A and 4B.

FIG. 12 is a front perspective view of a sensor printed circuit board assembly adapted for use in the back plate assembly illustrated in FIG. 11A.

FIG. 13 is a side view of a power printed circuit board adapted for use in the back plate assembly illustrated in FIG. 11A.

FIG. 14 is a front view of a display printed circuit board adapted for use in the back plate assembly illustrated in FIG. 11A.

FIG. 18 is a perspective view of a cover assembly adapted for use in the supply unit illustrated in FIG. 10.

FIG. 19 is an embodiment of a display adapted for use with the cover assembly illustrated in FIG. 18.

FIG. 20 is a perspective view of a main housing component of the cover assembly illustrated in FIG. 18.

FIG. 21 is a perspective view of an embodiment of a housing door component of the cover assembly illustrated in FIG. 18.

FIG. 22 is a perspective view of an embodiment of a delivery tube assembly of the apparatus illustrated in FIG. 9.

FIG. 23 is an end view of an embodiment of a tube adapted for use in the delivery tube assembly illustrated in FIG. 22.

DETAILED DESCRIPTION OF THE INVENTION

Figure 1:
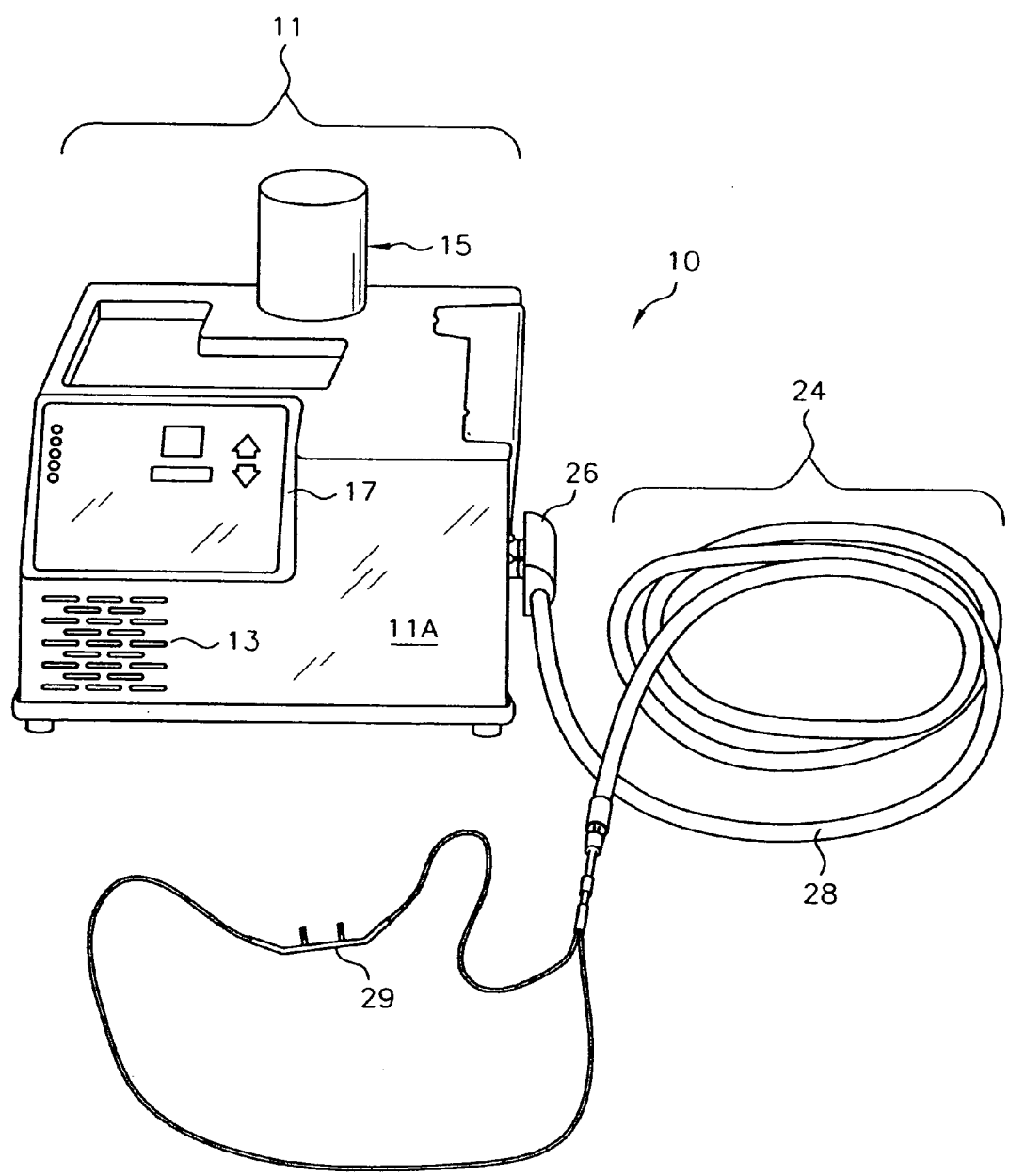
FIG. 1 is a perspective view of an embodiment of an apparatus according to aspects of this invention.

Aspects of this invention will now be described with reference to specific examples and embodiments selected for illustration in the figures. It will be appreciated that the spirit and scope of this invention is not limited to the selected examples and embodiments, and that the scope of this invention is defined separately in the appended claims. It will also be appreciated that the figures are not drawn to any particular proportion or scale, and that many variations can be made to the illustrated embodiments without departing from the spirit of this invention.

Referring to the figures in general, according to one aspect of this invention an elongated member such as a delivery tube 28 is provided for delivering fluid from a fluid inlet such as an air inlet opening 58 at a proximal end portion of the elongated member to a fluid outlet such as a tubing connector 82 at a distal end portion of the elongated member for receipt by a patient (not shown). The elongated member is adapted to heat the fluid as it is delivered to the patient.

The elongated member includes a delivery lumen such as an air lumen 72 defined by the elongated member from the fluid inlet at the proximal end portion to the fluid outlet at the distal end portion. The delivery lumen is configured for the flow of the fluid distally from the fluid inlet toward the fluid outlet. The elongated member also includes a heating fluid inlet such as a water inlet opening 60 defined by the elongated member at the proximal end portion as well as a heating supply lumen such as a heating fluid lumen 74 defined by the elongated member adjacent to the delivery lumen from the heating fluid inlet to the distal end portion. Also included as a part of the elongated member is a heating fluid outlet such as a water outlet opening 62 defined by the elongated member at the proximal end portion as well as a heating return lumen such as a return lumen 76 defined by the elongated member adjacent to the delivery lumen from the distal end portion to the heating fluid outlet. The is heating supply lumen and the heating return lumen are connected to one another (adjacent to tubing connector 82, for example) for flow therebetween at the distal end portion.

The heating supply lumen and the heating return lumen of the elongated member are configured for the flow of the heating fluid distally from the heating fluid inlet toward the distal end portion through the heating supply lumen, and for flow of the heating fluid proximally from the distal end portion toward the heating fluid outlet through the heating return lumen. Heat is thereby transferred from the heating fluid to the fluid in the delivery lumen as it is delivered to the patient.

According to another aspect of this invention, an apparatus such as a supply unit 11 is provided for respiratory tract therapy. The apparatus includes a housing such as housing 11A that is configured to receive air and water. A humidified air outlet such as an air outlet port or connector 40 is defined in the housing for delivering humidified air from the apparatus. A water supply outlet such as a water outlet port or connector 42 is defined in the housing for delivering heated water from the apparatus. Finally, a water return inlet such as a water inlet port or connector 44 is defined in the housing for returning heated water to the apparatus.

The humidified air outlet, the water supply outlet, and the water supply inlet of the apparatus are positioned proximal to one another for releasable connection to an elongated member such as delivery tube 28 that is configured for delivering the humidified air from the housing toward the respiratory tract of a patient. The elongated member is also configured for circulating heated water from the water supply outlet to the water return inlet to transfer heat from the heated water to the humidified air as it is delivered to the patient.

According to yet another aspect of this invention, an apparatus such as a system 100 is provided with a supply unit such as supply unit 102 having an air inlet 152 configured for releasable connection to a source of pressurized air. The apparatus is also provided with a port such as port 130 providing a humidified air outlet for delivering humidified air from the supply unit, a fluid supply outlet for delivering heated fluid from the supply unit, and a fluid return inlet for returning heated fluid to the supply unit.

An elongated member such as delivery tube assembly 104 is releasably connected to the supply unit. The elongated member defines a delivery lumen such as air lumen 260 configured to deliver humidified air toward a patient. The elongated member also defines a fluid supply lumen such as heating fluid lumen 262 (or 264) and a fluid return lumen such as return lumen 264 (or 262), each extending adjacent to the delivery lumen. The fluid supply and fluid return lumens are configured to circulate the heated fluid between the fluid supply outlet of the supply unit and the fluid return inlet of the supply unit to transfer heat from the heated fluid to the humidified air as it is delivered to the patient.

An apparatus according to this invention will now be described with reference to the specific embodiment selected for illustration in FIG. 1. Generally speaking, the apparatus is adapted to deliver heated and humidified air to the respiratory tract of a human patient. The apparatus illustrated in FIG. 1 is compact in size and portable, so as to be adapted for use in a variety of settings and for transport between locations. The apparatus can be used in the home by a patient and at the patient's bedside, if desired. The apparatus can also be used in hospitals, clinics, and other settings, as well.

The apparatus includes a supply unit that provides a source for heating fluid such as heated water as well as a source of humidified air. The heating fluid provided by the supply unit is used to heat the humidified air as the humidified air is delivered from the supply unit to the patient's respiratory tract.

The apparatus also includes a delivery tube assembly that is releasably attached to the supply unit. The delivery tube assembly is designed so that it can be used by a particular patient and then discarded after one or a number of uses. The delivery tube assembly provides a passageway for the flow of humidified air to the patient's respiratory tract. The delivery tube assembly also provides passageways for the flow and return of heating fluid in such a way as to promote heat transfer from the heating fluid to the humidified air as it is delivered.

Throughout the descriptions of apparatus 10 and, especially, delivery tube assembly 24, reference is made to portions of the figures to define directions for flow and the position of various features. The terms "proximal" and "distal" will also be used to indicate such positions. Specifically, as used herein, the term "proximal" refers to a position toward the supply unit (away from the patient), and the term "distal" refers to a position toward the patient (away from the supply unit).

Referring now to the embodiment selected for illustration in FIG. 1, apparatus 10 includes a supply unit 11 having a substantially enclosed housing 11A that is adapted to rest on a table top or other surface or stand in a portable configuration. Supply unit 11 is provided with an air exhaust 13 defined by openings in the housing of supply unit 11. An air inlet (not shown) permits the flow of air into the interior of the housing. A water supply 15 in the form of a water container or reservoir is releasably connected in the top portion of the housing of supply unit 11 so that it can be removed and refilled to provide a supply of water to apparatus 10.

A display panel 17 on a surface of the housing of supply unit 11 permits a user to control aspects of apparatus 10 and also displays information that can be used by the patient or the patient's assistant. For example, in this embodiment of apparatus 10, display panel 17 includes "UP" and "DOWN" buttons (indicated by arrows) so that the user can adjust the air temperature. Display panel 17 also includes a temperature output display as well as a display for the minimum and maximum set temperatures. Display panel 17 also includes indicators for the maintenance of apparatus 10: an "ADD WATER" light indicates that water should be added via water supply 15; a "DELIVERY TUBE" light indicates that a delivery tube assembly 24 (described later) must be reconnected; a "CARTRIDGE" light indicates that a cartridge (to be described later) needs maintenance; a "CLEANING" light indicates that aspects of apparatus 10 should be cleaned; and a "CHANGE CARTRIDGE" light indicates that the cartridge should be changed.

The delivery tube assembly 24 is releasably connected to the housing of supply unit 11 by means of a connector block 26. The connection between supply unit 11 and delivery tube assembly 24 can be easily broken to remove assembly 24 for cleaning, for maintenance, or for disposal and replacement. Quick disconnects (described later) are provided on connector block 26 and supply unit 11 to facilitate the removal and replacement of assembly 24. A delivery tube 28 extends from connector block 26 to a nasal cannula 29 that extends from delivery tube 28 to the patient's respiratory tract during use. Nasal cannula 29 and associated fittings used for supplying air to the nares of a patient are readily available components that are well known in the art.

Figure 2:
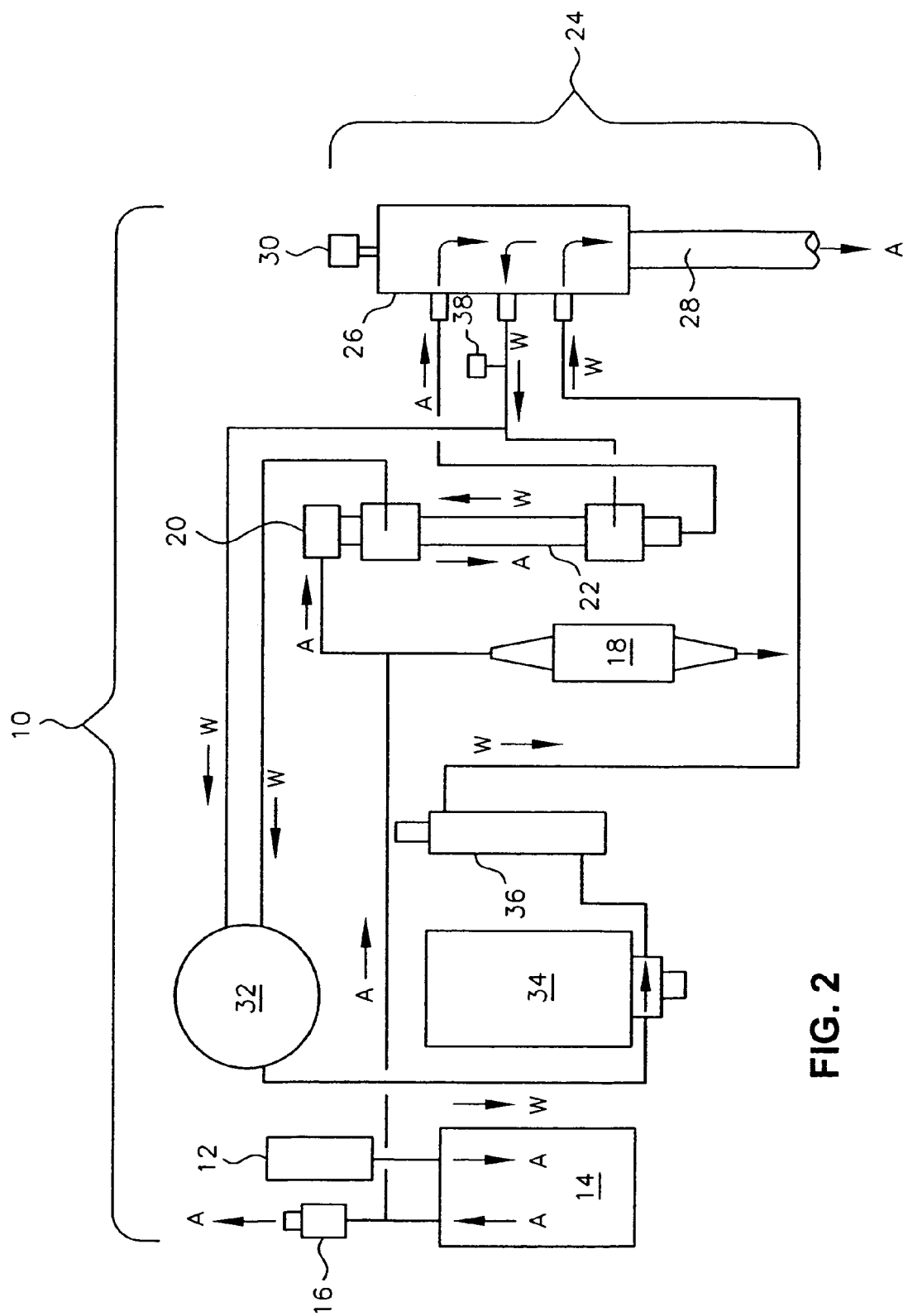
FIG. 2 is a schematic representation of the apparatus illustrated in FIG. 1.

Referring now to FIG. 2, which provides a schematic representation of apparatus 10, arrows have been provided to indicate the flow of air "A" and water "W" through the system. As described earlier, air flows into the interior of the housing of supply unit 11 via air inlet openings (not shown), and water flows into the interior of supply unit 11 via water supply 15 (FIG. 1). The flow of air and water in apparatus 10 will now be described.

Air introduced into the housing of supply unit 11 passes through a vacuum muffler 12. An air compressor 14 pressurizes the air downstream of vacuum muffler 12. A variety of air compressors can be used, and such air compressors are well known in the art. One example of a suitable air compressor is manufactured by Thomas Compressors of Norcross, Ga. and sold under the model number 007CA13F. Other compressors can be substituted. A check valve 16 is provided downstream from air compressor 14 in order to release excessive air pressure.

Air flows from air compressor 14 to a flow control valve 18, which is used to control or regulate the air pressure in system 10. Air then flows to an air filter 20 that is adapted to remove contaminants from the air so that they are not delivered to the patient's respiratory tract. Air then flows through a membrane cartridge 22 and through delivery tube assembly 24. More specifically, air that has been pressurized by air compressor 14 enters connector block 26 and flows outwardly toward the patient through delivery tube 28. An inlet 30 is provided for the optional introduction of oxygen into connector block 26 in order to enrich the proportion of oxygen in the air delivered to the patient.

Referring now to the flow of water through apparatus 10 as illustrated in FIG. 2, water "W" is introduced by means of a reservoir 32 that is fed by water supply 15 (FIG. 1). A water pump 34 is used to deliver a fluid, such as water, from the reservoir 32 to a fluid heater 36 which heats the water to a predetermined temperature or temperature range, as will be described in more detail later. The heated water then flows into delivery tube assembly 24. More specifically, heated water enters connector block 26 and flows into delivery tube 28. In a manner that will be described in more detail later, water then returns from delivery tube assembly 24 into the housing of supply unit 11, and a thermister 38 is used to monitor the temperature of the returning water. The temperature measured by thermister 38 is used to control water heater 36 in order to maintain the temperature of the water within a predetermined range.

A portion of the returned water can flow directly to the reservoir 32 so that it can be recycled through apparatus 10. Another portion of the returned water can flow through membrane cartridge 22 before returning to reservoir 32. Alternatively, all of the water can flow to the membrane cartridge 22. Water is passed through membrane cartridge 22 in order to add water vapor to the air that is flowing in counter-current arrangement through membrane cartridge 22 (as shown in FIG. 2).

Membrane cartridge 22 is preferably a hollow fiber filter module having a microporous membrane that permits the flow of water vapor from the heated water into the air. More specifically, the heated water flows through a housing of the membrane cartridge in contact with the outside surfaces of the hollow fiber membranes. The air flows through the hollow fiber membranes in a direction that is counter-current to the direction of the water in the housing of cartridge 22. Water vapor is transferred through pores in the hollow fiber membranes from the heated water to the air in order to humidify the air for delivery to the respiratory tract of the patient. Although a wide variety of filters can be employed to perform this function, a hollow fiber membrane is preferred. Such filters are available from SPECTRUM MICROGON of Laguna Hills, Calif. under part number M11S-260-01N.

Figure 3:
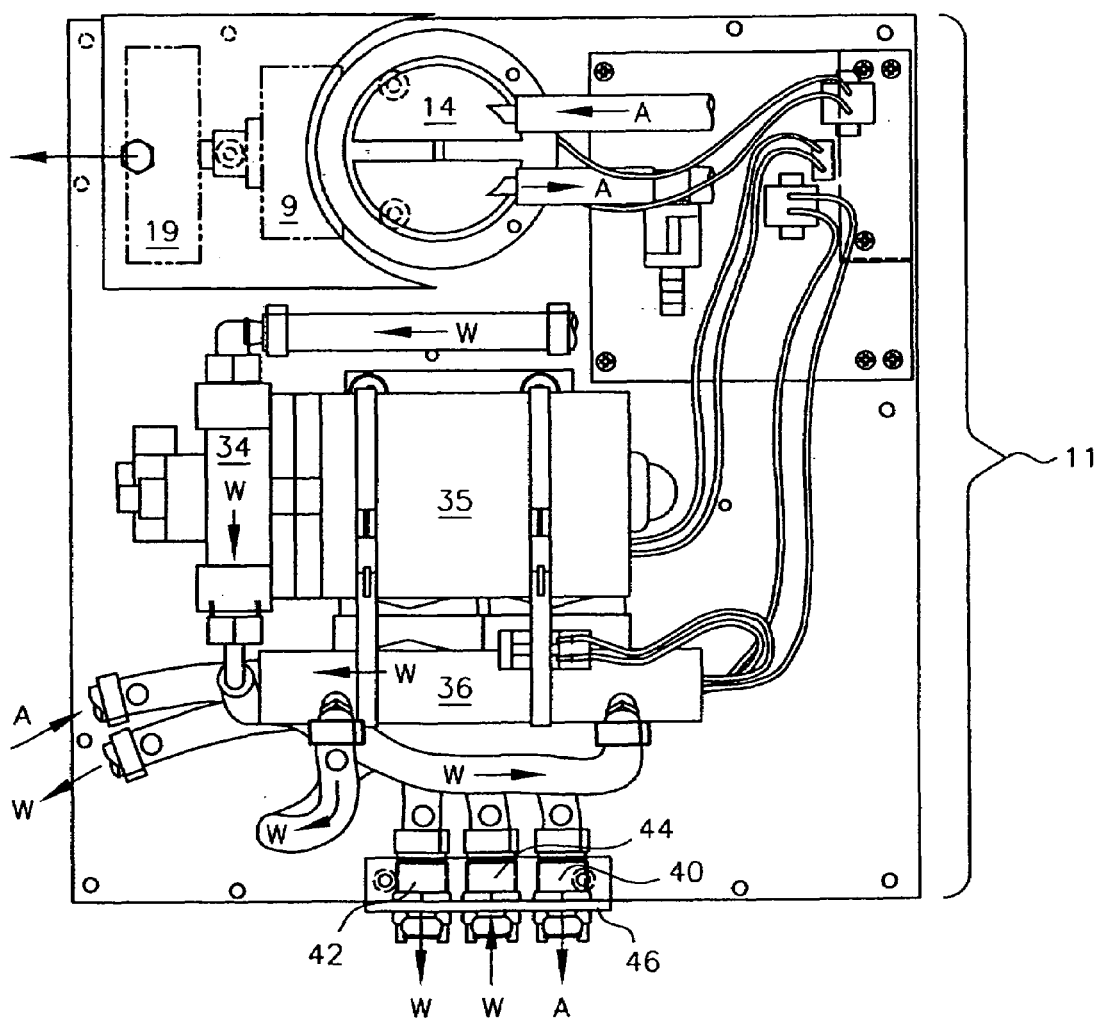
FIG. 3 is a top plan view of an embodiment of a supply unit adapted for use as a component of the apparatus illustrated in FIG. 1, with the housing removed to reveal internal details.

Referring now to FIG. 3, an exemplary preferred embodiment of supply unit 11 is illustrated with the housing removed to reveal the internal details of supply unit 11. The flow of air "A" and water "W" through portions of supply unit 11 will now be described with reference to FIG. 3. Ambient air enters air compressor 14, which is powered by compressor motor 9, for pressurization. An exhaust fan 19 is positioned adjacent to compressor motor 9 in order to withdraw heat from supply unit 11 that is generated by air compressor 14 and compressor motor 9. Air travels from air compressor 14 and past relief valve 16 for delivery to air filter 20 (not shown in FIG. 3) and membrane cartridge 22 (not shown in FIG. 3). Humidified air from membrane cartridge 22 arrives at the tubing illustrated at the lower left-hand side of FIG. 3, as indicated by an arrow, and travels to an air outlet port 40.

At the same time, water is introduced from reservoir 32 (not shown in FIG. 3) into an inlet line 25 through which it is delivered to water pump 34, which is driven by water pump motor 35. Water then travels from water pump 34 to an inlet on the right-hand portion of water heater 36. Heated water then travels from an outlet on the left-hand portion of water heater 36 to a heated water outlet port 42. Water is returned to the interior of the housing of supply unit 11 via a water inlet port 44.

Air outlet port 40, water outlet port 42, and water inlet port 44 are provided by connectors such as quick disconnects that are attached to the housing of supply unit 11 via a bracket 46. The ports 40, 42, and 44 are arranged closely adjacent to one another at the surface of the housing of supply unit 11 so that they can be simultaneously engaged and disengaged to the delivery tube assembly 24 (not shown), as will be described later in more detail.

Figures 4A, 4B:
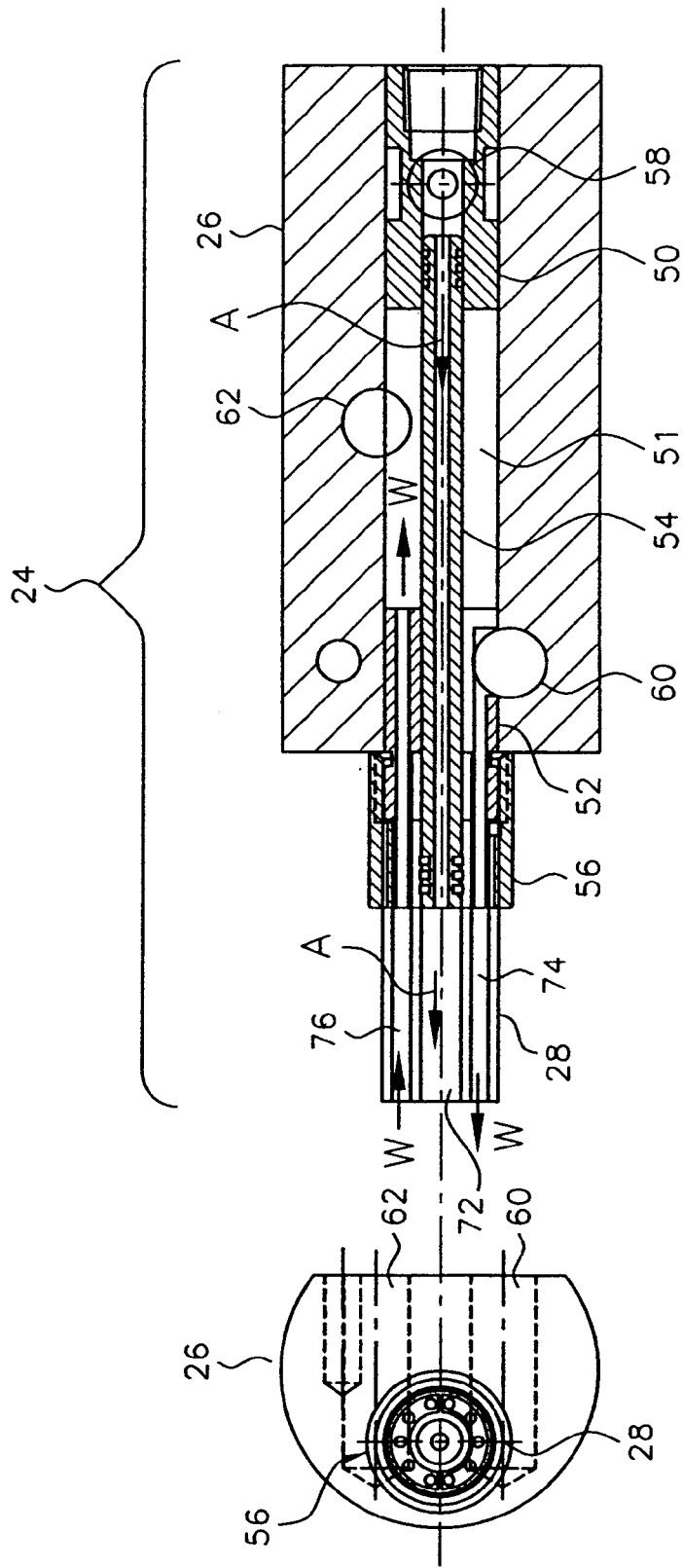
FIG. 4A is a cross-sectional side view of an embodiment of a delivery tube assembly adapted for use as a component of the apparatus illustrated in FIG. 1.
FIG. 4B is an end view of the delivery tube assembly illustrated in FIG. 4A.

Referring now to FIGS. 4A and 4B, aspects of an exemplary delivery tube assembly according to this invention will now be described. Delivery tube assembly 24 is shown in a cross-sectional side view in FIG. 4A and in an end view in FIG. 4B. Delivery tube assembly 24 includes a connector block 26 and a delivery tube 28, as described before, as well as a sleeve 50 inserted into one end of a lumen 51 that extends through the connector block 26 along its axis. Delivery tube assembly 24 also includes a delivery tube insert 52 that is positioned in the opposite end of lumen 51. A length of tubing 54 extends between lumens defined by sleeve 50 and delivery tube insert 52, and a coupling 56 is optionally threaded onto an end of delivery tube insert 52 in order to couple delivery tube 28 to delivery tube insert 52.

Connector block 26 has an air inlet 58, a water inlet 60, and a water outlet 62 in the form of holes formed in a surface of connector block 26. Air inlet 58, water inlet 60, and water outlet 62 provide access for the flow of air and water through connector block 26 to delivery tube 28. Connectors such as disconnects are mounted on connector block 26 at openings 58, 60, and 62 for connection to air outlet port 40, water outlet port 42, and water inlet port 44, respectively.

Figure 5:
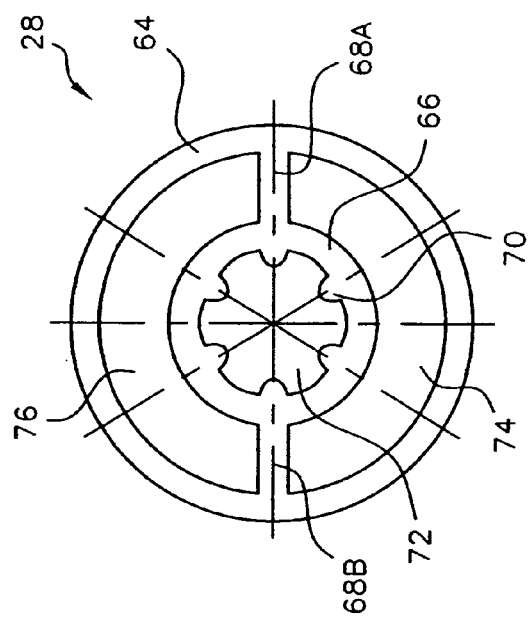
FIG. 5 is a cross-sectional end view of an embodiment of a tube adapted for use as a component of the delivery tube assembly illustrated in FIGS. 4A and 4B.

Referring now to FIG. 5, which provides a cross-sectional end view of delivery tube 28, further details of delivery tube 28 will now be described. Delivery tube 28 can be formed from a variety of materials by a variety of processes. Preferably, delivery tube 28 is formed from polymeric material such as polyurethane. In one embodiment, delivery tube 28 is formed from PELLETHANE #2363-80AE, which has a durometer of Shore 80A. Delivery tube 28 is preferably clear to permit visualization of the water flowing through it. Delivery tube 28 is preferably extruded in long lengths having a substantially constant cross-sectional shape. Although various lengths are contemplated for delivery tube 28, a length of about 10 feet has been discovered to provide adequate performance and adequate versatility to the patient. Other lengths are of course contemplated, depending on the usage of the apparatus, the length of nasal cannula 29, and the heat transfer characteristics from the heated fluid to the air, and matters of cost and design choice.

Delivery tube 28, in the preferred embodiment illustrated, includes a substantially circular outer wall 64 spaced concentrically around a substantially circular inner wall 66. Boundary walls or webs 68A and 68B extend from the inner surface of outer wall 64 to the outer surface of inner wall 66. A plurality of longitudinally extending ribs 70 extends radially inwardly from the inner surface of inner wall 66 and along the axis of delivery tube 28. Inner wall 66 and ribs 70 together define an air lumen 72 that extends along the length of delivery tube 28. In the embodiment illustrated in FIG. 5, six ribs 70 are uniformly spaced. Ribs 70 help to prevent constriction of air lumen 72 in the event that delivery tube 28 is bent in use or otherwise kinked unintentionally.

Outer wall 64 and inner wall 66 together define with boundary walls or webs 68A and 68B a pair of opposed lumens that have a substantially arcuate cross-sectional shape and that substantially surround air lumen 72. More specifically, a heating fluid lumen 74 extends longitudinally along the tube through the lower half of delivery tube 28, and a return lumen 76 extends longitudinally along the tube through the upper half of delivery tube 28. The heating fluid lumen 74 substantially surrounds the lower portion of air lumen 72, and return lumen 76 substantially surrounds the upper portion of air lumen 72. Together, lumens 74 and 76 together cooperate with one another to substantially surround air lumen 72.

Referring again to FIGS. 4A, 4B, and 5, the flow of air "A" and water "W" through delivery tube assembly 24 will now be described. Air enters delivery tube assembly 24 through inlet 58 from air outlet 40 on supply unit 11 and travels to the left in FIG. 4A through the passageway defined by tubing 54. Air then travels into the air lumen 72 of delivery tube 28 and toward the respiratory tract of the patient through the nasal cannula 29 (shown in FIG. 1). If supplemental oxygen or another gas or medicine is to be introduced to the respiratory tract, a source of such a gas or fluid or medication can be attached to the right-hand end of sleeve 50 where a threaded opening is provided. In such a manner, oxygen or other fluids or medicines can be mixed with air for delivery to the patient.

Figure 6A:
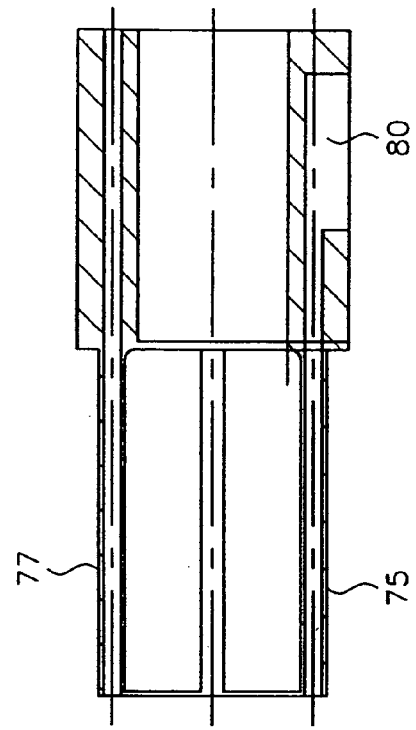
FIG. 6A is a cross-sectional side view of an embodiment of a delivery tube insert adapted for use as a component of the delivery tube assembly illustrated in FIGS. 4A and 4B.
Figure 6B:
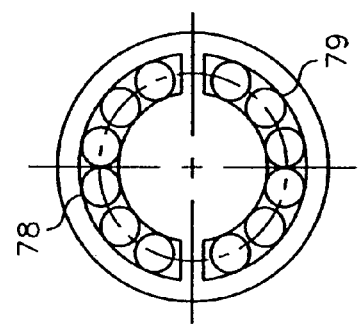
FIG. 6B is an end view of the delivery tube insert illustrated in FIG. 6A.

The manner with which water travels through delivery tube assembly 24 will now be described in further detail with reference to FIGS. 6A and 6B, which illustrate details of delivery tube insert 52. Delivery tube insert 52 includes two extension portions 75 and 77 which are shaped to extend into the lumens 74 and 76, respectively, of delivery tube 28. Extension 77 has a substantially semi-circular cross-sectional shape that corresponds to the shape of return lumen 76 so that extension portion 77 can extend into the interior of return lumen 76 and create a seal. Similarly, extension portion 75 is shaped to fit within heating fluid lumen 74 of delivery tube 28. Although insert 52 can be formed from a variety of materials, aluminum or other metals or plastics can be used. Insert 52 can be formed by molding, machining, or by other known forming methods.

Apertures 78 extend through extension 77 and through the entire length of delivery tube insert 52 from end to end. In this specific embodiment, six apertures 78 are provided to extend from one end of delivery tube insert 52 to the other. Apertures 79, however, extend through extension portion 75 from one end of delivery tube insert 52 but terminate at a location before the opposite end of delivery tube insert 52. In other words, apertures 79 are "blind" in that they do not extend fully through the insert 52. Instead, a side opening 80 (FIG. 6A) is provided for access to at least some of the apertures 79 that extend through extension portion 75. It will be appreciated, as is illustrated in FIG. 4A, that side opening 80 in delivery tube insert 52 is positioned and sized to correspond to water inlet opening 60 that is defined in the connector block 26 of delivery tube assembly 24.

The flow of water through delivery tube assembly 24 will now be described with reference to FIGS. 4A, 5, and 6A. Water enters connector block 26 of delivery tube assembly 24 through water inlet opening 60 from water outlet 42 (FIG. 3) of supply unit 11. Water then travels to the left in FIG. 4A through apertures 79 that extend through extension portion 75 so that water can enter heating fluid lumen 74. In this embodiment, heated water is the heating fluid. The heated water then travels through delivery tube 28 toward the opposite end of the tube.

In a manner that will be described later in more detail, heating fluid lumen 74 is connected to return lumen 76 at the opposite end of delivery tube 28 so that heated water can flow from lumen 74 into lumen 76 for return toward connector block 26. The water then returns through return lumen 76 and enters apertures 78 that are defined in the extension portion 77 of delivery tube insert 52. The water then can flow from one end of delivery tube insert 52 to the other until it can enter the central lumen 51 of connector block 26. Water can then exit connector block 26 through water outlet opening 62 and can return to supply unit 11 through water inlet 44 (FIG. 3).

It will be appreciated that air is caused to flow through the length of delivery tube 28 to the patient and that heated water is caused to flow through the heating fluid and return lumens 74 and 76 in close proximity to the air flow lumen 72. This arrangement has been discovered to provide highly efficient heat transfer from the heating fluid (such as heated water) to the flowing air. Water at its highest temperature (in the upstream portion of the path through the delivery tube) flows through heating fluid lumen 74 in the same direction as air flows through air lumen 72. Water at a slightly lower temperature, due to some heat loss and heat transfer, then travels through return lumen 76 in a counter-current flow pattern with the air in air lumen 72.

Referring now to FIG. 7, the opposite end of delivery tube 28 is illustrated together with a termination that provides access for heating fluid flow between lumens 74 and 76. More specifically, referring back to FIG. 5, the webs or boundaries 68A and 68B are cut and removed in the end portion of delivery tube 28 and a tubing connector 82 is inserted into the end of tubing 28 between inner and outer walls 66 and 64. Connector 82 therefore provides a flow path for air from air lumen 72. Connector 82 also prevents the leakage of water from return lumen 76 or heating fluid lumen 74, yet permits water flow from heating fluid lumen 74 to return lumen 76. The tubing connector 82 is configured to be connected to a cannula connector 86 that extends to a fitting that can be used to introduce the heated and humidified air into a nasal cannula for the delivery of air to the nasal passageway of a patient for respiratory tract treatment or other therapies as described herein.

Figure 8B:
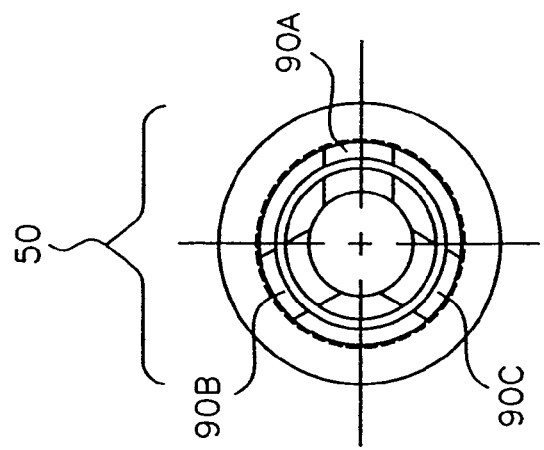
FIG. 8B is an end view of the sleeve illustrated in FIG. 8A.
Figure 8A:
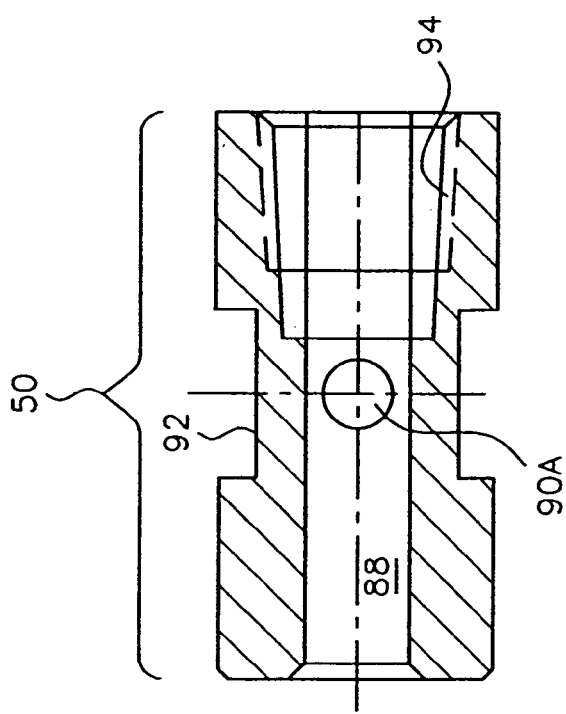
FIG. 8A is a cross-sectional side view of a sleeve adapted for use as a component of the delivery tube assembly illustrated in FIGS. 4A and 4B.

FIGS. 8A and 8B illustrate further details of the sleeve component 50 of delivery tube assembly 24 in order to clarify the manner in which air is delivered through air inlet 58 from the air outlet 40 of supply unit 11. Sleeve 50 can be formed from metallic or polymeric materials. In one preferred embodiment, sleeve 50 is molded or machined from clear polycarbonate. As illustrated in FIGS. 8A and 8B, sleeve 50 has a longitudinally extending lumen 88 and a series of three radially openings 90A-90C. The radial openings 90A-90C extend between lumen 88 and an annular recess 92. Accordingly, air introduced through air inlet 58 from air outlet 40 travels into the annular recess 92 and then travels through radially oriented openings 90A-90C into lumen 88. It will be appreciated that the rotational orientation of sleeve 50 within connector block 26 is not critical because of annular recess 92 so that the air inlet 58 will never be blocked. Air can therefore flow from lumen 88 of sleeve 50 into the interior of tubing 54 which extends into lumen 88.

A threaded opening 94 is provided at the right-hand side of sleeve 50 as it is illustrated in FIG. 8A. Threaded opening 94 provides for threaded engagement with a source of oxygen or some other gas or fluid or medication that is intended to be introduced into the air stream delivered into the patient's respiratory tract.

Another embodiment of an apparatus according to this invention will now be described with reference to FIGS. 9-28. Generally, this embodiment of the apparatus is adapted for portable use such as in a hospital in order to provide respiratory care. More specifically, it is well adapted for conditioning gas from a wall gas outlet or tank source and for delivering the conditioned gas to a patient via a delivery tube assembly that is connected to a nasal cannula or other narrow-gauge cannula, or to a mask. Unlike system 10 this embodiment of the apparatus need not have an on-board air compressor or flow control valve. Accordingly, it can be produced in a significantly smaller and lighter package as compared to system 10. This makes it possible to mount this embodiment of the apparatus on an IV pole next to a patient, such as in a hospital setting.

An inlet connector is provided on the back of the apparatus in order to receive gas from a source of air or oxygen at a set flow rate and oxygen concentration, such as in a hospital. The gas is then heated and humidified in a controlled manner and the conditioned gas is delivered through a delivery tube assembly to a patient through a face mask, nasal cannula, or other cannula at a selected temperature and saturated humidity, without condensation. The patient inspires this controlled gas mixture and any excess respiratory gas is supplied from entrained air that enters around the cannula.

In one exemplary use of this embodiment of the invention, the apparatus is used in a hospital care setting next to the patient. Nurses, nurse's aides or assistants, or respiratory therapy personnel can easily set up and control the operation and daily maintenance of the apparatus. Maintenance personnel can easily perform periodic cleaning and maintenance of the unit between patients. The delivery tube assembly is intended to be disposable, for single patient use.

The compact apparatus can be mounded on a standard IV pole, ¾ to 1¼ inch diameter, by a clamping mechanism on its back. The weight of the apparatus is preferably less than about 6 pounds, excluding a water filled reservoir. The vertical size of the apparatus is preferably less than about 10 inches when mounted on an IV pole, and the width is preferably less than about 4.5 inches. The depth of the apparatus is preferably less than about 3 inches, excluding the clamp and fittings for engagement to the IV pole.

The heat-moisture exchange cartridge, which will be described later in further detail, is preferably accessible for service without disassembly or removal of the apparatus from the IV pole. One example of a cartridge that can be used in an apparatus according to this invention is provided by Spectrum under part number M11S-260-01N or by Vapotherm, Inc. under part number VT01-A. Other configurations of this cassette may is be considered in order to increase surface area and reduce pressure drop.

The hollow fibers of one preferred cartridge have a wall thickness of about 55 to about 60 microns. Other hollow fibers can of course be utilized.

The preferred elimination of the compressor and flow control valve makes it possible to reduce the noise level associated with operation of this embodiment of the apparatus. For example, the sound pressure can be maintained at a level not exceeding about 55 dBA, excluding an audio alarm to be described later.

Gas (air, oxygen, or some combination) is supplied to the apparatus via a tube at about 50 psi maximum pressure. Gas flow can be regulated by a user-supplied restricting valve at the source of the gas so that it can be controlled between preferred flows of about 5 to 50 l/min, more preferably between about 5 to 40 l/min. Water can be supplied to the apparatus from a bag of water via an unconstricted tube of at least about ⅜" internal diameter and not more than about 9" long. An example of a suitable bag and tube set is supplied by Vapotherm, Inc. under part number WR1200. A delivery tube assembly can be attached at the front of the apparatus via a manifold that interfaces to a gas supply port and to heating water supply and return ports. The delivery tube assembly is preferably installed into the manifold by a push-and-turn retaining mechanism.

The unit preferably operates on standard 115VAC, 60 Hz, and power consumption is preferably about 250VA. A standard hospital grade power cord can be supplied with the unit. The software code for the apparatus can be written in "C" language and can be developed and tested in accordance with FDA Software Design Control Validation Requirements.

The apparatus according to this embodiment preferably includes a two (2) digit, seven (7) segment LED display in order to indicate a set point temperature when the temperature is being adjusted. The display can then convert to measured temperature after a short period such as about 5 seconds. The controls for the system, as will be described later in further detail, are preferably tactile feedback switches in a membrane panel. An up and down arrow can be used to set temperature controls. Power on/off can be provided via a single control on the membrane panel. Also, alarm silence/reset controls can be provided via a single membrane switch.

The apparatus in this embodiment preferably includes alarm condition indicators, such as LED's. Such indicators can be labeled with identification or international symbols, as desired. An audio annunciator can be provided to sound when any alarm condition exists, and an alarm silence button can be provided to quiet the alarm for a set period of time such as two minutes. The alarms can be configured to reset if the alarm condition no longer exists. All temperature-related alarms can be defeated until warm up of the apparatus is complete, or until the apparatus has run for a set period of time such as 10 minutes. Other alarms can be defeated for a set period of time, such as 2 minutes, upon start up.

The apparatus in this embodiment can be provided with a "WATER LOW" alarm in order to indicate that the water reservoir is not supplying water in a quantity sufficient to maintain the humidification level at full capacity. The system can remain running for up to 4 minutes if the "WATER LOW" condition continues, before the system is halted.

The apparatus in this embodiment can also be provided with a "SYSTEM FAILURE" alarm in order to indicate that water has entered the gas system and that the supply of gas has been halted or that a so-called "watchdog" timer has failed. Upon a "SYSTEM FAILURE" alarm, the system can be halted and a continuous auto alarm can be activated. Also, the digital display can show "88".

The apparatus in this embodiment can also include a "HIGH TEMP" alarm in order to indicate that the water has overheated to a temperature above a predetermined maximum temperature, such as a temperature about 45° C. Upon such an alarm, the heater and airflow can shut down while the water pump can continue to operate.

The apparatus can also be provided with a "CARTRIDGE" alarm in order to indicate that the humidification cartridge lifetime has been exceeded. The system will continue to operate normally.

A "BLOCKED TUBE" alarm can also be provided. A "BLOCKED TUBE" alarm can indicate that the delivery tube to the patient is either kinked or blocked. Upon such an alarm, the water pump of the apparatus can stop delivering water, and gas flow can be turned off until the condition is corrected.

Various caution and advisory conditions can also be indicated by the apparatus. An indication of such condition can be provided without an audio alarm. For example, a "CLEANING" caution condition can be provided to indicate that the unit is in a special mode for cleaning the gas supply system and that normal controls and alarms are not active. This caution condition indicator can be a yellow back-lit symbol, for example. An example of an advisory condition could be a "POWER ON" indicator to provide an indication that the unit is running. Such an indicator can be green, for example.

The apparatus in this embodiment can be operated in a wide range of ambient temperatures (at least about 15 to about 40° C.) and ambient relative humidity (at least about 20 to about 90%rH). The apparatus can be used at ambient pressure conditions in the absence of hyperbaric conditions.

Preferably, the apparatus in this embodiment is adapted to operate within predetermined parameters. In one exemplary embodiment, the apparatus can operate in a controlled air output temperature range of from about 35.0° C. to about 43.0° C.; a display temperature of from about 15° C. to about 50° C. measured at the water outlet from the cartridge; an operating flow range of about 5 to about 40 l/min.; a gas pressure not to exceed about 60 psi; and a gas composition of dry air and/or oxygen, from about 21% $O_2$ to about 100% $O_2$. Gas humidification should preferably exceed about 95% relative humidity.

The delivery tube assembly, which will be described later in further detail, is hydronically heated. The delivery tube preferably has a reduced pressure drop at the maximum flow of gas as compared to the delivery tube of the first embodiment. This reduction in pressure drop is provided by means of axial gas connectors at the ends of the delivery tube to provide a straight, unobstructed gas flow path between the apparatus and the delivery tube outlet. Details of the delivery tube connectors will be described later.

The water heater used in the apparatus in this embodiment can be 150VA, 115VAC, PID software feedback controlled from a water temperature measured at the outlet of the cartridge. Power to the water heater can be cut off if the heater's surface exceeds a predetermined temperature such as 60° C.

The water pump in the apparatus in this embodiment preferably circulates heating water at a flow rate of from about 0.6 to about 2.0 l/min. The pressure drop of the water pump preferably does not exceed about 10 psi.

Referring now to FIGS. 9-28, exemplary features of an apparatus adapted for portable use such as in a hospital will now be described. Referring first to the schematic representation provided in FIG. 9, an apparatus 100 includes a supply unit assembly 102 and a delivery tube assembly 104, which is adapted to be removably attached to supply unit assembly 102. Supply unit assembly 102 is provided with an inlet 106 for receiving gas from a wall source or from a compressor or a tank or other source. The gas is most preferably provided with a flow rate from about 5 to about 35 l/min. Down stream from inlet 106 is a gas shutoff solenoid valve 108 to prevent gas flow when desired. An exchanger 110 is provided to humidify the gas by means of counter-current flow of water and gas through the exchanger 110. A leak detector 112 and a pressure transducer 114 are provided down stream of exchanger 110. The gas then travels outwardly through delivery tube assembly 104 in order provide a supply of heated, humidified gas as indicated at "A".

Supply unit assembly 102 is configured to receive water from a water bag 116. A pump 118, which can be provided with a 12VDC power supply, urges the water through supply unit assembly 102. A pressure transducer 120 is provided down stream of pump 118 to sense the pressure of the water in the system. The water is then heated in heater 122, which can be provided with a 115VAC power supply. The water, as indicated at "W," advances through supply unit assembly 102 into delivery tube assembly 104. Water W is preferably delivered from supply unit assembly 102 at a flow rate of about 0.6 l/min., and at a pressure of about 8 psi.

The heated water flows through the delivery tube assembly 104 in a manner that will be described in further detail later. The water then returns to supply unit assembly 102 for flow through exchanger 110. The temperature of the water is sensed at a location down stream from the exchanger 110. The water then repeats the circuit through the system in a circulating manner. Water from water bag 116 supplements the recirculating water.

Figure 10:
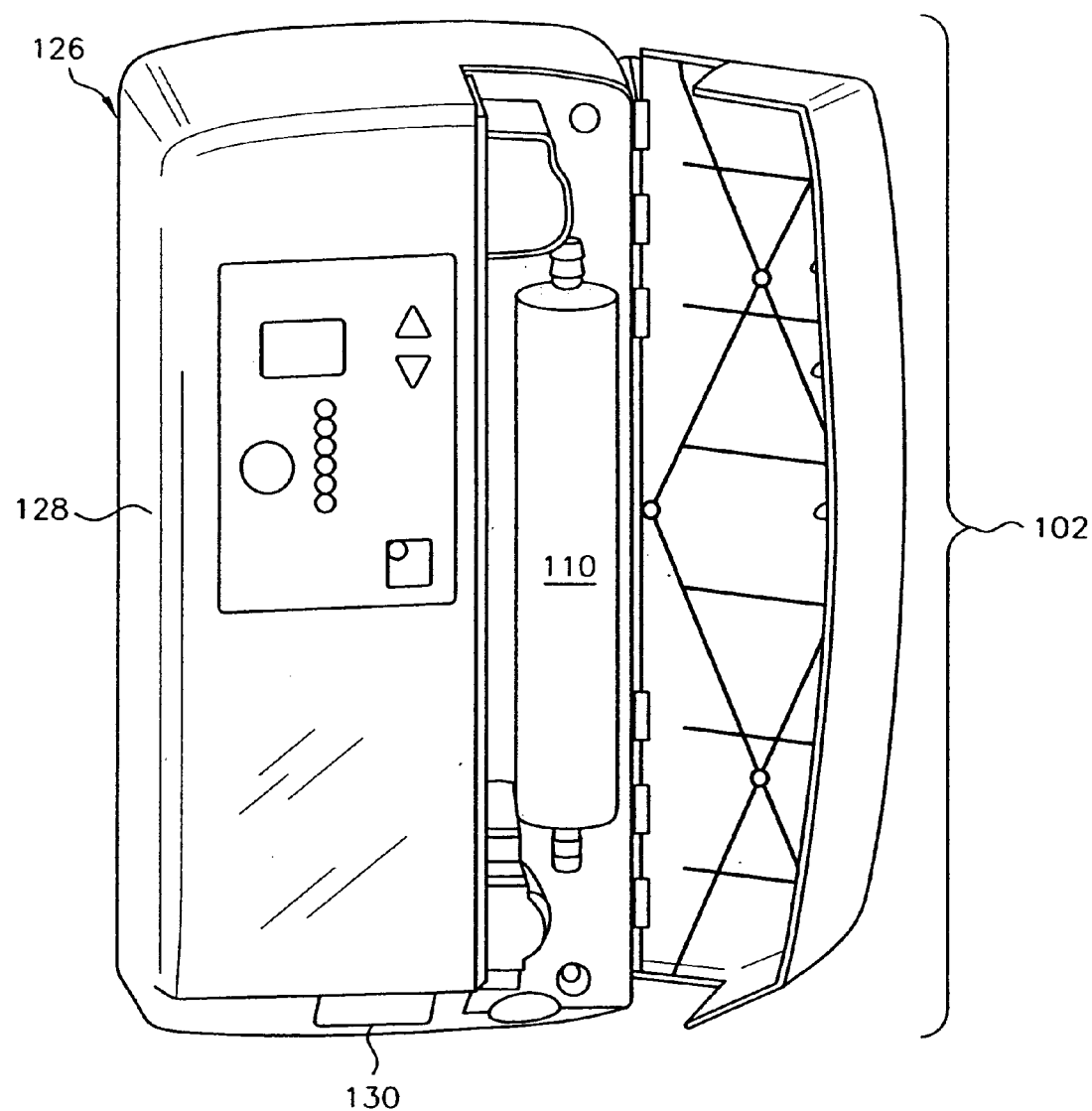
FIG. 10 is a perspective view of an embodiment of a supply unit of the apparatus illustrated in FIG. 9.

Referring to FIG. 10, an embodiment of supply unit assembly 102 is illustrated with a portion of its cover opened to reveal internal details. Supply unit assembly 102 includes a back plate assembly 126 and a cover assembly 128. Within a portion of cover assembly 128 a cartridge for exchanger 110 is provided. Also, a delivery tube port 130 is provided in supply unit assembly 102 in order to facilitate connection of delivery tube assembly 104.

Figure 11A:
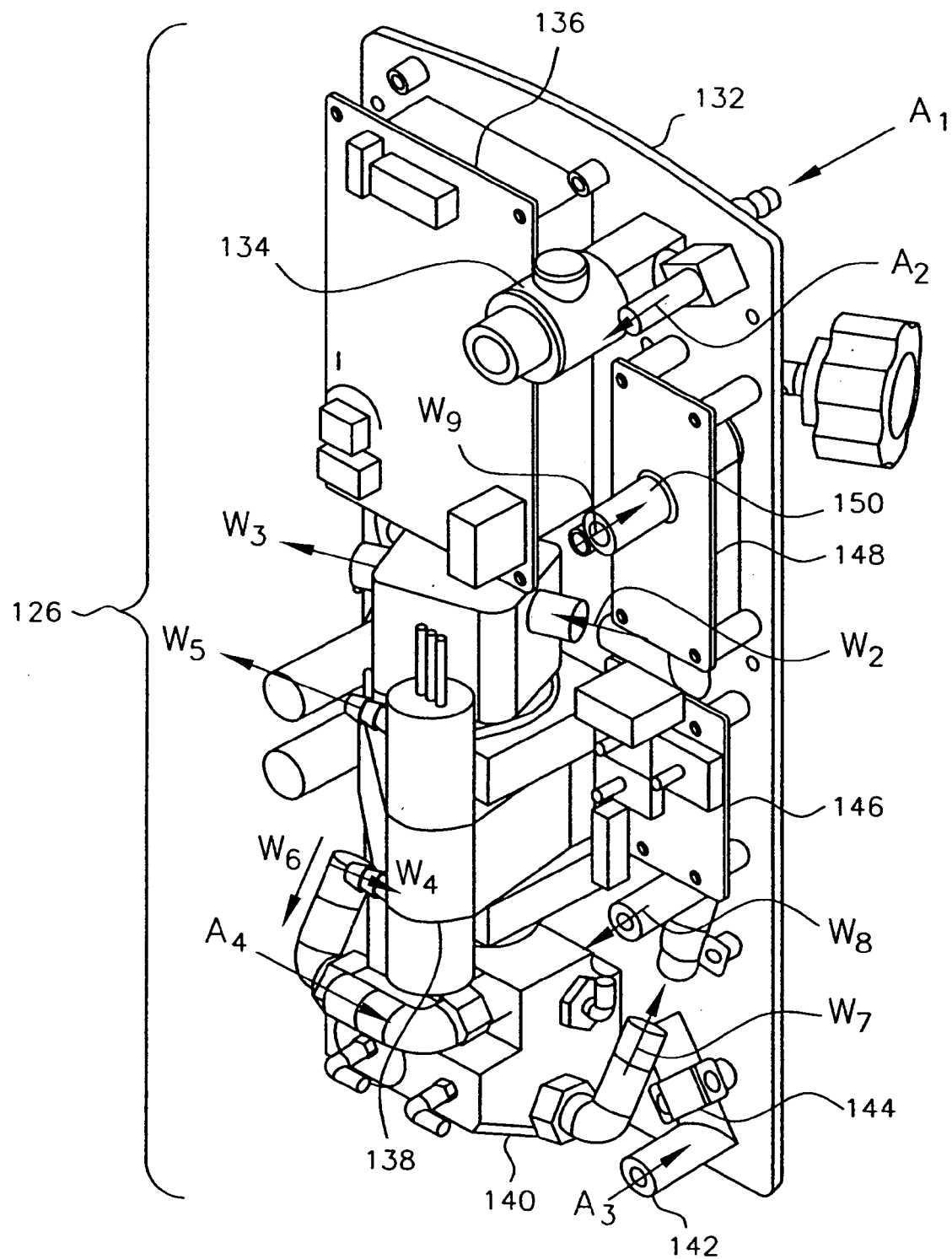
FIG. 11A is a front perspective view of a back plate assembly of the supply unit illustrated in FIG. 10.
Figure 11B:
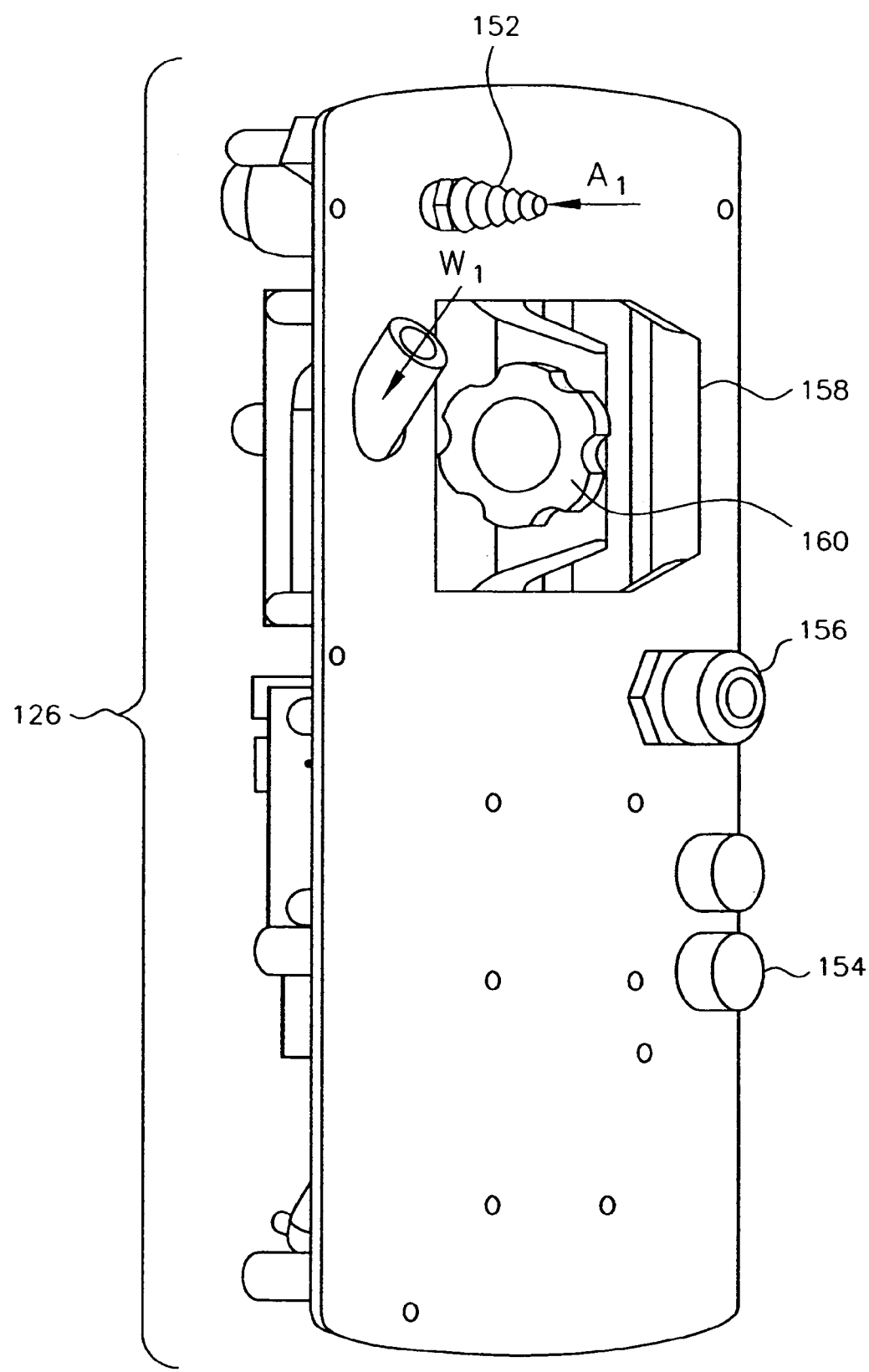
FIG. 11B is a back perspective view of the back plate assembly illustrated in FIG. 11 A.
Figure 15A:
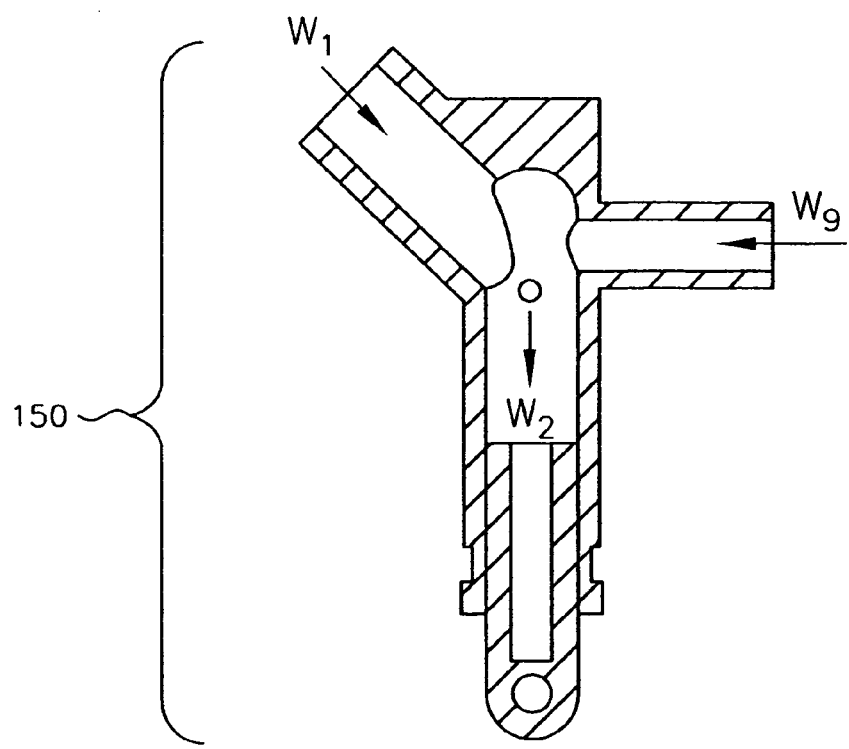
FIGS. 15A and 15B provide a perspective view and a cross-sectional view of a bubble trap assembly adapted for use in the back plate assembly illustrated in FIG. 11A.
Figure 15B:
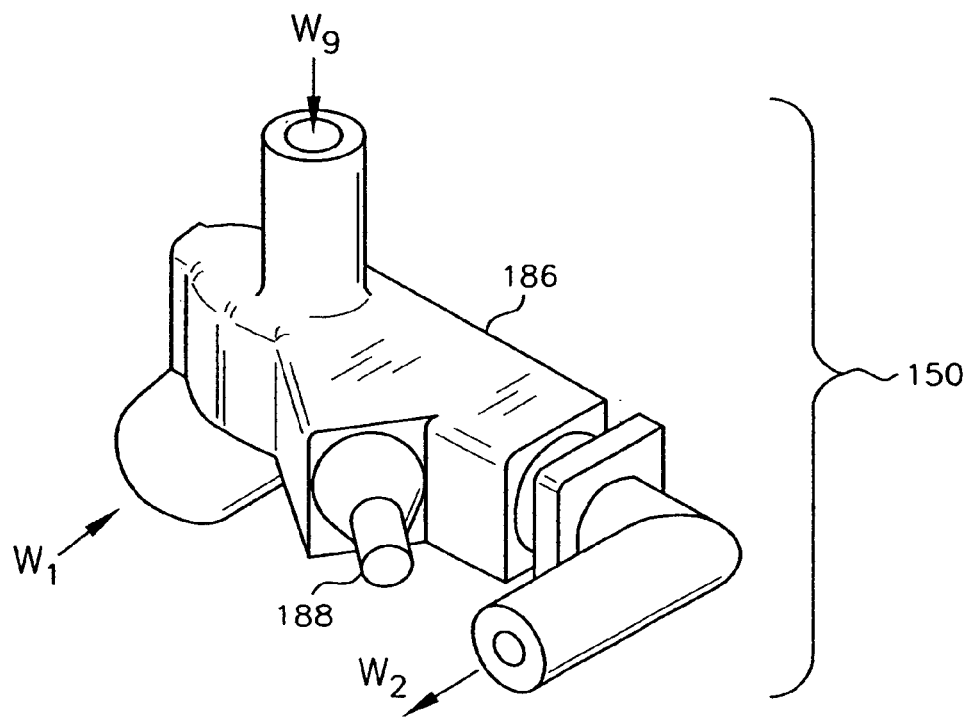

Referring now to FIGS. 11A and 11B, preferred features of back plate assembly 126 will now be described. Back plate assembly 126 includes a back plate 132 to which various electronic and plumbing components are connected. A solenoid 134 (corresponding to solenoid 108 shown in FIG. 9) is connected to back plate 132 adjacent to a power printed circuit board 136. Also connected to back plate 132 is a water pump and water heater assembly 138 (corresponding to water pump 118 and water heater 122 shown in FIG. 9) as well as a manifold assembly 140. An elbow 142 is mounted to back plate 132 by means of a clamp 144. Also mounted to back plate 142 is a sensor printed circuit board assembly 146 as well as a plate fitting 148 for engagement of a bubble trap assembly 150.

Referring specifically to FIG. 11B, which shows a perspective view of the back of back plate 132, back plate assembly 126 also includes a gas inlet fitting 152, a fuseholder 154, and an electric cord attachment 156. Also provided on the back surface of back plate 132 is an IV pole clamp 158, which is provided with a knob 160 in order to facilitate engagement of supply unit assembly 102 to an IV pole. Also provided is a bubble trap assembly.

Referring now to FIG. 12, preferred features of sensor printed circuit board 146 will now be described. Assembly 146 includes a printed circuit board 162 on which are mounted three pressure sensors 164, 166, and 168. Fewer pressure sensors can be used, if desired. Also connected to printed circuit board 162 are connectors 170 and 172. One or two of the sensors are pressure transducers that are connected to the manifold assembly 140 to monitor the pressure of heating fluid as it flows out from, and returns to, the supply unit assembly 102. These sensors can, therefore, detect any blockage in the delivery tube assembly 104 or other condition that could result in an abnormal pressure drop between the heating fluid outlet and inlet. The remaining pressure sensor is a pressure transducer that is connected to the manifold assembly 140 to monitor the pressure of air as it is delivered from the supply unit assembly 102 into the delivery tube assembly 104.

Although three (3) pressure sensors 164, 166, and 168 are illustrated in FIG. 12, it will be appreciated that one or two such sensors can be utilized as well. For example, two of the three sensors 164, 166, and 168 can be used to sense pressure so that a pressure differential can be calculated in the system. Alternatively, in order to reduce the number of pressure sensors from three to two, a straight measurement of pressure can be used as opposed to as pressure differential.

Referring now to FIG. 13, preferred features of the power printed circuit board 136 are illustrated. Assembly 136 includes a printed circuit board 174. Mounted on the printed circuit board 174 is a power supply 176.

FIG. 14 illustrates an embodiment of a display printed circuit board 178 that is adapted for connection to the back plate assembly 126 illustrated in FIGS. 11A and 11B. The display printed circuit board 178 includes a printed circuit board 180 on which is mounted a display 182, such as an LED or LCD display, in order to display to the user of the system a set point temperature or a sensed temperature. Display printed circuit board assembly 178 also includes a series of indicators 184 such as LEDs. The purpose of these indicators will be described later with reference to FIG. 19.

Referring now to FIG. 15, exemplary features of bubble trap assembly 150 are illustrated. The bubble trap assembly 150 helps to remove bubbles from the water as it flows through the system. Assembly 150 includes a fitting 186 on which a water temperature probe 188 is mounted. Probe 188 is used to monitor the temperature of the heating fluid that is circulating through the system.

Referring now to FIGS. 29-37, exemplary features of another embodiment of a bubble trap assembly 400 are illustrated. Bubble trap is assembly 400 operates in a manner similar to bubble trap assembly 150 in that it helps to remove bubbles from the circulating water as it flows through the system. Bubble trap assembly 400 includes a body component 402, a lid component 404, and a fitting component 406.

Exemplary features of the body component 402 of the bubble trap assembly 400 are illustrated in FIGS. 30-33. Body component 402 defines a chamber 408 configured to contain fluid such as water that is circulated through the system. An inlet port 410 is provided to introduce fluid into the interior of the chamber 408. Positioned below inlet port 410 is an outlet port 412, which is provided to permit the flow of water from the chamber 408. Body component 402 of bubble trap assembly 400 also includes a sensor port 414, which is provided so that a temperature sensor (not shown) can be mounted to the bubble trap assembly 400 to monitor the temperature of water as it passes through the chamber 408. Sensors to monitor other conditions of the water or other fluid can be exchanged for the temperature sensor.

Figure 29:
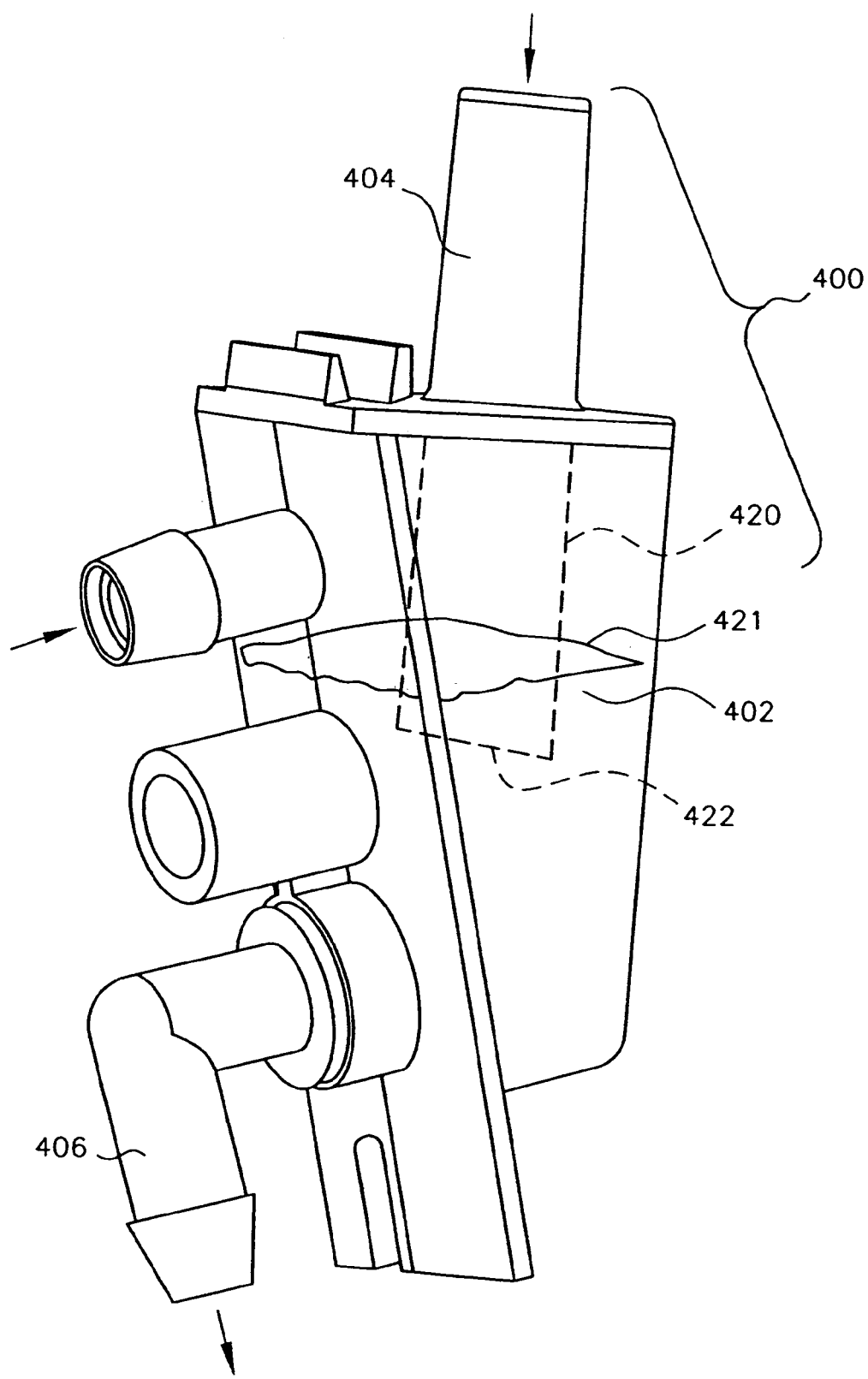
FIG. 29 illustrates another embodiment of a bubble trap assembly adapted for use with the apparatus according to this invention.
Figure 30:
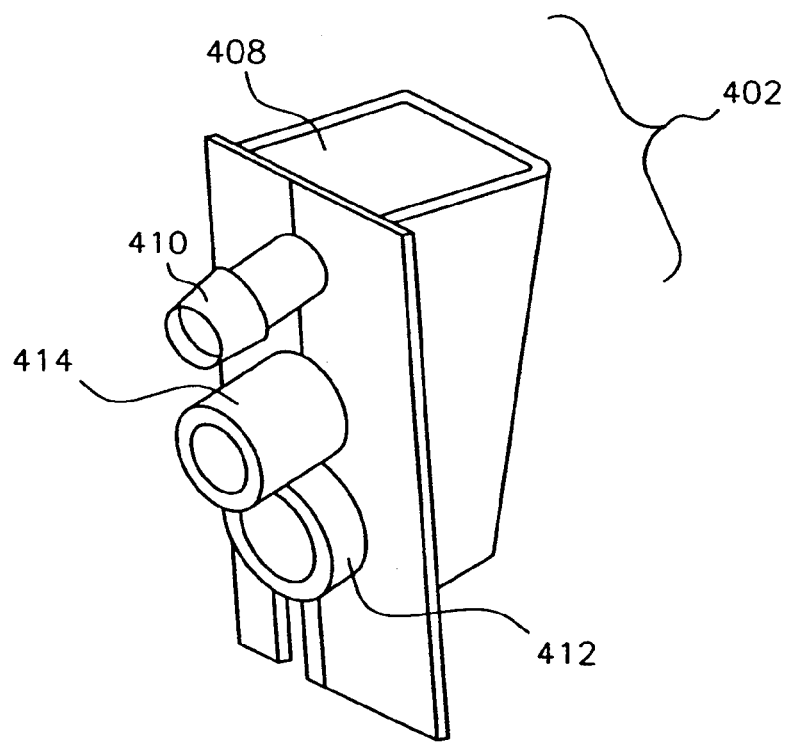
FIG. 30 illustrates a perspective view of an embodiment of a body component of the bubble trap assembly illustrated in FIG. 29.
Figure 31:
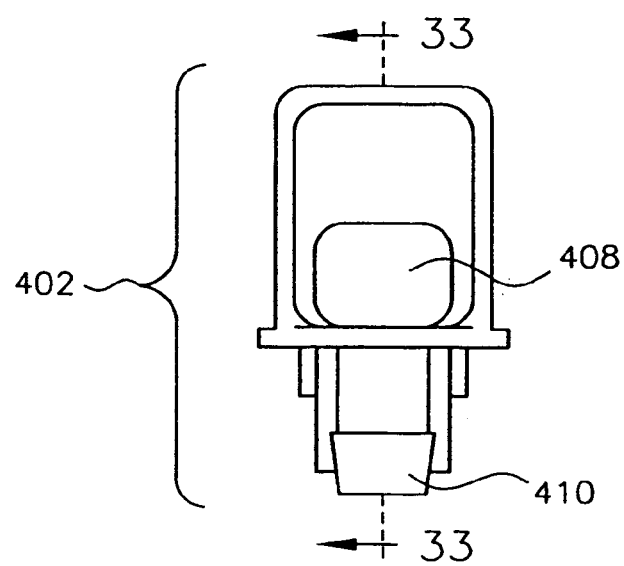
FIG. 31 illustrates a top view of the body component illustrated in FIG. 30.
Figure 33:
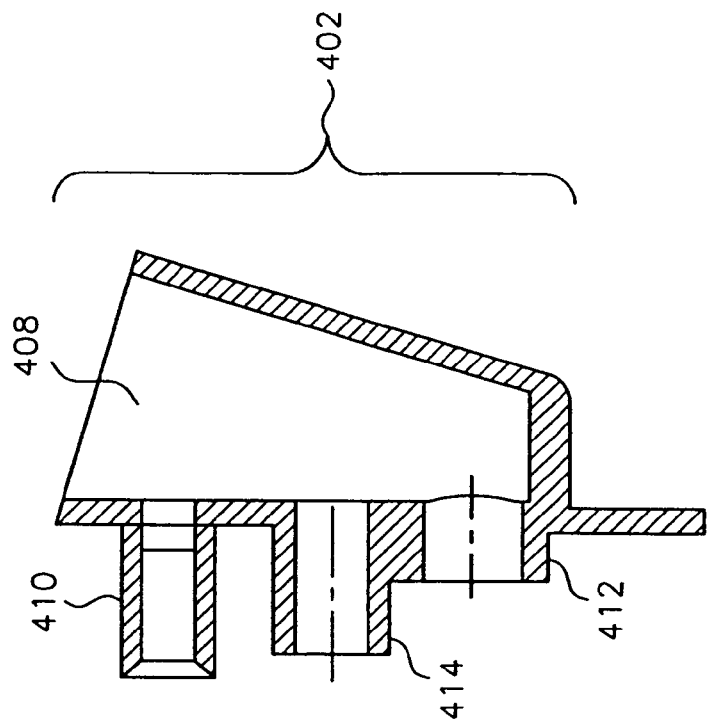
FIG. 33 illustrates a cross-sectional side view of the body component illustrated in FIG. 30.
Figure 32:
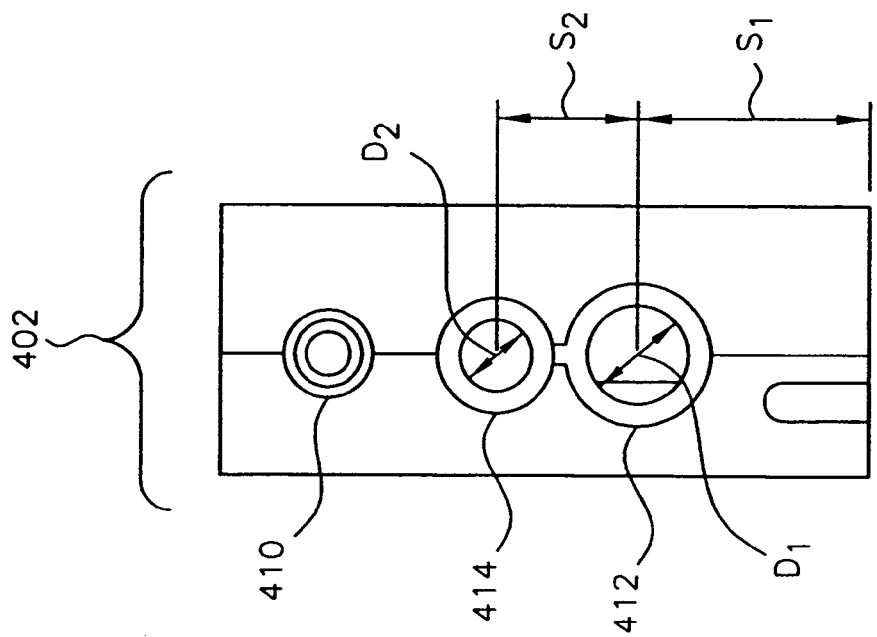
FIG. 32 illustrates a front view of the body component illustrated in FIG. 30.
Figure 34:
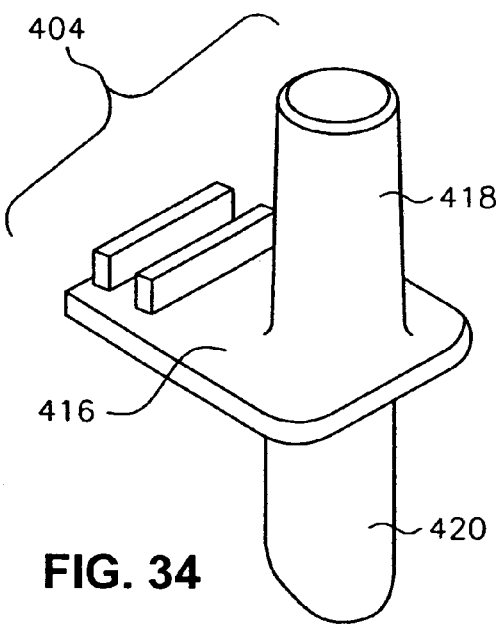
FIG. 34 illustrates a perspective view of a lid component of the bubble trap assembly illustrated in FIG. 30.
Figure 35:
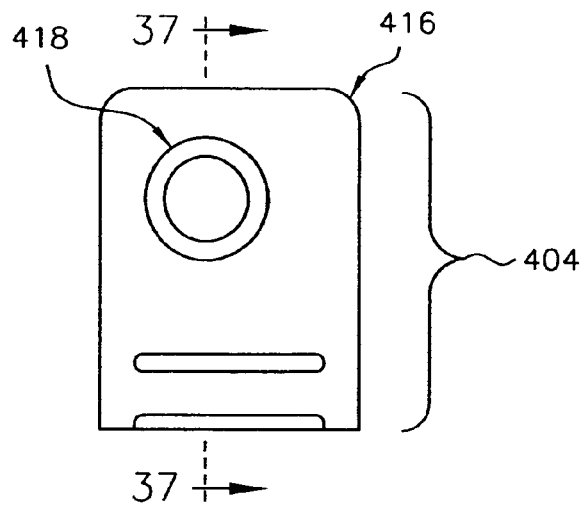
FIG. 35 illustrates a top view of the lid component illustrated in FIG. 34.
Figure 36:
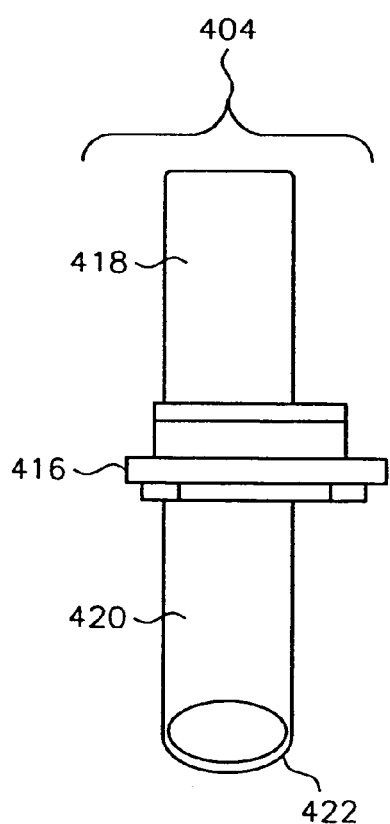
FIG. 36 illustrates a front view of the lid component illustrated in FIG. 34.

Referring specifically to FIG. 32, the outlet port 412 is provided with a diameter $D_1$ to receive a fitting such as the fitting 406 illustrated in FIG. 29. Sensor port 414 is provided with a diameter $D_2$ sized to receive a temperature or other sensor. Outlet port 412 is spaced a distance $S_1$ from the bottom of a flange portion of the body component 402. The center of outlet port 412 is spaced a distance S2 from the center of the sensor port 414.

An exemplary embodiment of a lid component 404 of the bubble trap assembly 400 is illustrated in FIGS. 34-37. Lid component 404 includes a lid 416 sized and shaped to enclose the opening at the top of the chamber 408 of the body component 402 of the bubble trap assembly 400. Lid component 404 also includes an upwardly-extending inlet port 418, which is configured for mating connection to a source of supplemental fluid such as a water bag. Specifically, a water bag can be connected to inlet port 418 to permit the flow of water from the water bag (not shown) into the bubble trap assembly 400. Lid component 404 also includes a downwardly-extending wall 420 that provides for an extension of the inlet port 418 into the interior of the chamber 408 of the bubble trap assembly 400.

Figure 37:
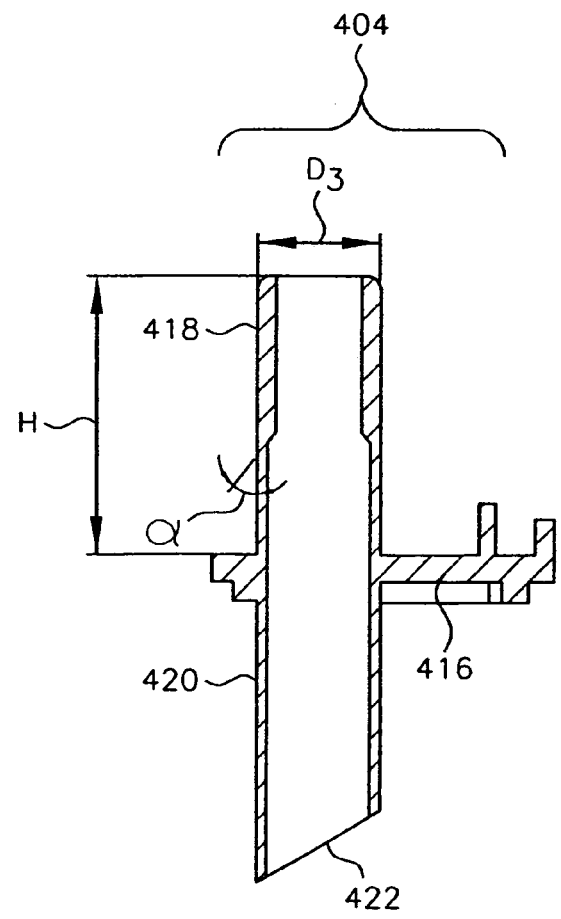
FIG. 37 illustrates a cross-sectional side view of the lid component illustrated in FIG. 34.

As is illustrated in FIG. 37, the wall 420 that extends the inlet port 418 terminates at an angled tip 422. The inlet port 418 is provided with a height H so that it can be mated to a source of water. The inlet port 418 is tapered at an angle α to facilitate sealing engagement between the inlet port 418 and the water supply (not shown). Also, an upper end of inlet port 418 is provided with a diameter $D_3$ suited for mating engagement with a water supply and for the flow of water and air (as described below).

Although it is shown only in phantom in FIG. 29, it will be understood that the wall 420 that extends inlet port 418 into the interior of chamber 408 extends downwardly, substantially parallel to the rear wall of chamber 408. The tip 422 of the wall 420, and the length of the tubular wall 420, are configured such that the tip 422 terminates at a point below the axis of the inlet port 410 of the body component 402. The tip 422 of the tubular wall 420 also extends to a position above the axis of the outlet port 412 provided on the body component 402. In other words, the tip 422 of wall 420 extends downwardly into the chamber 408 to an elevation above that of outlet port 412 and below that of inlet port 410.

Referring generally to FIGS. 29-37, the operation of bubble trap assembly 400 will now be described. As is indicated by the arrows shown in FIG. 29, circulating water will enter the bubble trap assembly 400 through the inlet port 410; the circulating water will exit the bubble trap assembly 400 through outlet port 412 and fitting 406; and supplemental water will enter the bubble trap assembly 400 through the inlet port 418 in the lid component 404 of the bubble trap assembly 400.

The chamber 408 of the bubble trap assembly 400 is substantially enclosed by virtue of the engagement between the lid 416 of the lid component 404 and the upper surface of the body component 402.

As water (or another liquid or fluid) is circulated through the system, air bubbles or air otherwise entrained within the circulating water will be trapped within the chamber 408. The circulating water received in the chamber 408 flows toward the bottom of the chamber 408 and then outwardly through the outlet port 412 and the outlet fitting 406. A small reservoir of water will form in the chamber 408 as indicated by the water level 421 illustrated in FIG. 29. The air that separates from the circulating water within the chamber 408 accumulates at the top of chamber 408.

In operation, circulating water with air bubbles enters the bubble trap chamber 208 by an inlet tube 410 near the top of the bubble trap assembly 400. Air collects in the top of the chamber 408 while the circulating water falls to the bottom and leaves by the outlet 412 and the outlet fitting 406. A third tube, defined by the wall 420, is connected to the reservoir and enters the top of the bubble trap assembly 400, normally terminating at a tip 422 positioned below the water surface within the chamber 408. As the volume of trapped air increases, it lowers the water surface 421 in the bubble trap chamber 408. When the water surface 421 is below the level of the tube 420 from the supply reservoir, air bubbles are formed in the tube 420 and pass upwardly through the tube 420 into the water supply bag. To avoid bubbles blocking the water tube 420 and inlet tube 418 from the reservoir, the internal diameter is preferably about ⅜ inch or greater. The length and shape of the tube 420, and the internal volume of the bubble trap chamber 408, are selected to collect an optimum amount of air bubbles when the system according to this invention is operating. The water level 421 preferably remains sufficiently high to avoid recirculation of air through the outlet port 412 at the lower end of the chamber 408.

Accordingly, the bubble trap assembly 400 removes air from circulating water and allows the air to return to the water supply reservoir. Although the bubble trap assembly (400 or 150) is not a critical feature of the system according to this invention, the bubble trap assembly helps to prevent air from blocking water circulation, which blockage could affect the operation of the system. Also, the water pump of the system may not operate properly if it becomes filled with air.

The bubble trap assembly 400 is particularly beneficial for use with a compact version of the system that is capable of being attached to an I.V. pole. In such a system, there is no room for a built-in open reservoir into which circulating air could simply vent through the water surface. Instead, a compact version of the system utilizes an external reservoir such as a bag of water. A bag is preferably used because it can change volume with no substantial change in pressure and because it is light, easy to change, and easy to hang on the I.V. pole. However, the use of an external reservoir such as a water bag closed the water circulating system and, therefore, the bubble trap assembly 150 or 400 is adapted to allow circulating air to be displaced into the reservoir bag where it has no effect on the operation of the system. Displaced air is automatically replaced with its own volume of supplemental water form the reservoir.

Figure 41:
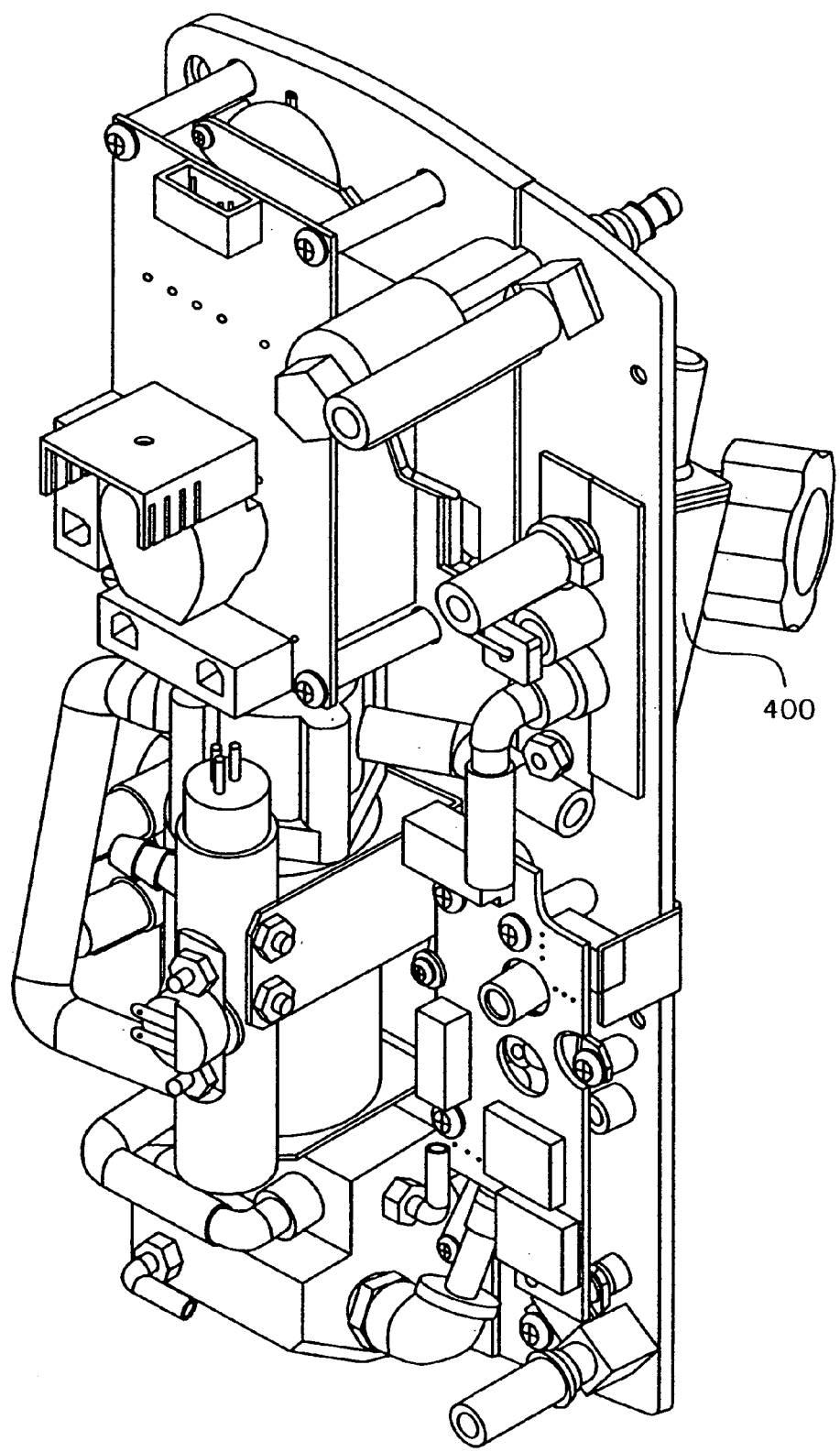
FIG. 41 illustrates a front perspective view of another preferred embodiment of a back plate assembly of the supply unit.

Referring to FIG. 41, another preferred embodiment of a back plate assembly adapted for use in the supply unit is illustrated. It differs from the assembly illustrated in FIG. 11A in that it includes a bubble trap assembly 400. Other modifications are also illustrated in FIG. 41.

Figure 16:
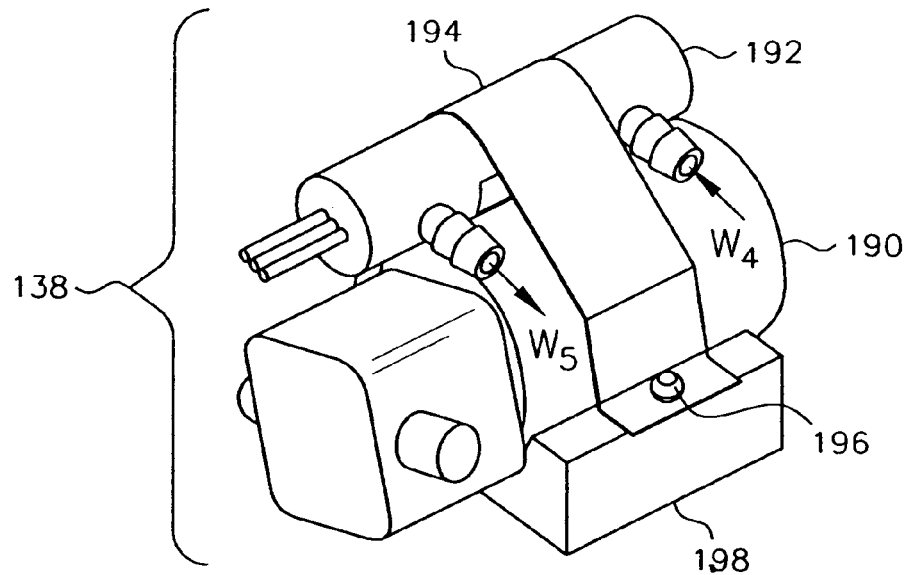
FIG. 16 is a perspective view of a water pump and water heater assembly adapted for use in the back plate assembly illustrated in FIG. 11A.

Preferred features of a water pump and water heater assembly 138 are illustrated in FIG. 16. Assembly 138 includes a water pump 190 as well as a water heater 192. Water pump 190 and water heater 192 are mounted by means of a heater and pump strap 194 and a screw 196 to a pump base 198.

Figure 17:
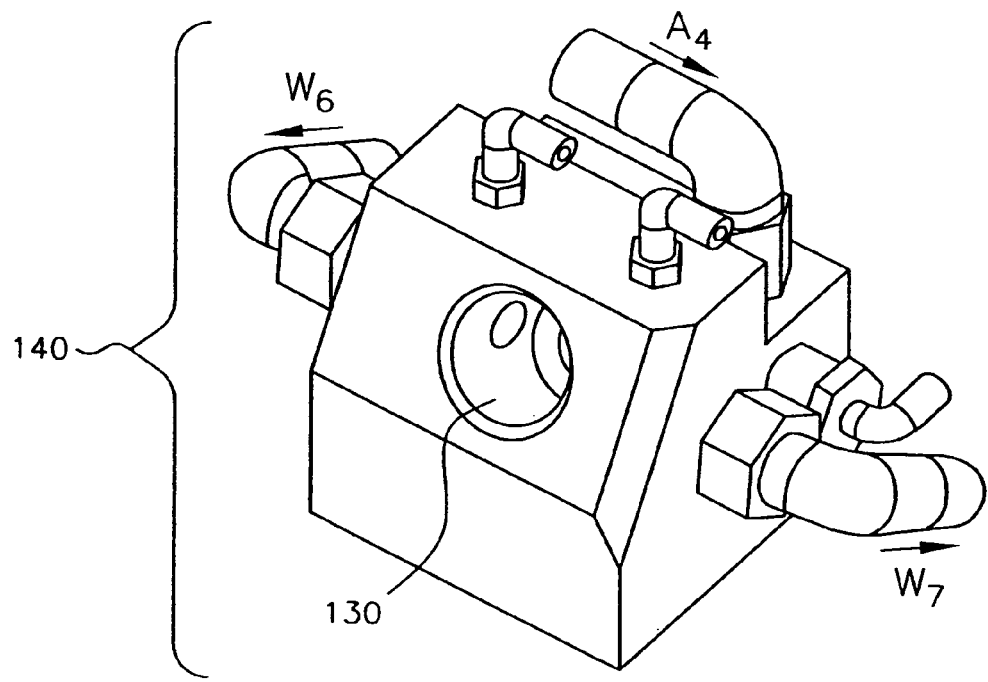
FIG. 17 is a perspective view of a manifold assembly adapted for use in the back plate assembly illustrated in FIG. 11A.
Figure 24A:
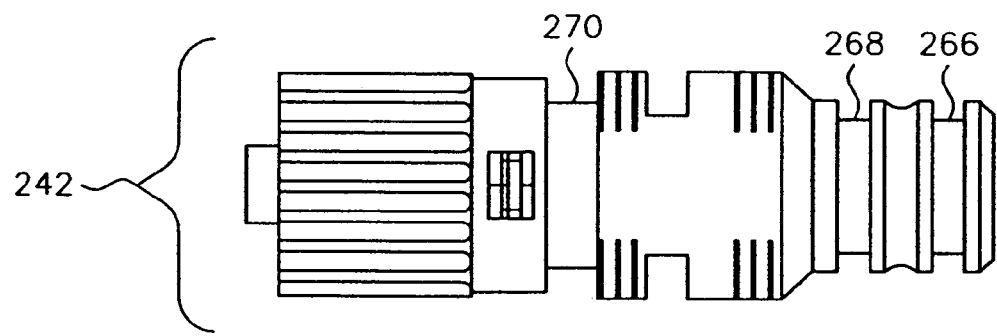
FIGS. 24A-24D provide views of an embodiment of an inlet fitting adapted for use in the delivery tube assembly illustrated in FIG. 22.
Figure 24B:
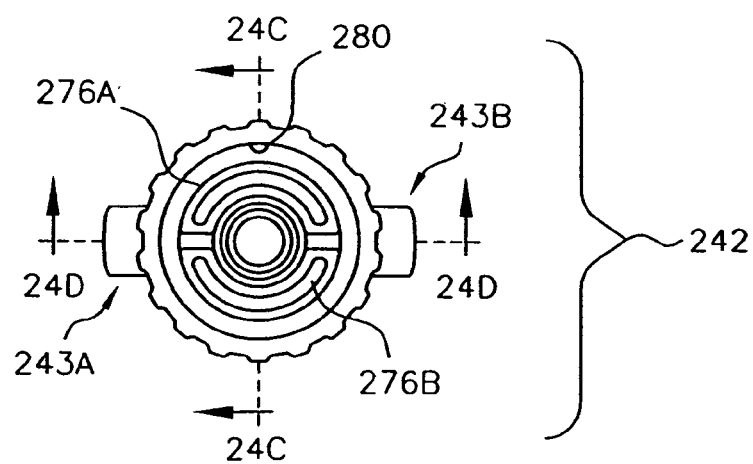
Figure 24C:
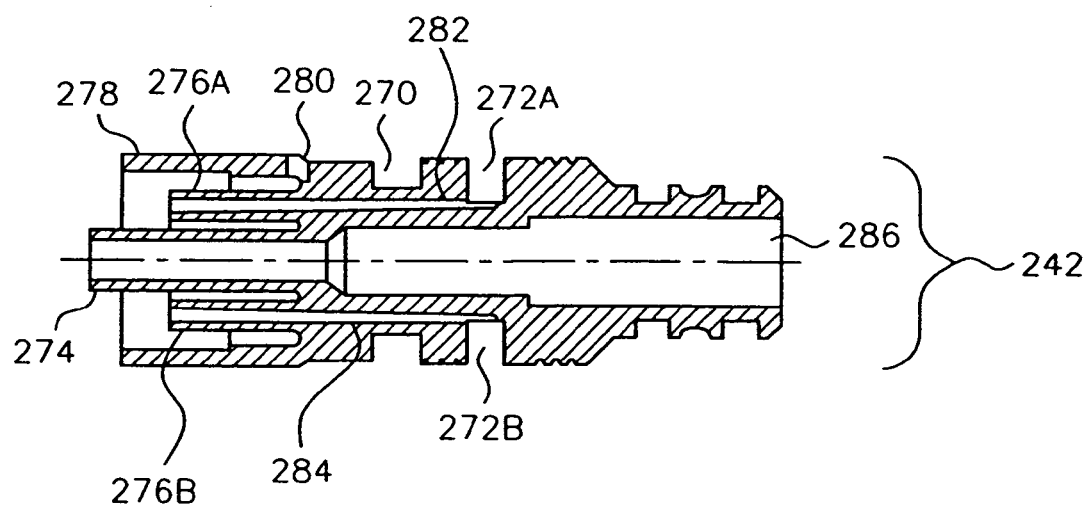
Figure 24D:
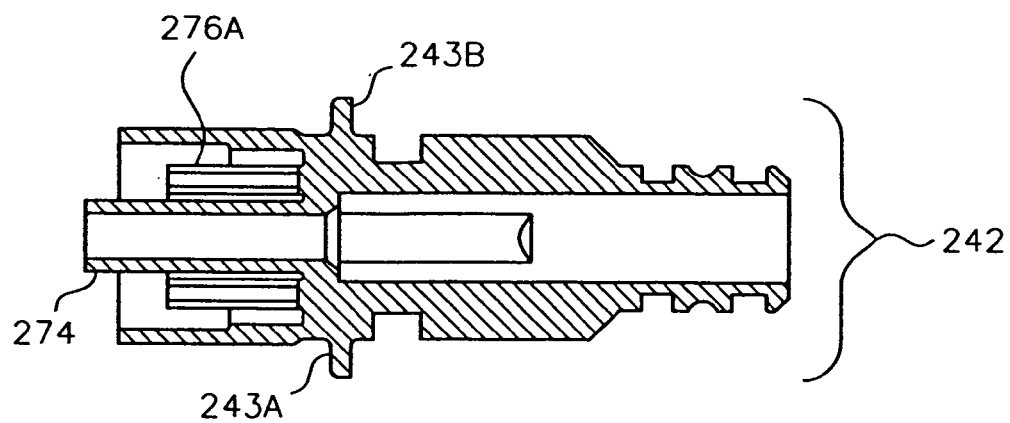

Referring now to FIG. 17, an enlarged view of manifold assembly 140 is provided. Manifold assembly 140 provides delivery tube port 130 into which an end of the delivery tube assembly 104 can be inserted. Further details of the connection between delivery tube assembly 104 and manifold assembly 140 will be provided later with reference to FIGS. 26A and 26B.

FIG. 18 illustrates preferred features of cover assembly 128 of supply unit assembly 102. Cover assembly 128 includes a main housing 200. Display printed circuit board 178 (illustrated in FIG. 14) can be mounted to main housing 200, and a membrane panel 202 can be provided for user control of the supply unit assembly 102. Main housing 200 is provided with a magnetic latch 204. Cover assembly also includes a housing door 206 which is mounted to main housing 200 by means of a hinge 208. A magnetic plate 210 on housing door 206 provides for releasable engagement between housing door 206 and main housing 200 in order to maintain housing door 206 in the closed position during operation of apparatus 100.

Preferred features of membrane panel 202 are illustrated in FIG. 19. Membrane panel 202 includes a display window 212 through which a digital temperature display in the form of an LED or LCD display can be viewed by the user. Membrane panel 202 also includes windows for alarm indicators such as a window 214 for a "WATER LOW" indicator, a window 216 for a "SYSTEM FAILURE" indicator, and a window 218 for a "HIGH TEMP" indicator, a window 220 for a "CARTRIDGE" indicator, and a window 222 for a "BLOCKED TUBE" indicator. A mute symbol 224 is provided on membrane panel 202 as well as an "ON/OFF" indicator. Up and down arrows 228 and 230 respectively are also provided on membrane panel 202 for increasing or decreasing a set temperature.

Although not shown in the appended figures, an optical detector is optionally provided as part of the system in order to detect water that might enter the air passages. For example, an optical detector can be provided to detect the leakage of water if water were to leak from the water passage to the air passage by means of the vapor exchange cartridge. If the membrane material of the exchanger cartridge should weaker or fail, water could enter the air stream.

The preferred detector utilizes a light beam that passes through the air stream leaving the cartridge. The intensity of the light beam is continuously measured during operation of the system. Drops of water in the air stream tend to attenuate the light beam. If the intensity of the light beam drops below a preset value, the operating software can be configured to close the air inlet solenoid and cause a "system failure" alarm in order to shut off the system.

FIG. 20 provides a perspective view of main housing 200 of cover assembly 128. Main housing 200 has an opening 232 corresponding in size to membrane panel 202 (see FIG. 19). Main housing 200 also includes an opening 234 for access to the delivery tube port 130 in manifold assembly 140 (see FIG. 17). Main housing 200 also includes a base portion 236 to provide full coverage of back plate assembly 126 even when housing door 206 is in the open position as illustrated in FIG. 18.

As is illustrated in FIG. 21, housing door 206 of cover assembly 128 includes a pair of recessed portions 238 and 240. These recessed portions 238 and 240 of housing door 206 conform to the base portion 236 of main housing 200 to provide a closed housing when housing door 206 is in a closed position (not shown). It will be understood that exchanger 110 will be enclosed between surfaces of main housing 200 and housing door 206 when housing door 206 is in the closed position. Nevertheless, when opened by a user of the system, housing door 206 provides easy access to exchanger 110 for maintenance and/or replacement.

Referring now to FIG. 22, preferred features of delivery tube assembly 104 are illustrated. Delivery tube assembly 104 includes an inlet fitting 242 on which three o-rings 244, 246, and 248 are mounted for sealing engagement with an interior surface of manifold assembly 140 (see FIG. 17). Delivery tube assembly 104 also includes an extruded tube 250, which is preferably provided with a length of about 7 feet to extend between supply unit assembly 102 and the patient. Delivery tube assembly 104 also includes an outlet fitting 252 mounted at the opposite end of extruded tube 250 in order to facilitate connection to a nasal cannula or mask, which makes it possible to introduce heated and humidified gas to the respiratory tract of the patient.

Generally, the inlet fitting 242 of the delivery tube assembly 104 is provided to retain the delivery tube assembly in place; to allow quick, reliable connection and disconnection of the delivery tube assembly; to connect two (2) water passages and one (1) air passage; and to maintain separation between the water and air passages. The delivery tube has a central air channel enclosed by two (2) water channels. Each channel is connected to a corresponding channel in the base connector. The air channel is axial and passes straight through the connector. The two (2) water channels are brought out through the sides of the connector diametrically opposite one another.

When the connector is inserted into a manifold such as manifold 140 in the base unit and releasably locked into place, the two (2) water channels in the connector line up with matching water channels in the manifold. Ball valves closing the manifold water channels are automatically opened by the action of inserting the connector, so that when the connector is fully inserted and locked into position the water can flow from the manifold into a water channel in the connector, and thence into a water channel in the delivery tube. Returning water from the delivery tube flows through the opposite side channel of the connector and into the manifold through the matching channel.

Leakage to the outside is prevented by an o-ring seal around the connector. Leakage to the air channel is prevented by two (2) o-rings around the connector between the water channels and the air channel. All three (3) o-rings are compressed between the connector and the manifold is when the connector is inserted, so that water and air passages are effectively isolated.

Regarding the manifold (such as manifold 140), the manifold is provided to make connections with the delivery tube; to maintain separation of water and air passages; and to retain water in the base unit when the delivery tube is disconnected. The preferred manifold 140 has all three (3) fluid passages integrated into a single block, providing improved dimensional stability as well as being compact and allowing quick replacement of delivery tubes. In operation, the manifold compresses the o-rings of the delivery tube base fitting and effectively separates the water and air circulations. As an additional safety measure, a seep hole is preferably provided in the manifold. Any water that passes the first of the o-rings separating the water and air circulation leaks out through this seep hole and does not reach the second o-ring seal. Water leaks into the air passage are therefore minimized or preferably avoided entirely, even if the first o-ring fails.

Regarding the tip connector (such as the outlet fitting 252) of the delivery tube, the tip connector terminates the delivery tube; connects outgoing and return fluid passages in the delivery tube; and provides for connection to the air passage. The tip connector permits rapid assembly and reduces the resistance to water flow through the delivery tube assembly. The connector has an elongated, tapered axial tube that makes a gas-tight fit with the central air passage in the delivery tube. The shell of the connector has a slight inside taper that provides a water-tight seal with the outside of the delivery tube after assembly. Internal passages in the tip connector allow water to flow between the two (2) water channels, removing the need to modify the tubing material.

Exemplary details of additional preferred embodiments of the delivery tube assembly will now be described.

Referring to FIG. 23, the extruded tube 250 includes an outer tube 254 and an inner tube 256, wherein inner and outer tubes 254 and 256 share a common axis. Inner tube 256 is connected to outer tube 254 by means of a pair of webs 258A and 258B that extend across the annular space between outer tube 254 and inner tube 256. Inner tube 256 defines an inner lumen 260 through which gas flows from the supply unit assembly 104 toward the patient. The inner tube 256, outer tube 254, and webs 258A and 258B together define a pair of outer lumens each having a semi-circular cross-sectional shape. More specifically, a first outer lumen 262 and a second outer lumen 264 are defined by tubes 254 and 256 and webs 258A and 258B. First and second outer lumens 262 and 264 provide passages for flow of warming fluid such as water that flows outwardly from supply unit assembly 102 into delivery tube assembly 104 and then returns from delivery tube assembly 104 to supply unit assembly 102 for re-circulation.

It is the heat transferred from warmed fluid in outer lumens 262 and 264 to gas within inner lumen 260 that provides the heating mechanism of the delivery tube.

It should be noted that outer lumens 262 and 264 according to this invention need not be dedicated to a particular water or fluid flow direction. More specifically, outer lumen 262 can provide for outward water flow toward the patient or it can provide for return flow toward the supply unit assembly 102. Likewise, outer lumen 264 can provide for outward water flow toward the patient or it can provide for return flow toward the supply unit assembly 102. The direction of flow through the lumens will be determined by the orientation of inlet fitting 242 with respect to the extruded tube 250, which is not critical, and the orientation of the inlet fitting 242 in port 130 of manifold assembly 140, which is not critical. In other words, inlet fitting 242 of delivery tube assembly 104 can be assembled without regard for alignment of a particular outer lumen 262 or 264 with respect to the orientation of the inlet fitting 242.

Referring now to FIGS. 24A through 24D, inlet fitting 242 of delivery tube assembly 104 is provided with external, circumferential grooves 266, 268, and 270. These grooves 266,268, and 270 accommodate the o-rings 244, 246 and 248 shown in FIG. 22. It will be understood that, when inlet fitting 242 is inserted into manifold assembly 140 at the delivery tube assembly port 130, o-ring 248 will provide a seal between inlet fitting 242 and an inner surface of the manifold, and o-rings 244 and 246 will provide a fluid-tight seal between inlet fitting 242 and a smaller diameter region in the inside of the manifold. Inlet fitting 242 is also provided with ports 272A and 272B for reasons that will be made clear later.

Figure 27A:
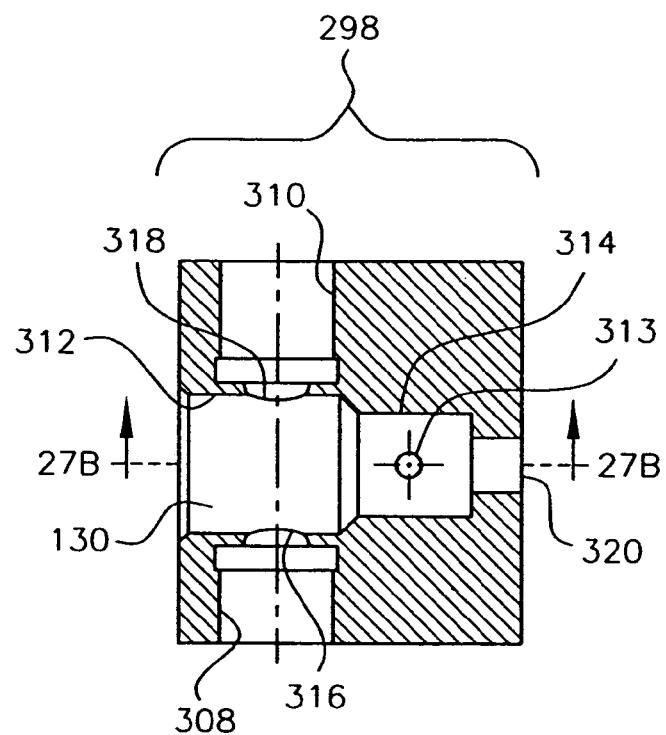
FIGS. 27A-27B provide views of an embodiment of a manifold adapted for use in the manifold assembly illustrated in FIGS. 26A and 26B.
Figure 27B:
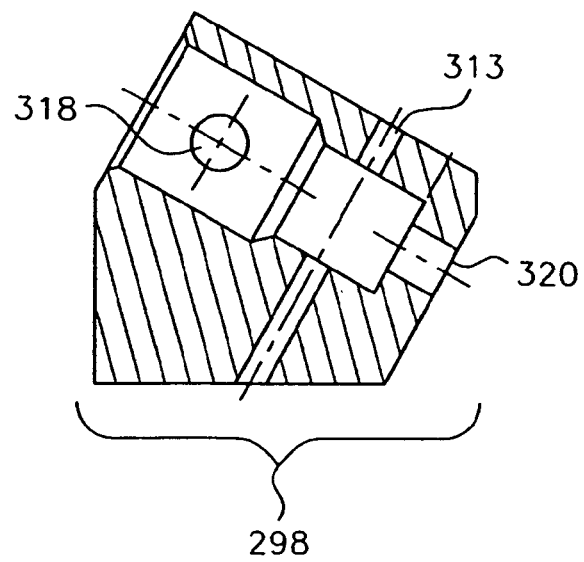

An opening (not shown) is provided in the wall of inlet fitting 242 at a location between o-ring grooves 266 and 268. This opening provides a vent for any water that may leak past one of the o-rings 244, 246. This vent helps to prevent any leaked water from entering the air line so that circulating water will not be delivered with the air to the patient. A port 313 in the manifold 298 (as shown in FIGS. 27A and 27B) provides a path for the flow of any leaked water out of the system so that it will not be entrained in the air supply that is delivered to the patient.

Also, inlet fitting 242 has a tubular inner extension 274 sized to fit within inner lumen 260 of inner tube 256 of tube 250 so as to create a seal between the outer surface of inner extension 274 and the inner surface of inner tube 256. Inlet fitting 242 is also provided with intermediate extensions 276A and 276B which are sized to extend within outer lumens 262 and 264 of extruded tube 250. More specifically, outer surfaces of intermediate extensions 276A and 276B form a seal against the inner surface of outer tube 254, and inner surfaces of intermediate extensions 276A and 276B are sized to create a seal with outer surfaces of inner tube 256. In other words, intermediate extensions 276A and 276B are configured for sealing engagement with first and second outer lumens 262 and 264.

A flow passage 282 is provided in intermediate extension 276A to permit fluid flow between an outer lumen of extruded tube 250 and the port 272A in inlet fitting 242. Similarly, a flow passage 284 is provided in intermediate extension 276B to provide such fluid flow between an outer lumen of tube 250 and port 272B. Inlet fitting 242 is also provided with an outer extension 278, wherein an inner surface of outer extension 278 is provided for sealing engagement with an outer surface of outer tube 254 of extruded tube 250. The outer surface of outer extension 278 is preferably provided with ridges or other surface treatments to facilitate the insertion of inlet fitting 242 into the manifold assembly 140 of the supply unit assembly 102 by a user. Such surface treatments can be selected to provide an ornamental appearance that identifies the manufacturer of the delivery tube assembly 104. The outlet fitting 252 can be provided with a matching surface treatment.

In order to facilitate insertion of an end of extruded tube 250 into inlet fitting 242, wherein outer tube 254 extends into a recess between outer extension 278 and intermediate extensions 276A and 276B, a pressure release opening 280 is provided to release trapped air upon assembly. A flow passage 286 extending along the axis of inlet fitting 242 is provided to permit gas flow from the supply unit assembly 102 into the inner tube 256 of extruded tube 250.

Inlet fitting 242 is also provided with a pair of opposed detents 243A and 243B. Detents 243A and 243B provide for orientation and locking engagement between inlet fitting 242 of delivery tube assembly 104 and supply unit assembly 102. Further details of this feature will be described later with reference to FIG. 28.

Although not shown, inlet fitting 242 can be provided with a radially extending flange about its circumference at a location adjacent to opposed detents 243A and 243B. Also, it should be noted that the configuration of the outer surface of inlet fitting 242 is provided with a combination of ornamental features and surface configurations. Such ornamental features provide the configuration of the inlet fitting 242 and the tubular assembly 104 with an ornamental appearance.

Figure 25A:
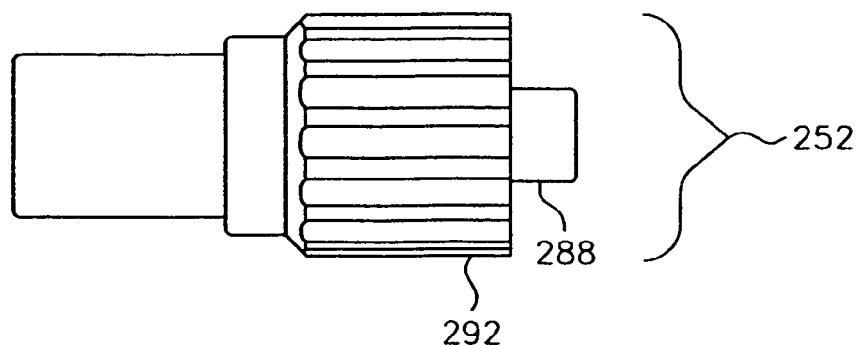
FIGS. 25A-25C provide views of an embodiment of an outlet fitting adapted for use in the delivery tube assembly illustrated in FIG. 22.
Figure 25B:
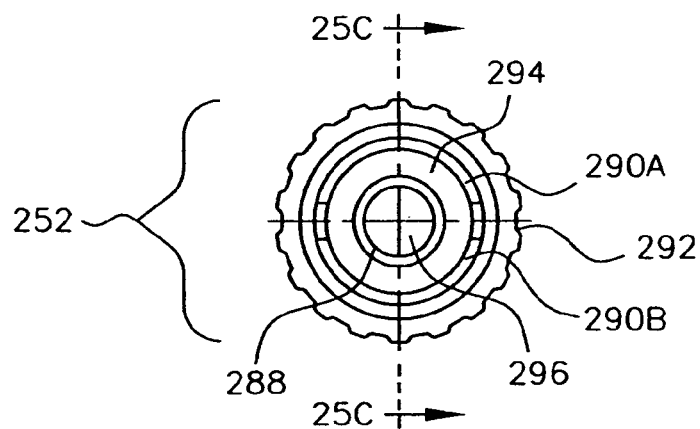
Figure 25C:
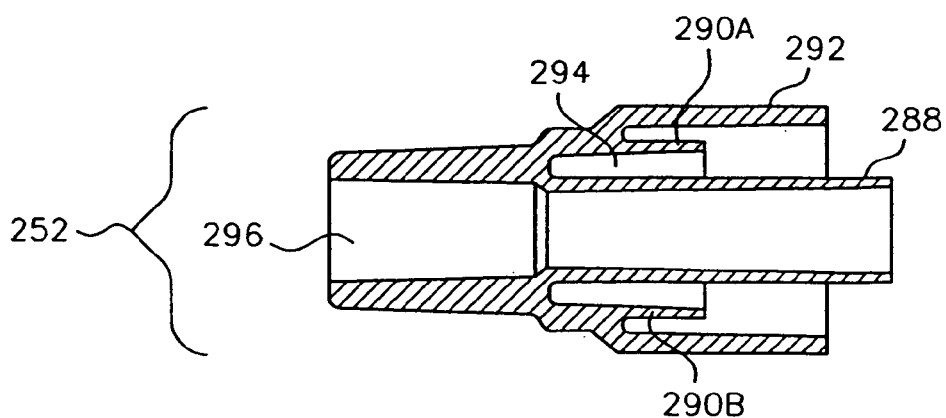

Referring now to FIGS. 25A through 25C, preferred features of outlet fitting 252 are illustrated. Referring specifically to FIG. 25C, outlet fitting 252 is provided with a tubular inner extension 288 sized to fit in a sealing manner within inner tube 256 of extruded tube 250. Outlet fitting 252 also includes semi-circular intermediate extensions 290A and 290B configured to extend within outer lumens 262 and 264 of extruded tube 250. Like extension portions 276A and 276B of inlet fitting 242, extensions 290A and 290B of outlet fitting 252 need not be dedicated to a particular outer lumen. Accordingly, during assembly of outlet fitting 252 and extruded tube 250, a particular one of extension portions 290A and 290B need not be mated to a particular one of outer lumens 262 and 264.

Outlet fitting 252 also includes a tubular outer extension 292 which is configured to provide sealing contact with an outer surface of outer tube 254 of extruded tube 250. As with outer extension 278 of inlet fitting 242, outer extension 292 of outlet fitting 252 can be provided with a surface treatment, such as the longitudinally extending ridges shown in FIGS. 24A and 25A, to facilitate connection of outlet fitting 252 to a nasal cannula. Surface treatments can also be applied to the outer surface of outlet fitting 252 as an indicator of the identity of the manufacturer or source of the delivery tube assembly 104.

Defined between intermediate extensions 290A and B and inner extension 288 is an annular recess 294 which is deeper than the recess between intermediate extensions 290A and 290B and outer extension 292. When extruded tube 250 is inserted into outlet fitting 252, annular recess 294 provides a passage for fluid flow communication of warming fluid between outer lumens 262 and 264 of extruded tube 250. In other words, when outer tube 254 of extruded tube 250 bottoms in the recess between intermediate extensions 290A and 290B and outer extension 292 of outlet fitting 252, a portion of annular recess 294 remains open, thereby providing an annular region for fluid flow between the first and second outer lumens 262 and 264 of the tubing. Outlet fitting 252 also includes a flow passage 296 through which gas can flow from the inner lumen 260 of extruded tube 250 to a cannula connected to outlet fitting 252 and for delivery of gas to the patient.

Although not shown, the outlet fitting 252 can be modified such that the flow passage 296 is shortened. Also, external features of the outlet fitting 252 provide the outlet fitting 252 with an ornamental appearance by virtue of a variety of surface contours and configurations.

Figure 26A:
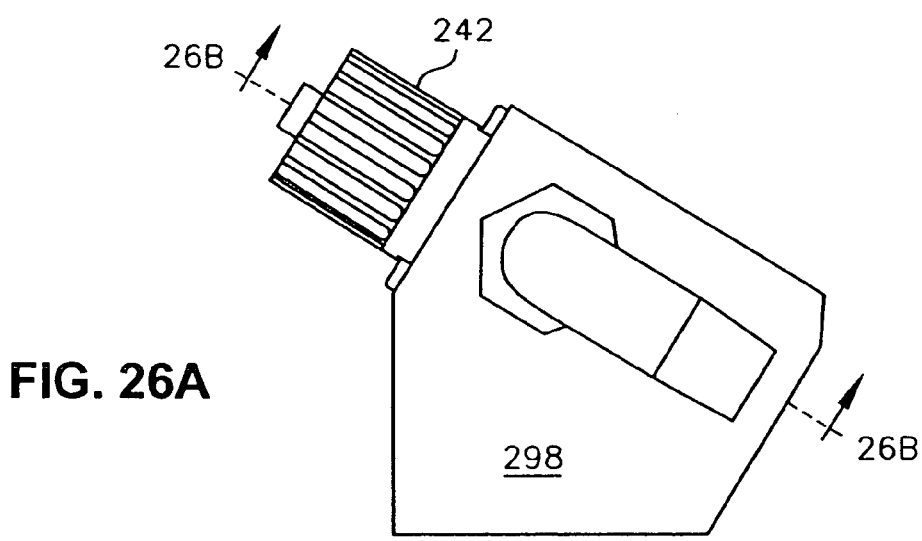
FIGS. 26A-26B provide views of the manifold assembly illustrated in FIG. 17.
Figure 26B:
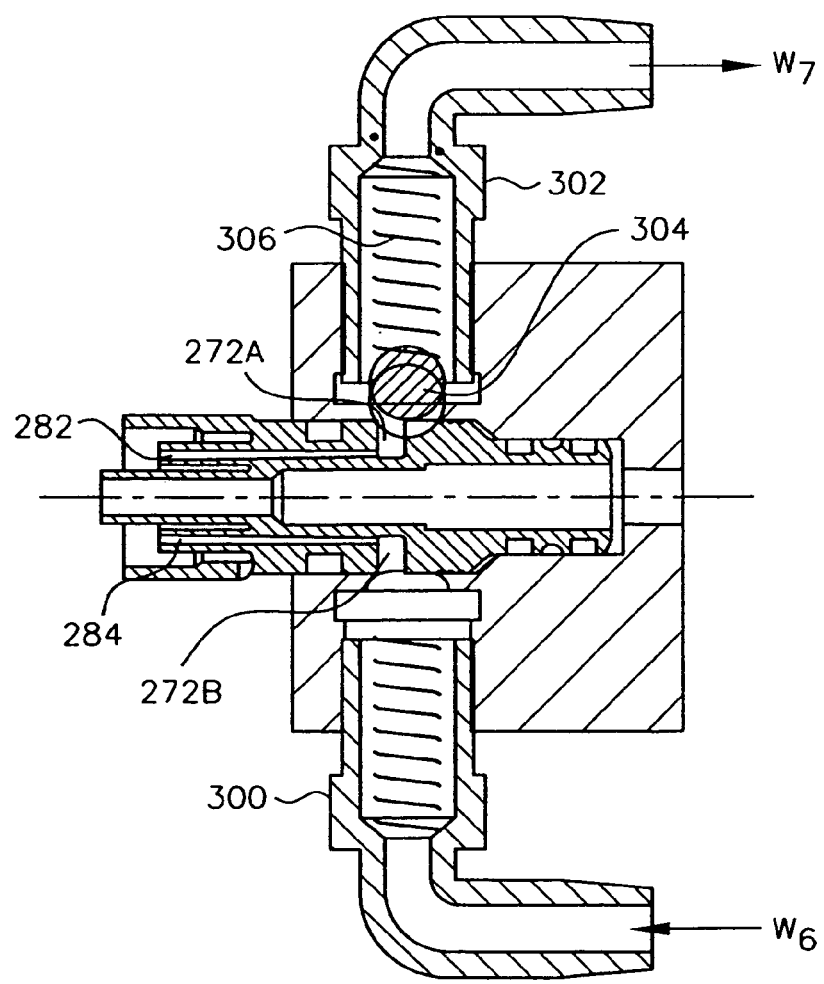

FIGS. 26A and 26B illustrate preferred features of manifold assembly 140 with inlet fitting 242 of delivery tubing assembly 104 inserted therein. As is best illustrated in FIG. 26B, water "W" is introduced into a manifold block 298 through an inlet assembly 300, which includes an elbow fitting. Water then enters port 272A (or 272B) for flow into and through flow passage 282 (or 284) in inlet fitting 242. The heated water then flows through an outer lumen 262 (or 264) of the delivery tube 250, flows through the recess 294 in outlet fitting 252, and returns through an outer lumen 264 (or 262) of the delivery tube 250. The water then flows through flow passage 284 (or 282) in inlet fitting 242 to port 272B (or 272A). Water then flows outwardly from manifold block 298 through an outlet assembly 302. As described previously, the orientation of delivery tube assembly 104 within manifold assembly 140, and the orientation of extruded tube 250 with respect to inlet fitting 242, determine the direction of flow through the ports of inlet fitting 242 and the outer lumens of the delivery tube 250.

In this embodiment, outlet assembly 302 includes a ball valve including a ball 304 and a spring 306. It will be understood that spring 306 biases ball 304 against the flow opening when the delivery tube assembly 104 is not connected to the port 130 of manifold assembly 140. Accordingly, the ball valve provided by ball 304 and spring 306 prevents leakage of water from the supply unit assembly upon removal of the delivery tube assembly 104 from the manifold. A corresponding ball valve is also provided in inlet assembly 300 in order to prevent the leakage of water (or other heating fluid) from the system when the delivery tube assembly is not in place.

Referring now to FIGS. 27A and 27B, block manifold 298 defines port 130 as well as ports for inlet assembly 300 and outlet assembly 302. More specifically, as is illustrated in FIGS. 27A and 27B, the single port 130 of manifold 298 provides an outlet opening 316 for the flow of heating fluid such as water from the supply unit assembly 102. Outlet opening 316 permits flow of heating fluid from the supply unit for delivery into delivery tube assembly 104 via port 272A or 272B in inlet fitting 242 of assembly 104 (depending upon the rotational orientation of inlet fitting 242 within manifold 298).

Port 130 also provides an inlet opening 318 for the return flow of heating fluid such as water into the supply unit assembly 102 for recirculation. Inlet opening 316 permits flow of heating fluid from delivery tube assembly 104 into the supply unit via port 272A or 272B in inlet fitting 242 of assembly 104 (depending upon the rotational orientation of inlet fitting 242 within manifold 298).

Port 130 also provides an outlet opening 320 for the flow of heated and humidified air from the supply unit 102. Outlet opening 320 permits flow of air from the supply unit into delivery tube assembly 104 via passage 286 in inlet fitting 242.

Accordingly, it will be appreciated that air and water delivery from the supply unit, as well as water return to the supply unit, are accomplished by means of a single port (such as port 130) in the supply unit. It will also be appreciated that air and water can be received into the delivery tube assembly, and that water can be delivered from the delivery tube assembly, by means of a single fitting (such as inlet fitting 242) in the delivery tube assembly. These preferred features of the invention facilitate rapid, accurate, and predictable connection between the delivery tube assembly and the supply unit assembly. In other words, only a single delivery tube inlet fitting need be inserted into a single supply unit port in order to establish water and air flow connections.

Manifold 298 is provided with female pipe threads 308 for engagement of inlet assembly 300. Manifold 298 is also provided with female pipe threads 310 for engagement of outlet assembly 302.

Port 130 of manifold 298 includes a portion 312 having a larger diameter as compared to a portion 314 with a small diameter. O-ring 248 of inlet fitting 242 provides a fluid-tight seal against the inner surface of large diameter region 312. O-rings 244 and 246 of inlet fitting 242 provide for fluid-tight seals against inter surfaces of smaller diameter region 314.

Figure 28:
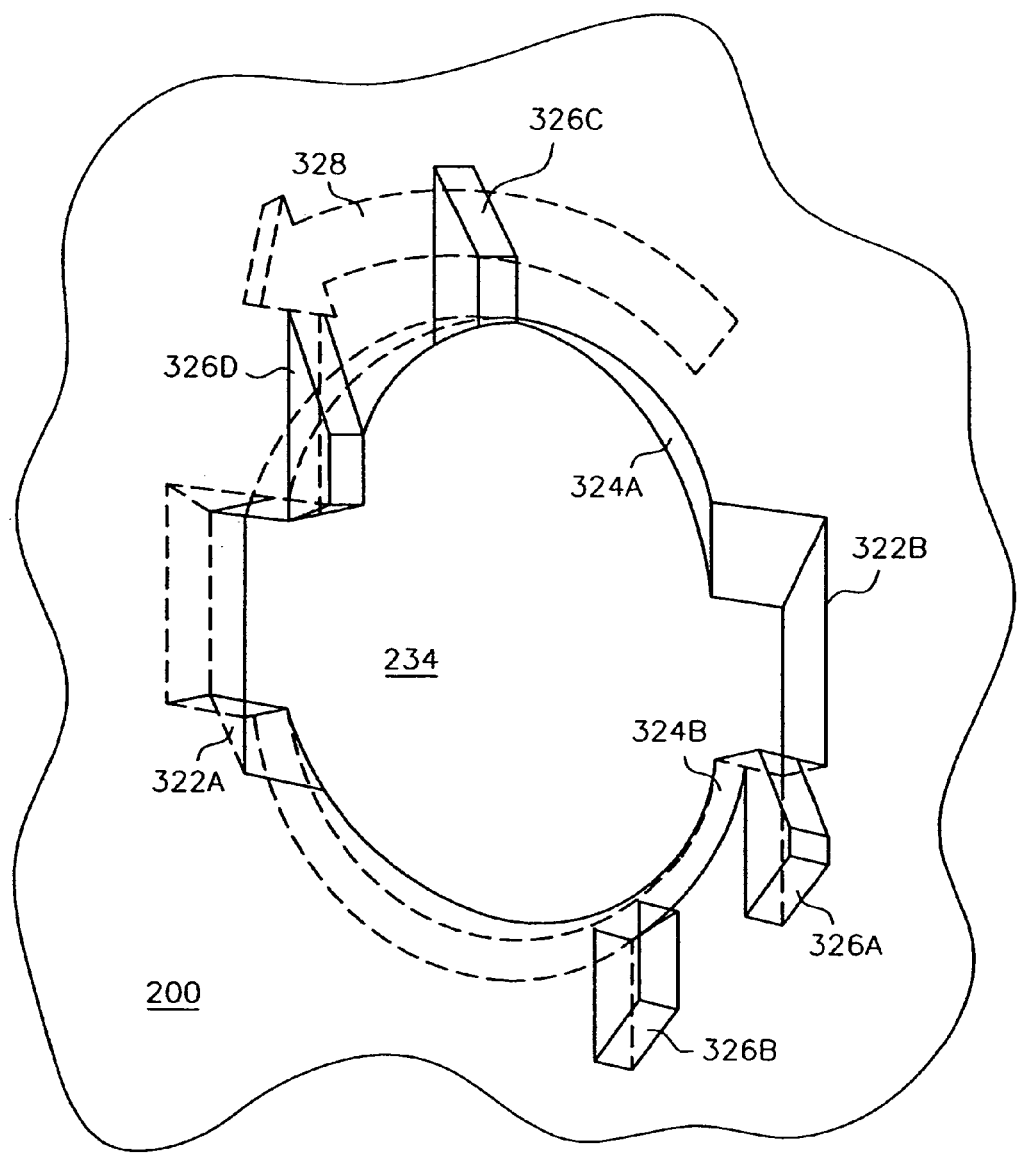
FIG. 28 illustrates an embodiment of a locking mechanism adapted for use with the apparatus according to this invention.

Referring now to FIG. 28, which provides a cut-away view of a portion of main housing component 200, a preferred locking arrangement for locking assembly 104 to assembly 102 is illustrated. Specifically, opening 234 of housing component 200 is provided with a pair of opposed recesses 322A and 322B, which are sized and positioned to receive the detents 243A and 243B of inlet fitting 242. Opening 234 is also provided with a pair of ramps 324A and 324B, each of which extends from one of the recesses 322A and 322B.

Also, a series of four detents 326A-326D are provided on a surface of component 200 adjacent opening 234. Detents 326A-326D are positioned to provide stops to limit the rotation of fitting 242 with respect to the manifold. More specifically, detents 326A-326D are contacted by detents 243A and 243B upon rotation. The arrow 328 in FIG. 28 indicates a direction of rotation for engaging fitting 242 in manifold 298. Although counterclockwise rotation for engagement is illustrated in FIG. 28, it is actually preferred for rotation to be clockwise for engagement, as is described later. To accomplish clockwise rotation for engagement, the mirror image of FIG. 28 can be employed.

Upon insertion of fitting 242 within opening 234 and rotation of fitting 242 counterclockwise, detents 243A and 243B of inlet fitting 242 will stop after about a quarter turn upon contact with detents 326B and 326C. Detents 326B and 326C are also positioned to orient fitting 242 rotationally with respect to manifold 298 so as to provide alignment of ports 272A and 272B of inlet fitting 242 with ports 316 and 318 of manifold 298. Arrow 328 can be provided on a surface of housing component 200 in order to indicate a direction of rotation to engage the fitting 242 within the manifold 298.

In order to release fitting 242 from the opening 234 illustrated in FIG. 28, the fitting 242 is rotated in the clockwise direction until detents 243A and 243B contact detents 326A and 326D. Upon such contact, detents 243A and 243B are aligned with recesses 322A and 322B so that the fitting 242 can be extracted from the opening 234.

It will be appreciated that a locking structure such as the one illustrated in FIG. 28 can provide a quarter-turn, bayonet-style locking engagement between the fitting and the supply unit. Such a connection provides a reliable, one-step procedure for connecting the delivery tube assembly.

The general flow of heating fluids such as water W and therapeutic gas such as air A through the apparatus 100 will now be described with reference to FIGS. 11A, 11B, 15A, 15B, 16, 17, 26A, and 26B. Reference can also be made to the schematic diagram provided in FIG. 9.

Figure 9:
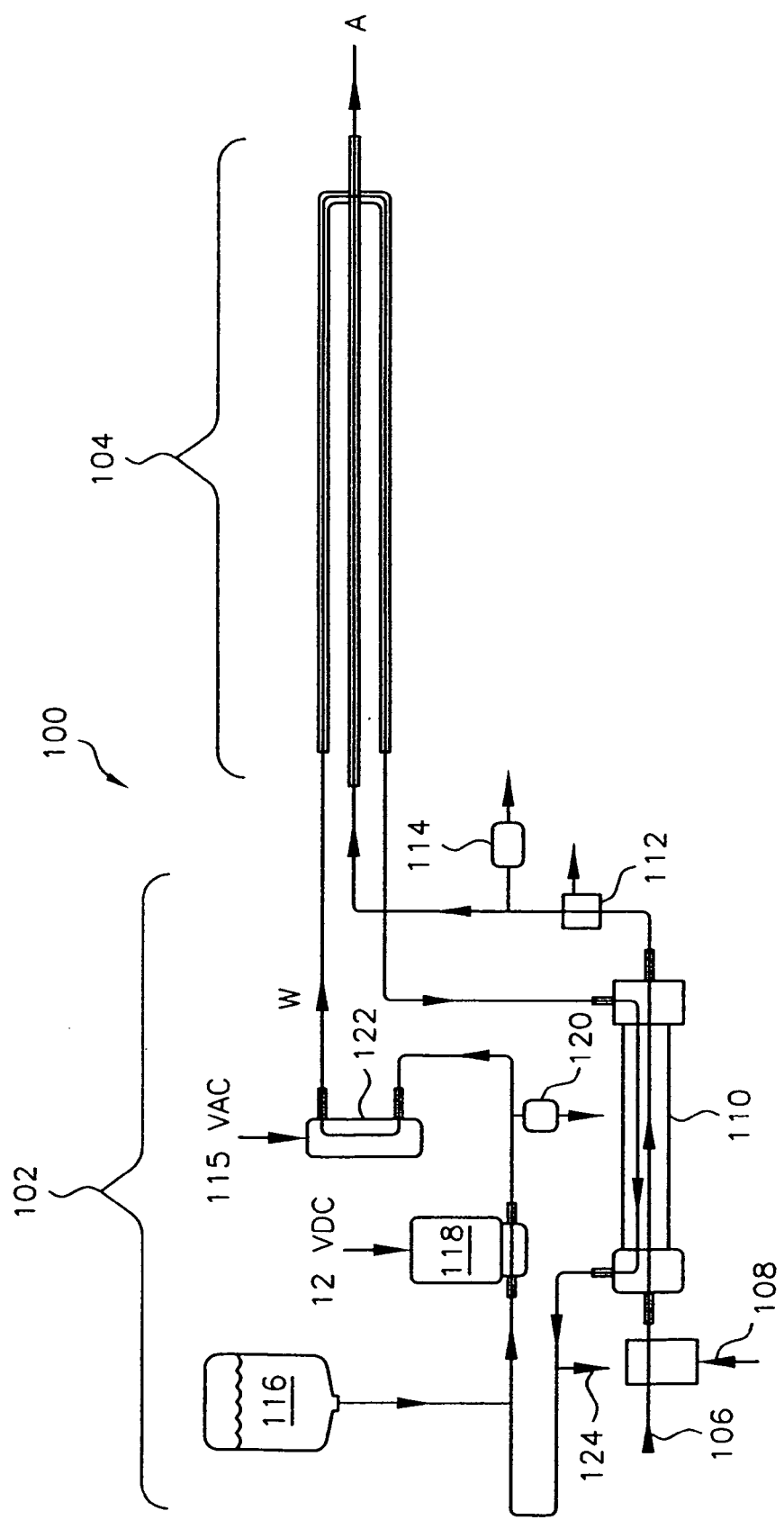
FIG. 9 is a schematic representation of another embodiment of an apparatus according to aspects of this invention.

Referring first to the flow of water W through apparatus 100, water $W_1$ is introduced into apparatus 100 via bubble trap assembly 150 from a water source such as a water bag. Water $W_2$ flows outwardly from bubble tube assembly 150 and into water pump 190. Water $W_3$ then flows out from water pump 190, and water $W_4$ then flows into water heater 192 for heating. Water $W_5$ flows outwardly from water heater 192, and water $W_6$ then flows into manifold assembly 140 through inlet assembly 300. After flowing through delivery tube assembly 104 and returning to supply unit assembly 102, water $W_7$ flows outwardly from manifold assembly 140 through outlet assembly 302. The water $W_7$ then flows into an elbow for delivery as water $W_8$ into the membrane cartridge 110 (FIG. 9). Water $W_9$ flows outwardly from cartridge 110 and into bubble trap assembly 150. The water is then recirculated as water $W_2$ through apparatus 100, together with additional water $W_1$ received from water bag 116 (FIG. 9).

Regarding the flow of air A through apparatus 100, air $A_1$ is introduced into the apparatus from a source into inlet port 152. Air $A_2$ then flows to exchanger 110 (FIG. 9) for humidification by means of the transfer of water vapor. Air $A_3$ then flows from exchanger 110 into elbow 142. Air $A_4$ is then directed into manifold assembly 140 for delivery into the delivery tube assembly and to the patient.

Delivery tube assembly 104 can be easily and efficiently connected to supply unit assembly 102 by simply inserting an end of inlet fitting 242 into the port 130 of supply unit assembly 104, as will be described in further detail later. Accordingly, this simple insertion provides fluid flow communication between the supply unit and the delivery tube for the flow of gas from the supply unit toward the patient. Simultaneously, insertion of inlet fitting into port 130 provides fluid flow communication for warming fluid, such as water, which can then flow from the supply unit into the delivery tube and return from the delivery tube into the supply unit in a leak-free environment.

Also, it is significant to note that the interconnection between inlet fitting 242 and port 130 provides for an axially extending flow passage for gas from supply unit assembly 102 into the inner tube of the delivery tube assembly 104. Also, at the opposite end, an axial gas flow passage is provided for flow from the inner tube of the delivery tube into the outlet fitting and from the outlet fitting into a nasal cannula. The provision of such axial flow passages has been discovered to provide a reduction in pressure drop as the gas flows from the supply unit through the delivery tube to the patient.

In use, the apparatus in this embodiment is adapted to be clamped to a standard IV pole or hanger; ideally, it should be mounted at approximately the same height as the patient's head although a range of about four (4) feet above or below this level should be acceptable. After the apparatus is clamped to the IV pole or hanger and the power cord is plugged in, the water reservoir is then filled. If the water supply has a high mineral content, distilled water can be used. Otherwise, tap water is acceptable. The reservoir tube is connected to the apparatus in order to provide fluid flow into the apparatus.

The delivery tube is then connected to the port on the apparatus. In order to do so, the delivery tube connector is pressed firmly into the connection port and rotated ¼ turn clockwise (preferably) until it locks in place.

The power for the apparatus is then switched on and the temperature setting is adjusted by pressing and holding an arrow to display the set temperature. The up and down arrows are used to change the setting. Upon the release of the arrow, the actual temperature is displayed for all temperatures up to about 45° C. At higher temperatures, the display can read "HI".

A nasal cannula is then connected to the opposite end of the delivery tube, and the wall source of air, oxygen or a blend is connected to the inlet port of the apparatus. Using an external flow regulator, the flow rate of the air, oxygen or blend can be adjusted to a desired setting such as a setting between about 20 and about 40 lpm for adults, for example.

After the apparatus has reached operating temperature, wherein the temperature indicated on the front panel of the apparatus equals the set temperature, the nasal cannula is fit to the patient. A periodic check for alarm conditions may be made. However, the apparatus may be configured to shut down if temperature safety limits are exceeded or if the water level is low.

The delivery tube should be changed for each patient. To do so, the base of the delivery tube is rotated ¼ turn (preferably counter-clockwise) and pulled straight down (when the apparatus is mounted on the IV pole). A connector of a new delivery tube is then inserted in the receptacle by pressing it firmly in place and rotating it a ¼ turn (preferably clockwise) to lock it in place.

The humidifier cartridge can be changed periodically. In order to do so, the water reservoir is disconnected from the apparatus and the cover to the cartridge chamber is opened. Water and air tubes from the cartridge are disconnected and reconnected to a new cartridge. The new cartridge is then pressed into place and the cover is closed.

In order to clean the apparatus, the delivery tube can be removed and a drain tube can be inserted so that the water in the apparatus can be drained. The delivery tube is then replaced. A bag of cleaning solution can then be connected to the apparatus and the apparatus can be turned on in order to circulate the cleaning solution without heating. The power can then be shut off and the apparatus can be drained of cleaning solution, and the delivery tube can be discarded. The cleaning solution bag is then removed and replaced with a water bag. A new delivery tube is then fit into place, and the apparatus is again ready for use.

Figure 38:
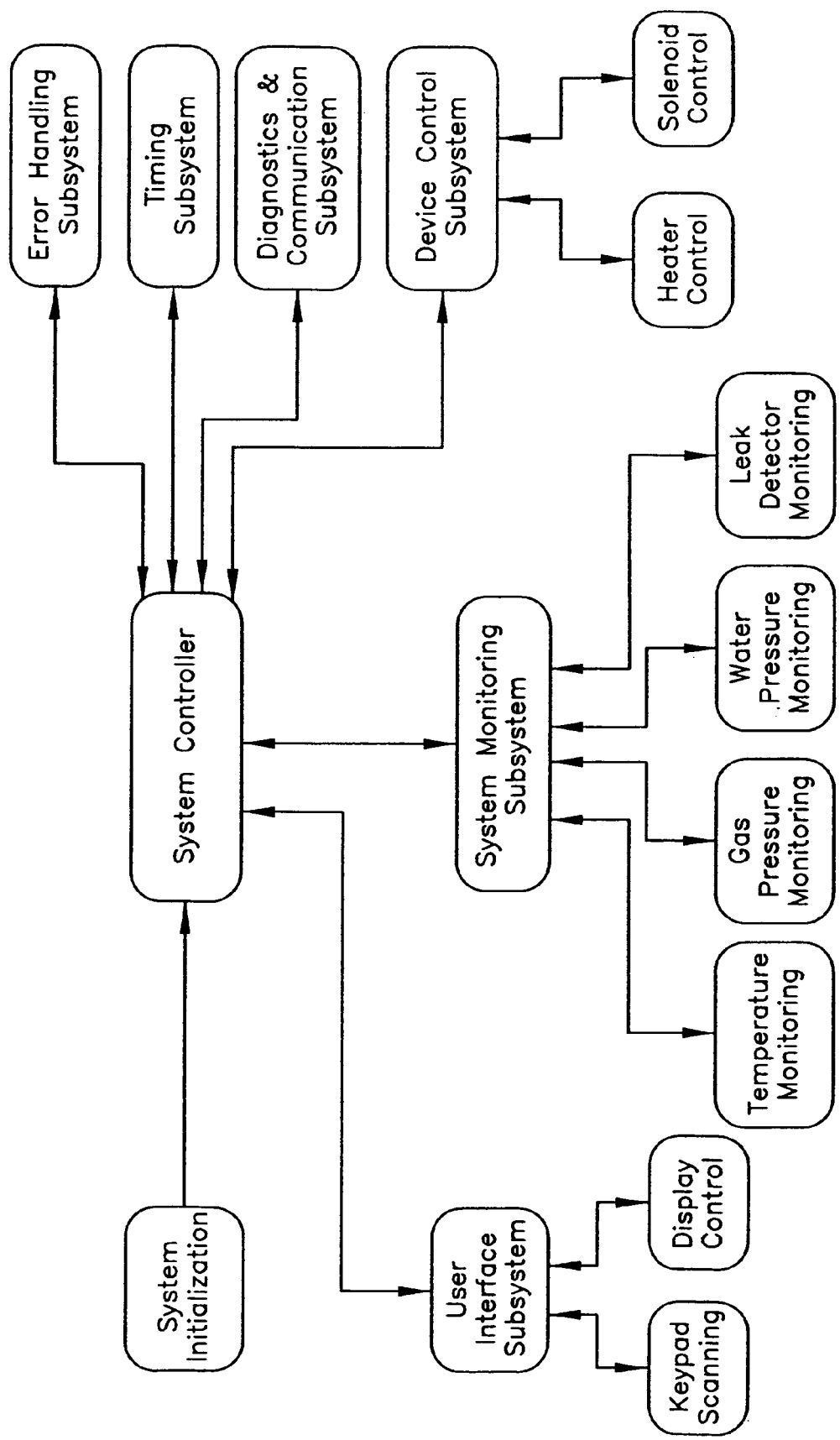
FIG. 38 provides a diagram of an embodiment of a system according to this invention.
Figure 39:
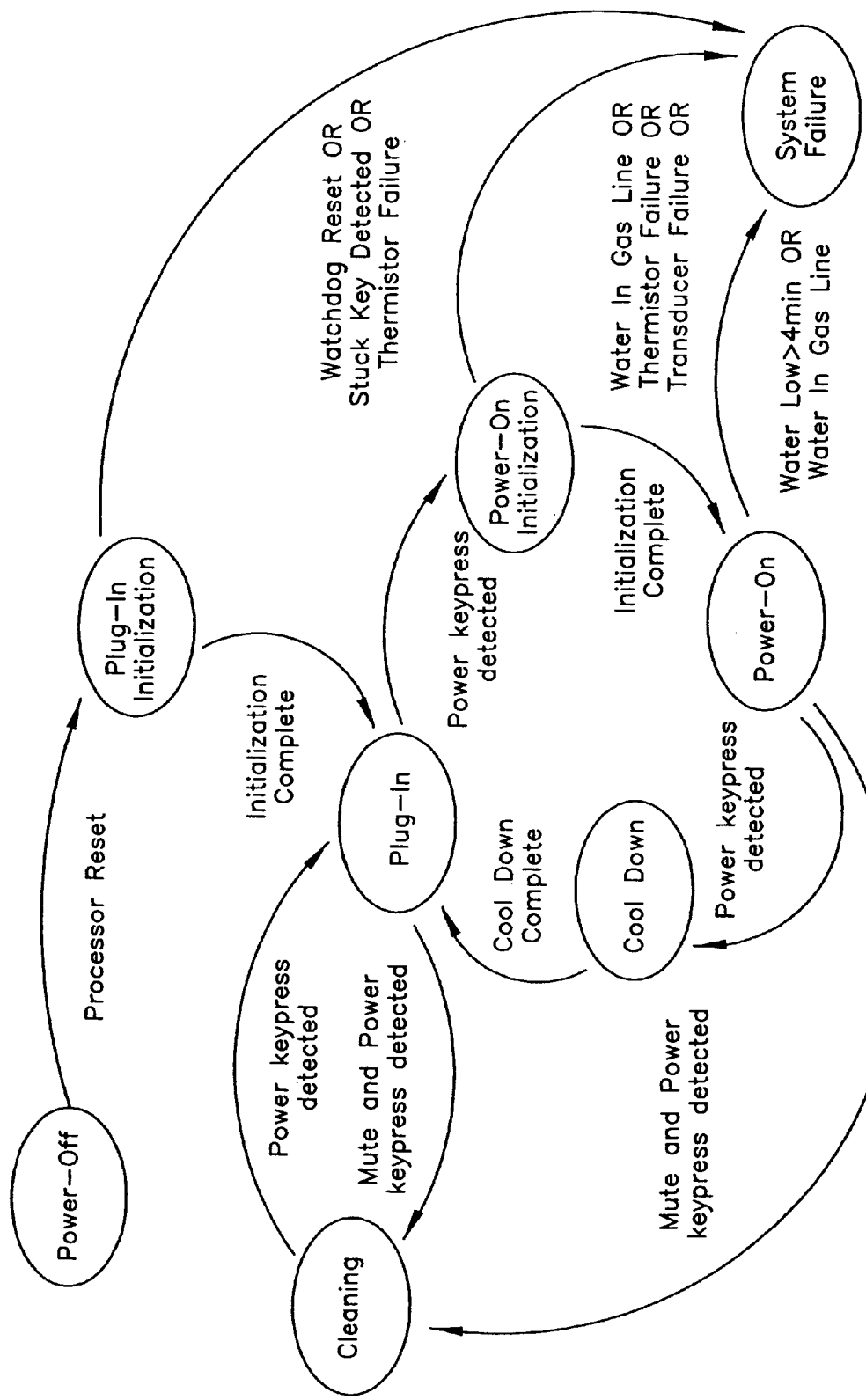
FIG. 39 provides another diagram representing the system illustrated in FIG. 38.
Figure 40A:
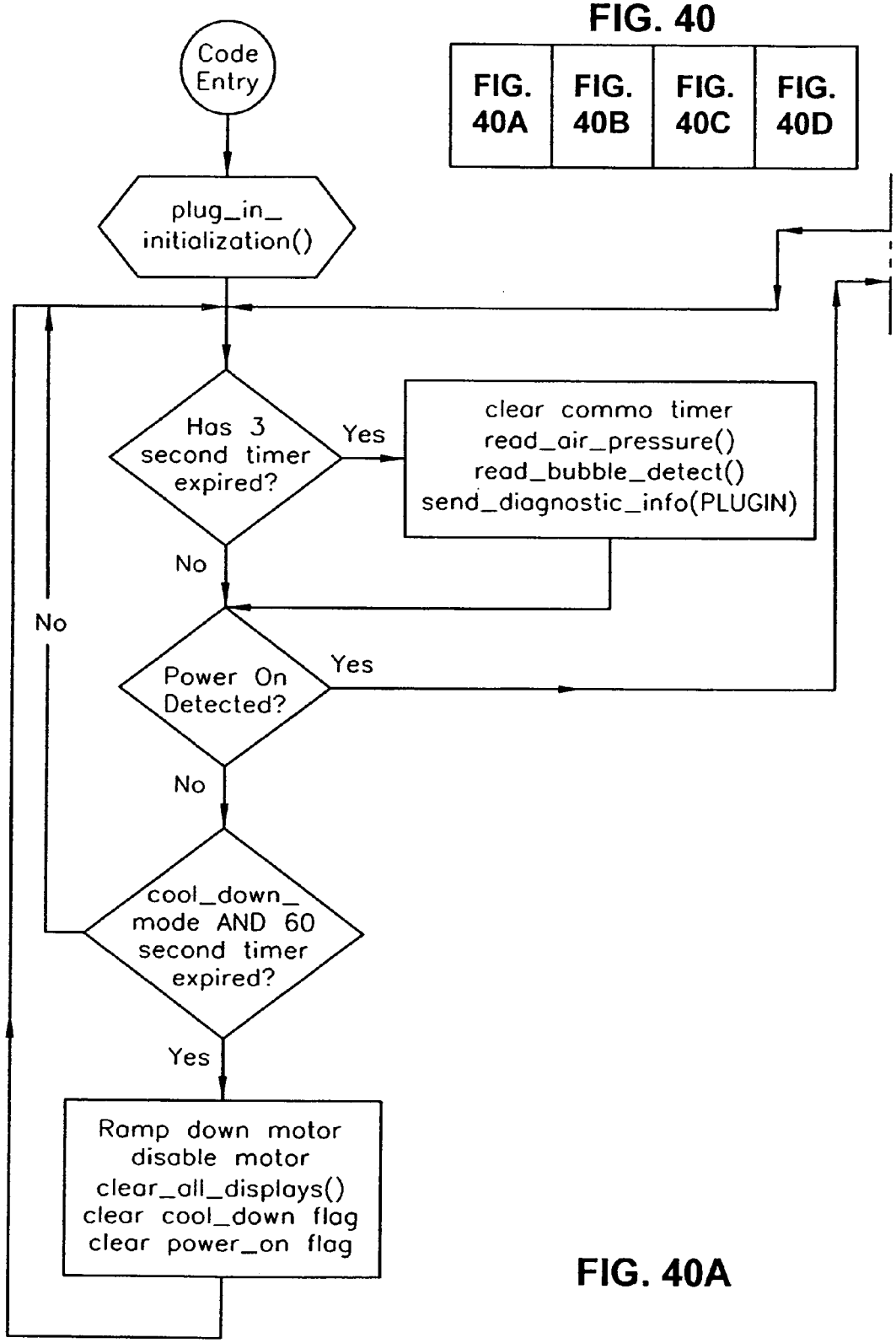
FIG. 40A provides a first portion of a flow diagram of an embodiment of software adapted for use with the apparatus according to the invention.
Figure 40B:
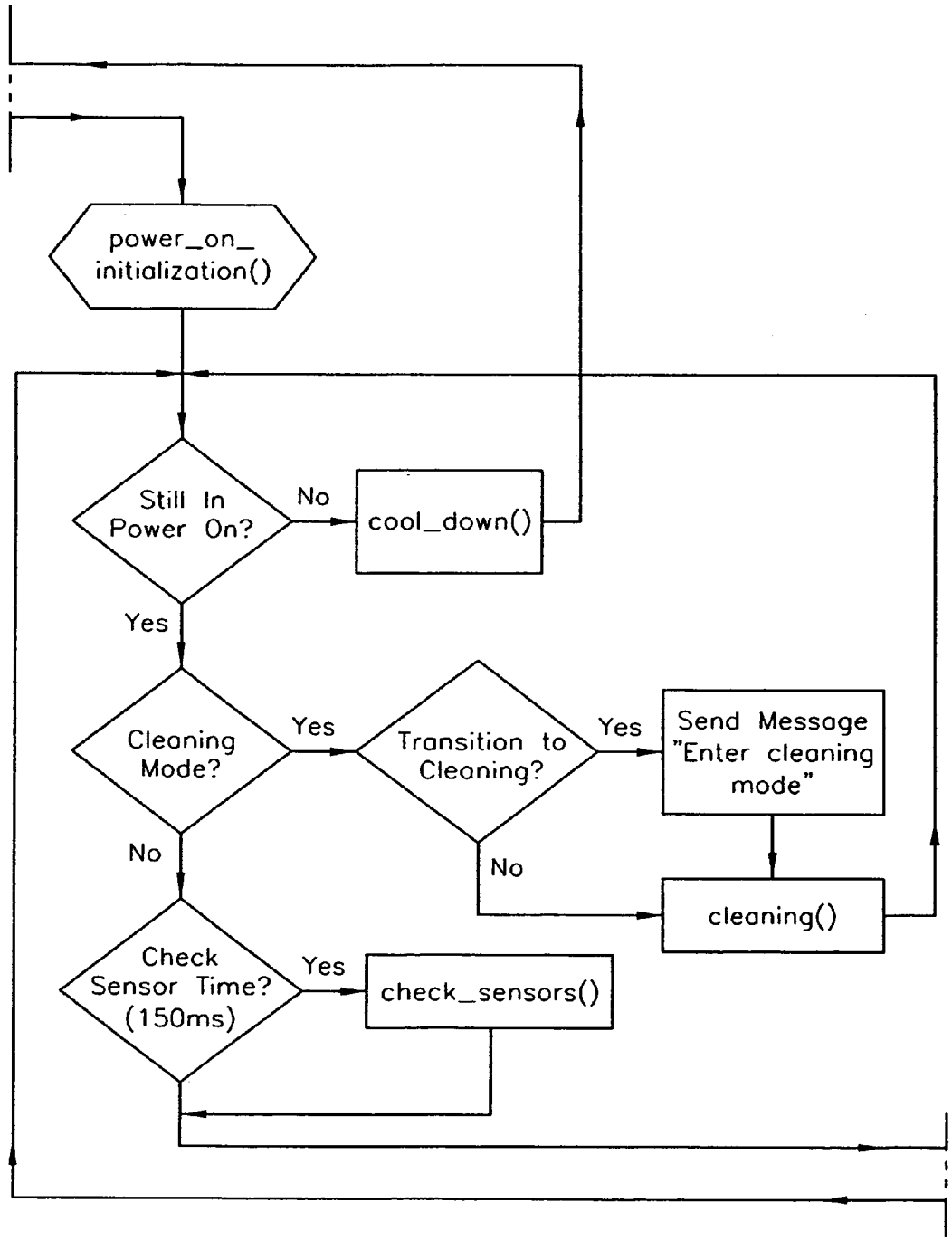
FIG. 40B is a continuation of the flow diagram of FIG. 40A.
Figure 40C:
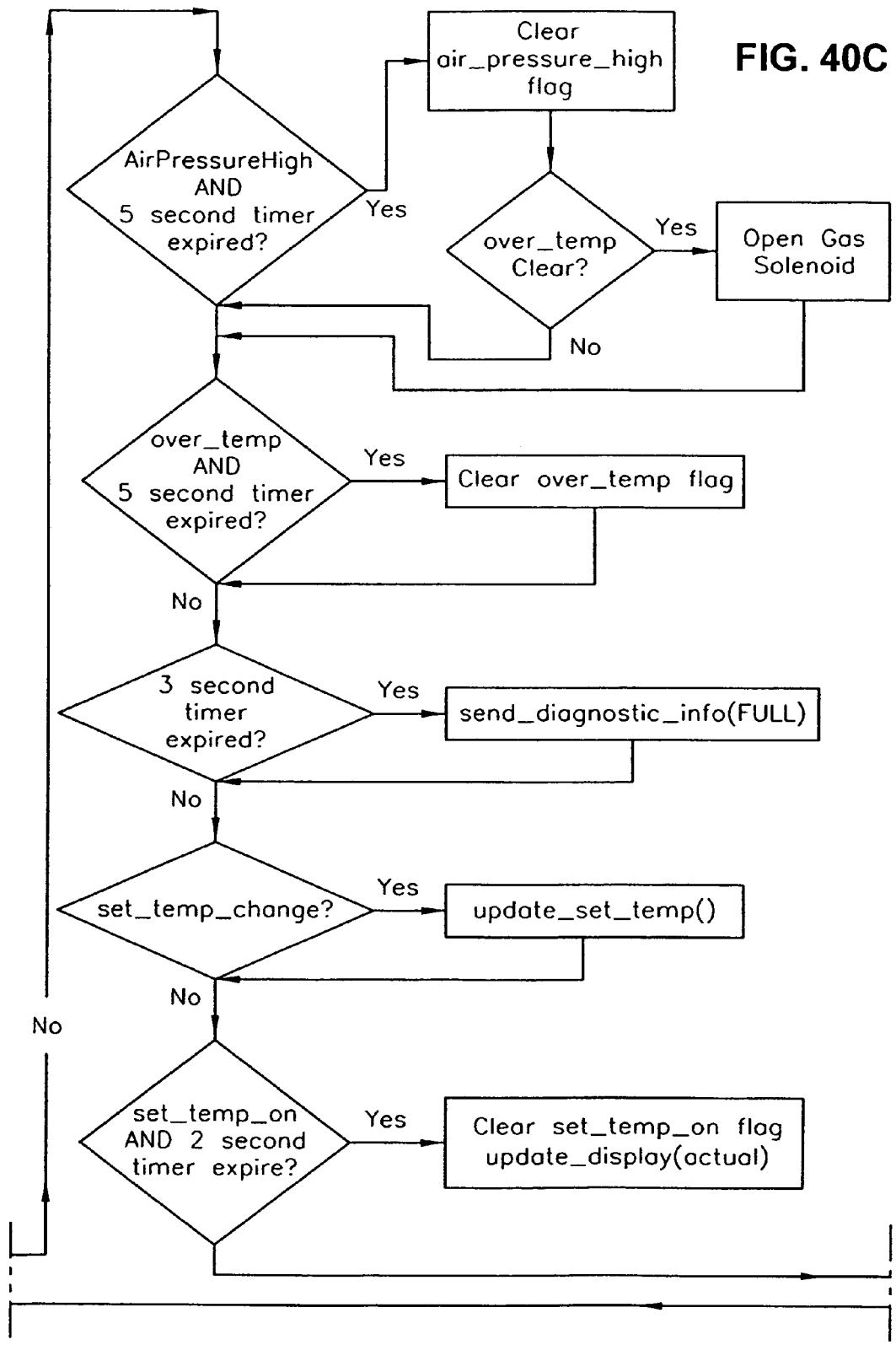
FIG. 40C is a continuation of the flow diagram of FIG. 40B.
Figure 40D:
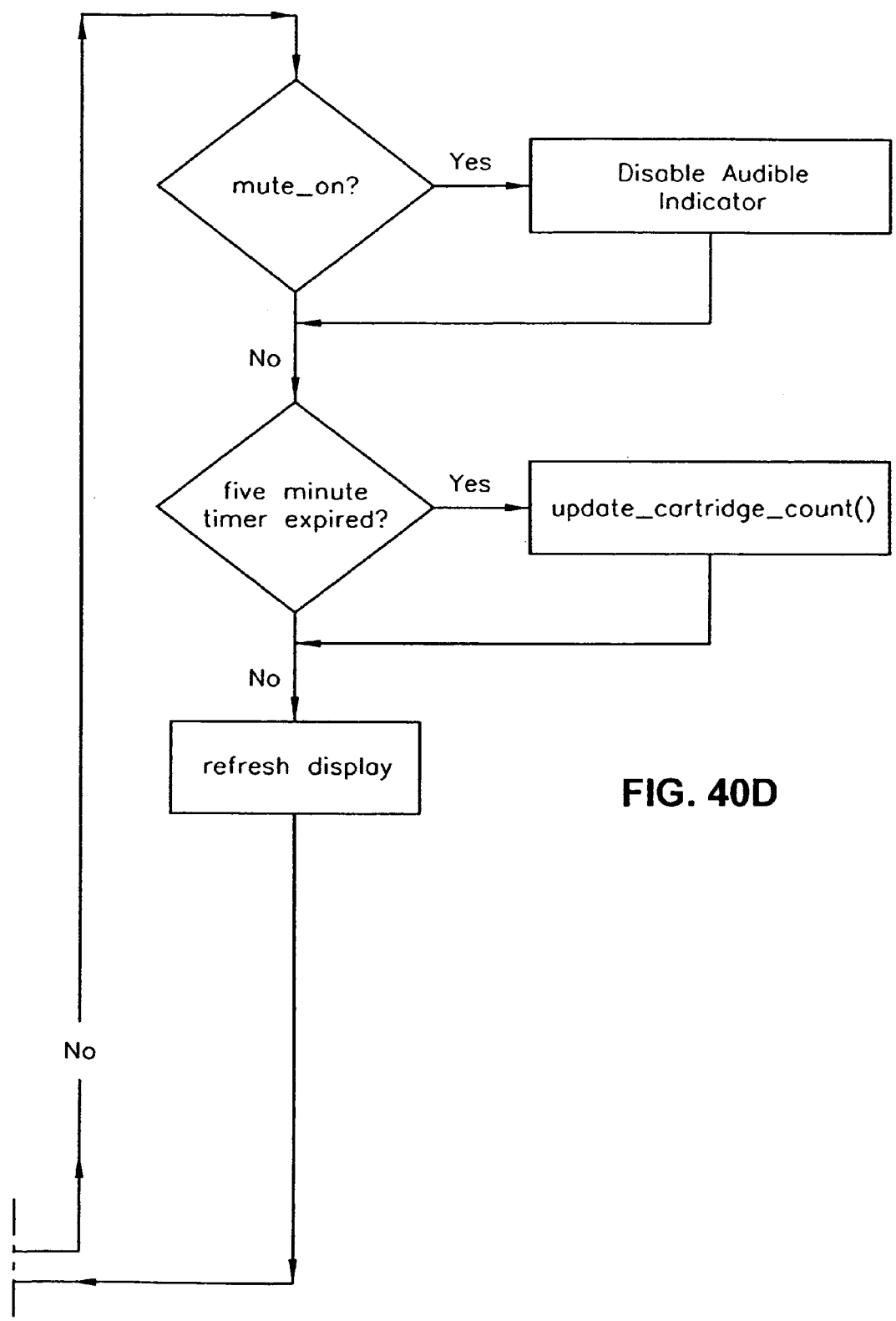
FIG. 40D is a continuation of the flow diagram of FIG. 40C.

Referring now to FIGS. 38, 39 and 40A-40D, a functional overview of a preferred embodiment of the system will now be described. Referring to FIG. 38, the software that supports the system is divided into functional areas or logical "modules" which provide specific related functionality. A System Initialization module is responsible for the correct initialization of the system at power up. This section of the software executes whenever the processor is reset. A System Controller module is the code that executes after system initialization or plug-in. The Timing Subsystem module provides overall system timing. The Diagnostics and Communication Subsystem module is responsible for formatting system parameters into human readable form and transmitting this data to a terminal. The Device Control Subsystem module provides facilities for the control of the gas solenoid and heater. The Error Handling Subsystem module provides functions to monitor the various system parameters and the required logic to initial the appropriate error handling response. The User Interface Subsystem module provides keypad scanning and display control. Finally, the System Monitoring Subsystem module implements routines for reading system sensors.

Referring now to FIGS. 39 and 40A-40D, plug-in initialization is performed when a processor reset occurs. After successful of plug-in initialization, the system enters the plug-in state. When a power key press is detected, and the system transitions to power-on initialization. Following successful completion of power-on initialization, the system enters the power-on state—this is the main operating state of the instrument during which the humidification process occurs. When a power-on/off key press is detected during power-on, the system will transition to a cool down mode. When the power-on/off and mute keys are simultaneously depressed, the cleaning mode flag is set and the system enters cleaning mode. Finally, when the system encounters an unrecoverable error, it enters system failure mode.

A flow diagram illustrating one preferred embodiment of software adapted for use with this invention is illustrated in FIGS. 40A-40D.

The apparatus in this embodiment confers several significant advantages. The apparatus is capable of producing a high flow of highly humidified air (relative humidity greater than 95%), virtually free of droplets, at body temperature or above. The water content at 41° C. is about 40-50 mg/liter, which is about four times higher than can be achieved by humidification at room temperature. Because the water is almost all in the vapor phase, there is little or no impaction of water droplets in the upper airway of the patient, and the vapor content is available to the entire pulmonary airway. Heating of the air delivery tube using circulating hot water maintains a substantially constant temperature between the apparatus and the patient, thereby avoiding condensation when the air is delivered with high water content.

Unlike conventional humidifiers, which may rely on either evaporation from a liquid surface or on aerosolization of water, the apparatus according to this invention need not have any direct interface between water and air. Instead, the apparatus humidifies by diffusion of water vapor through a microporous membrane into a flowing air stream. The membrane pore size, which is preferably less than about 0.1 micron, excludes particles so that the output air is substantially free of bacteria, viruses and most allergens.

The casing protects electrical components from accidental water spills. Also, it is preferred that all external parts of the apparatus have a service temperature not exceeding about 41° C. The system and apparatus are preferably protected against overheating by software that monitors water temperature. Specifically, an alarm sounds if the temperature rises above the set point. Also, the apparatus is preferably shut off if the temperature continues to increase.

In order to maintain bacteriological safety, air and water are preferably separated by a biological barrier so that, even if the water circulation should become colonised by bacteria, the air would remain substantially sterile. In order to prevent circulating water from entering the air tubing and being forced toward the patient's airway, the presence of liquid water in the air tubing can cause an instant shut down of the unit.

Treatment of Respiratory Tract Conditions

The apparatus according to this invention has been discovered to confer significant and surprising benefits when used for the treatment of the respiratory tract or for respiratory tract therapy. The apparatus has been discovered to be uniquely adapted for the introduction of heated and humidified air to the respiratory tract of a human patient. The portability of the apparatus has made it easily adaptable for home use as well as for clinical use such as in the hospital setting.

It has been recognized that rhinitis, or the inflammation of the soft tissues in the nasal airway, can be caused by viral infections such as the common cold and influenza, and by allergies. Rhinitis can also be caused by failure of the nasal defense system as the result of, for example, cystic fibrosis. The nasal defense system essentially includes a "conveyer belt" formed by a layer of mucus, which traps particles such as bacteria. Tiny cilia hairs on the cells of mucous membrane move the mucus with trapped particles to the back of the nose where it enters the throat and is swallowed. If this "conveyer belt" fails because the mucus is insufficient or too thick or if the cilia do not "beat" correctly, bacterial infection and inflammation can result.

It has been discovered that the introduction of heated and humidified air into the respiratory tract helps to treat rhinitis by thinning of mucus, which leads to improved secretion clearance. Also, high humidity promotes the healing of inflamed mucus-producing and ciliated cells. Also, high temperature (up to 42° C.) is believed to reduce the rate of viral replication. Accordingly, breathing of heated and humidified air has been discovered to be a beneficial treatment for many types of rhinitis.

The introduction of heated and humidified air, by means of an apparatus according to this invention for example, has been discovered to provide several unique advantages as compared to conventional humidifiers in connection with the treatment of rhinitis and other respiratory tract conditions. For example, the apparatus of this invention prevents contact between bulk water and air so that water-borne pathogens cannot enter the airflow. Also, by use of an apparatus according to this invention, water is present in the output air only as vapor in the virtual absence of aerosol particles so that particle deposition in the airway is minimized.

It has been discovered that the use of a temperature-controlled delivery tube according to this invention ensures that saturated air is delivered to the nose at body temperature or higher without heat loss or condensation, and a high flow rate of heated and humidified air ensures that almost all of the air breathed by a patient is heated and humidified with little or no entrained room air. All these benefits can be accomplished according to this invention by delivering air through a nasal cannula so that the patient can continue normal activities with minimal interference.

It has also been discovered that the treatment method according to this invention provides improved relief to people who suffer from asthma. Conventionally, asthma sufferers are recommended to keep humidity low because dust mites are more common in moist environments. Accordingly, the system according to this invention provides the benefits of warm humid air in the entire respiratory tract without the problems associated with high ambient humidity.

Despite intensive research, asthma remains a serious and growing public health problem. Asthma is not considered to be curable, and the treatment of asthma consists largely of attempts at control. The process underlying asthma appears to be inflammatory leading to hyper-reactivity of the airways when they constrict in response to a variety of stimuli. Although inhaled medications have been proposed to reduce inflammation (e.g. steroids) and to relax the bronchial smooth muscle directly (e.g. β-adrenergic agonists), there have been concerns raised over abuse of the medications and the side-effects associated with such medications. For this reason, a treatment is needed that can help control the symptoms of asthma without the risks and side-effects of the drugs in present use.

It has been discovered that a supply of room air saturated with water vapor at about 40° C. directly to the airway via a nasal cannula, thereby avoiding problems of condensation and cooling associated with conventional delivery of humidified air, reduces nasal irritation by eliminating drying and cooling of the nasal mucosa and pharynx, and is therefore therapeutic for asthma and rhinitis. More specifically, in a preferred treatment method, a patient is fit with a nasal cannula, and air is delivered to the patient at a flow rate of up to about 20 liters or more per minute at about 40° C., wherein the air is about 100% humidified.

EXAMPLE 1

An evaluation was conducted to determine the impact of breathing air at or above body temperature and saturated with water vapor on pulmonary function in asthmatics with rhinitis. Part of the bronchoconstriction occurring in asthmatics with rhinitis is believed to driven by a nasopulmonary reflex stimulated by cooling and drying of the nasal mucosa. Breathing warmed humidified air has been discovered to remove the stimuli of cold and dryness and remove or reduce this component of bronchoconstriction.

Asthmatic subjects studied in the evaluation had mild to moderate asthma, with Forced Expiratory Volume after one second ($FEV_1$) between 45% and 75% normal at screening, were non-smokers and had no other diagnosed conditions, or their conditions were stable and controlled. Subjects were asked not to use asthma medication on the day of the study. Control subjects had normal pulmonary functions. All subjects were asked to fill in a rhinitis score questionnaire for 14 consecutive days. Five control and 11 asthmatic subjects were studied. Valid data were obtained from 5 controls and 9 asthmatic subjects (age range 34-78).

The following protocol was used in the study:
1. Baseline Pulmonary Function Test (PFT) and nasal resistance measurement.
2. One hour of placebo breathing using a delivery system set to <5 lpm flow at 34C, connected to the nasal cannula via a 6-foot oxygen tube. With this arrangement the air emerged from the cannula at approximately 26C, and the water content per liter was approximately ¼ that at 41 C.
3. Placebo PFT and nasal resistance measurements. There was a 15 minute interval between the end of the placebo period and the nasal resistance measurements, because preliminary tests showed some rapid changes in the first few minutes after the placebo period.
4. One hour test breathing with a delivery system set at 20 lpm, 41 C, using a short nasal cannula. Air temperature at the nasal prongs was 39-40C.
5. Final PFT's and nasal resistance measurement.

In most asthmatic patients there was a fall in both Forced Vital Capacity FVC and $FEV_1$ between baseline and post-placebo measurements. Taking the asthmatic subjects as a group, FVC increased between placebo and tests (p=0.03). $FEV_1$, decreased between baseline and placebo (p<0.01) and then increased between placebo and tests (p=0.016). The $FEV_1/FVC$ ratio, PEF and $FEF_{25-50}$ did not change consistently between placebo and test.

The following table summarizes changes from placebo to treatment (as % change from placebo (see Chart 1 below)):

|  | Avg. | Min | Max | p-value |
| --- | --- | --- | --- | --- |
| FVC | 5 | −6 | 11 | .03 |
| $FEV_1$ | 5 | −5 | 13 | .02 |
| PEF | −15 | −50 | 8 | n.s. |
| $FEF_{25-50}$ | 12 | −6 | 50 | n.s. |
| $FEV_1/FVC$ | 0.7 | −10 | 18 | n.s. |

The changes reported in Chart 1 are averaged changes over the group.

The evaluation described in Example 1 revealed that $FEV_1$ and possibly FVC increase after 1 hour of treatment (20 lpm, 41C; temperature at nasal prongs 39-40C) compared with 1 hour placebo. Almost all of the subjects, both control and asthmatic, liked the treatments and felt comfortable using the air delivery system. Some asthmatic subjects reported feeling that their nasal airways were unusually clear after treatment.

Figure 42:
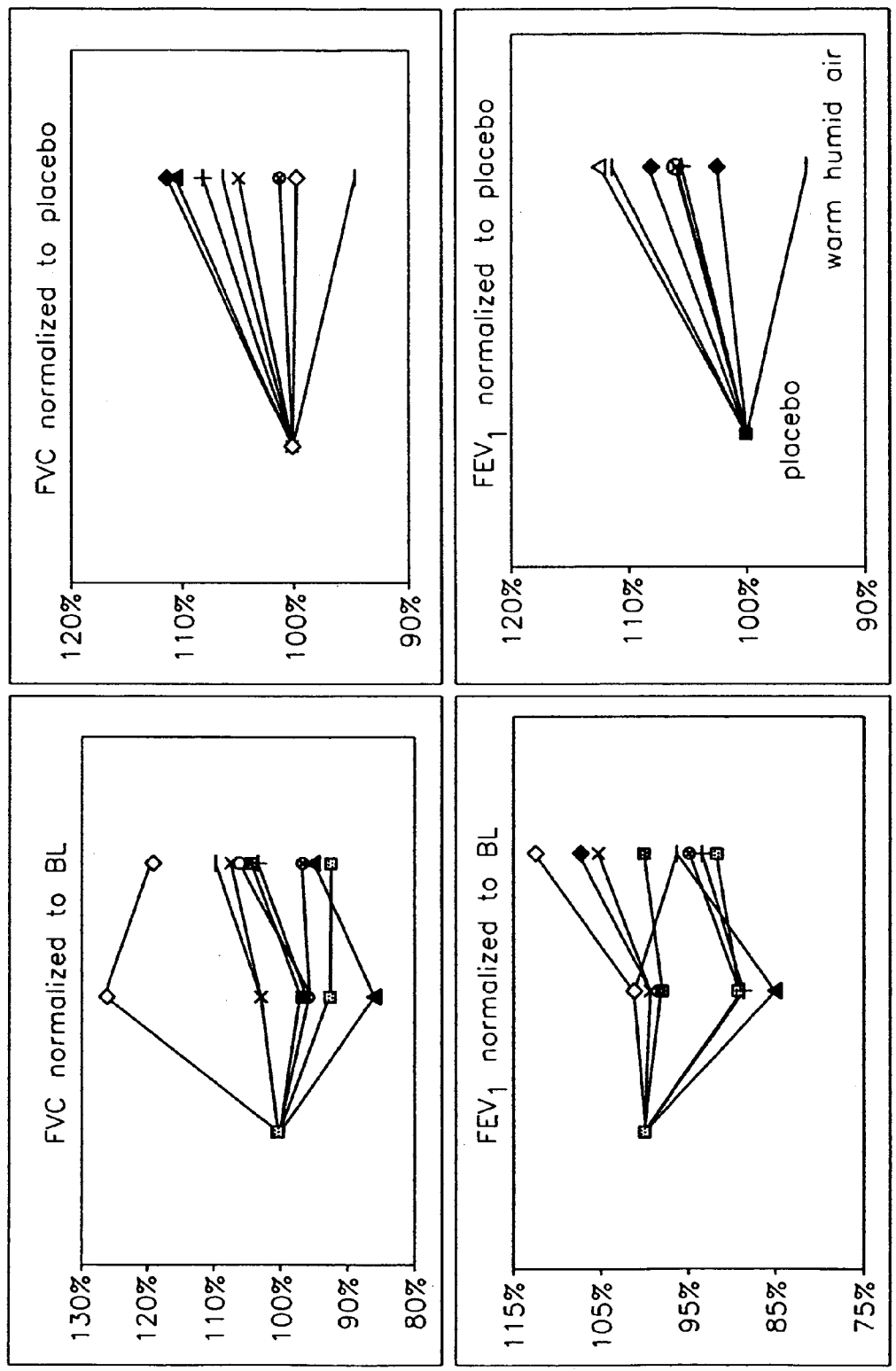
FIG. 42 is a graphical representation of changes in FEV1 and FVC normalized to baseline (left) and placebo (right) in asthmatic patients.

FIG. 42 illustrates chanaes in $FEV_1$ and FVC normalized to baseline (left) and placebo (right) in asthmatic patients. Most patients showed an increase in both between placebo and test.

In another aspect of the method according to this invention, it has been discovered that the introduction of heated and humidified air can reduce the discomfort associated with chronic rhinosinusitis in cystic fibrosis patients. It has been recognized that many cystic fibrosis patients have chronic rhinosinusitis due to infection, inflammation, and thickened secretions, and therefore require continuous medication. Many such patients receive repeated surgical procedures to drain the paranasal sinus when medical treatment fails, but the effect of such surgery can be short-lived. Standard therapy can include saline nasal washes and antibiotics, and corticosteroids if nasal polyps are present. Accordingly, improvements to such treatments of rhinosinusitis are needed. This is especially true in cystic fibrosis patients because they tend to produce mucus that is scanty and thick, and the mucoliary transport system is sometimes unable to clear bacteria from the nasal mucosa. Also, the low secretion volume may leave the mucosa susceptible to drying out and injury. Infection and injury can then lead to inflammation. Similarly, the introduction of heated and humidified air has also been discovered to reduce the symptoms of refractory rhinosinusitis.

Chronic obstructive pulmonary disease (COPD) has also been associated with symptoms that can be effectively treated by the introduction of heated and humidified air by means of the apparatus and method of this invention. For example, the delivery for 30 minutes of high flow, humidified, heated room-air delivered by nasal cannula to COPD patients at about 20 liters per minute of flow has been discovered to provide an effective alternative or delivery system for oxygen in COPD patients.

It has also been discovered that high nasal flow using a system according to this invention decreases the work of breathing. Specifically, it has been discovered that the introduction of heated and humidified air or breathing gas into the nasal passageway of a patient decreases work of breathing. Most preferably, heated and humidified breathing gas delivered at about 25 to about 35 liters per minute, thereby reducing the work of breathing. Reduction of work of breathing is clinically significant in COPD patients who may have three times normal work of breathing and may also be malnourished.

The introduction of heated and humidified breathing gas according to this invention also reduces the retention of carbon dioxide ($CO_2$) and decreases shortness of breath. Specifically, COPD patients frequently have rapid shallow breathing which can be inefficient at clearing carbon dioxide from the lungs and can lead to feelings of breathlessness. As is illustrated in the following Example, it has been discovered that high nasal flow can both reduce work of breathing and reduce breathing rates in normal subjects.

EXAMPLE 2

Ten (10) normal subjects and five (5) COPD patients were stedied.

Figure 43A:
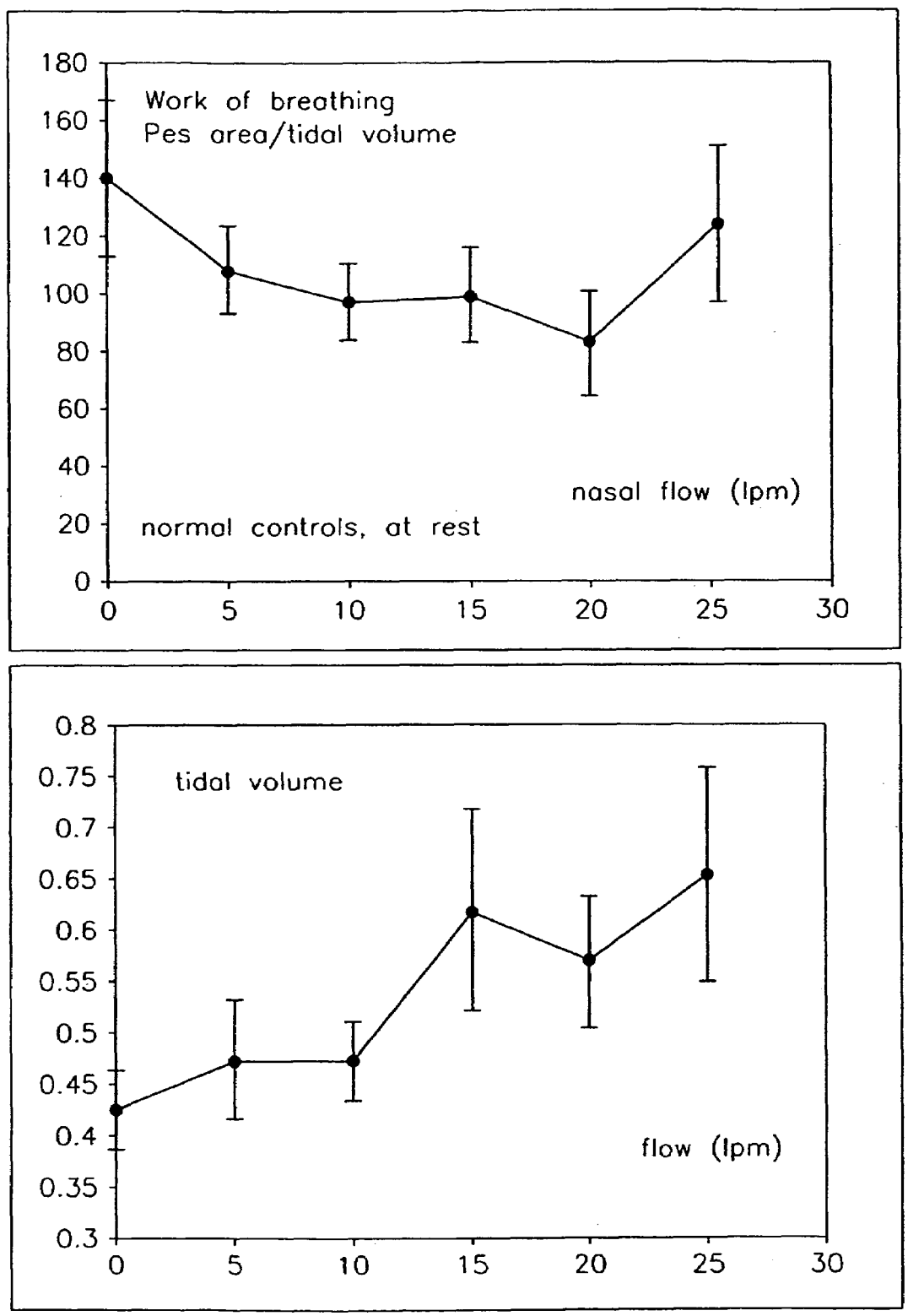
FIG. 43A are graphical representations of work of breathing vs. nasal flow and tidal volume vs. nasal flow.
Figure 43B:
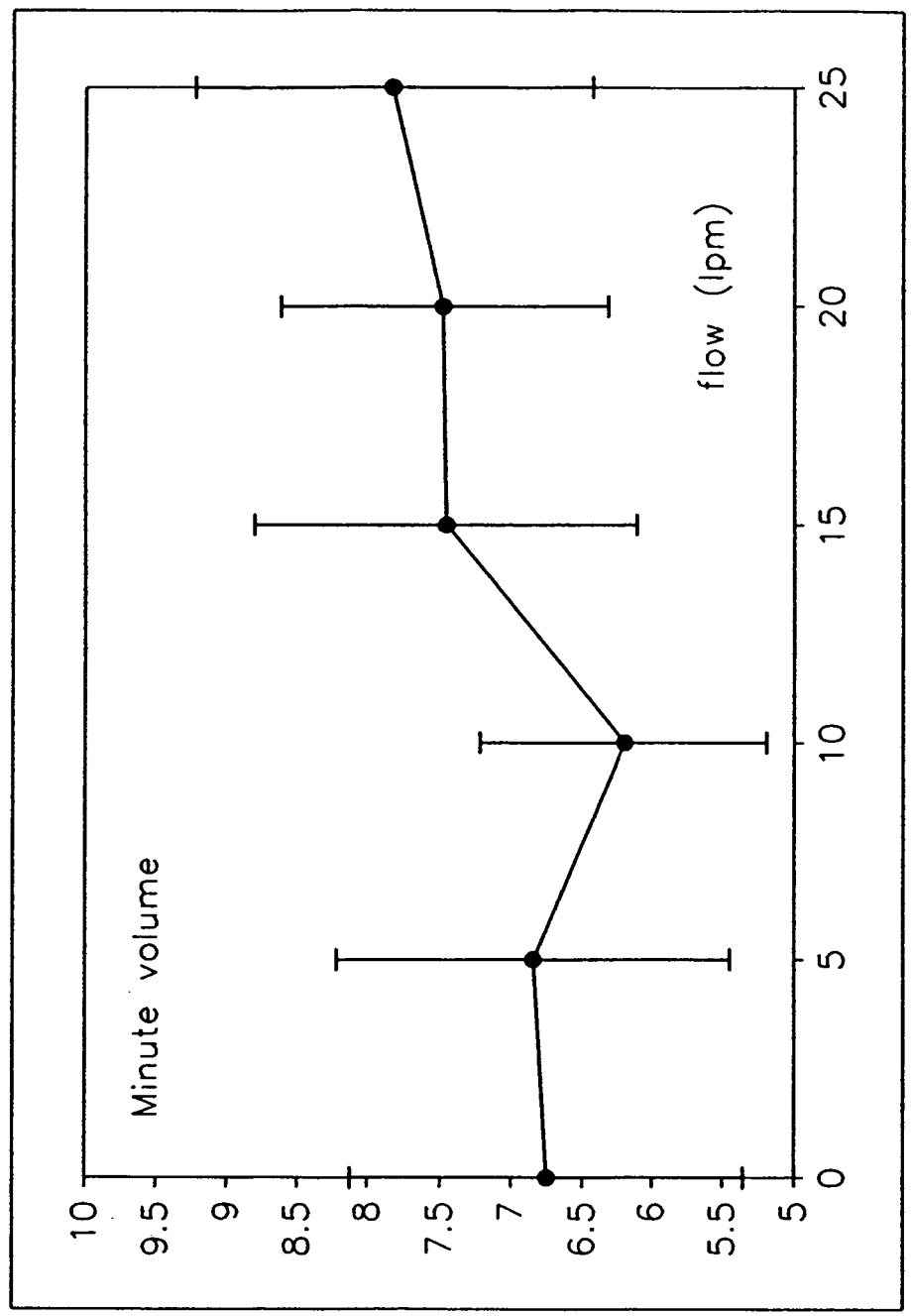
FIG. 43B is a graphical representation of minute volume vs. nasal flow.

For the normal subjects, work of breathing and respiratory responses to heated and humidified flow were measured. Specifically, flow from 0 to 25 liters per minute was administered to the normal subjects at rest and during exercise. The results are provided in FIGS. 43A and 43B.

The results that, at rest, the mean work of breathing was reduced progressively by increasing nasal flow. When nasal flow increased from 0 to 20 liters per minute, the mean work of breathing fell by 42%. The results indicate a preferred range of flow rates from about 15 to about 20 liters per minute.

In the same group of normal subjects, mean tidal volume (i.e., the volume of air per breath) increased about 52% from 0.42 liters to 0.64 liters as nasal flow increased from 0 to 25 liters per minute. The results indicated that minute volume (volume breathed per minute) did not change significantly. Nevertheless, it was discovered that the breathing pattern was significantly changed. As the nasal flow increased, breathing became slower and deeper. Slow deep breathing is believed to be more effective than rapid shallower breathing in removing carbon dioxide from the lungs. Also, rapid shallow breathing is associated with the sensation of breathlessness (dyspnea) found in disease conditions such as COPD and acute asthma attacks.

Preliminary data from normal subjects during exercise indicated approximately 30% decrease in work of breathing when nasal flow was increased from 0 to 25 liters per minute.

Figure 44:
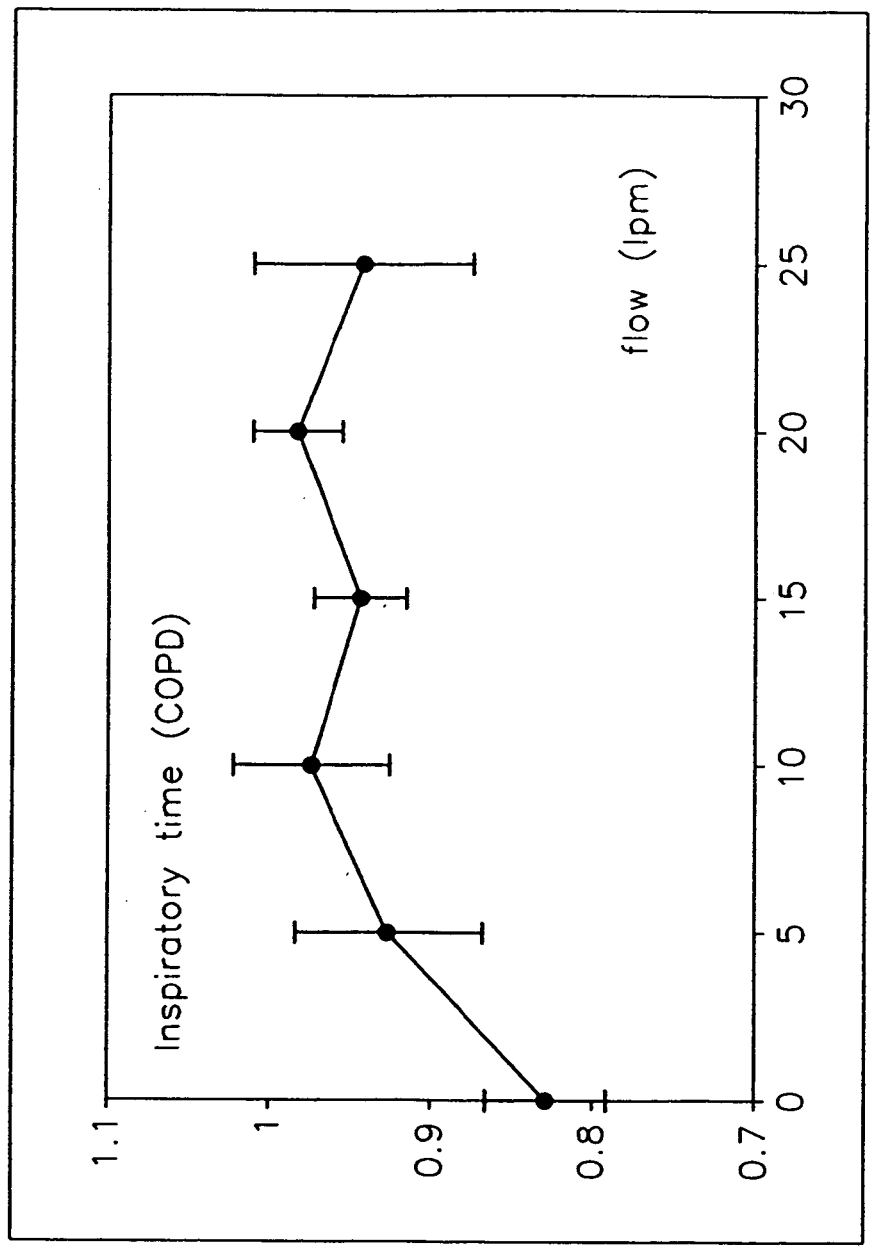
FIG. 44 is a graphical representation of inspiratory time vs. nasal flow.

With regard to COPD patients at rest, the COPD patients had a base line respiratory rate of 27 per minute as compared to 17 per minute for the normal subjects. COPD patients showed about a 20% increase in the mean duration of inspiration (Ti) when the nasal air flow was increased from 0 to about 20 liters per minute while respiratory time did not change. There was an 11% decrease in overall respiratory rate. The longer Ti indicates a change to a more comfortable and less labored breathing pattern. See the results÷ illustrated in FIG. 44.

Another respiratory tract condition, obstructive sleep apnea (OSA), affects about 4% of men and about 2% of women. If left untreated it can be associated with significant mortality. Another condition, UARS (also known as respiratory effort-related arousal, RERA), has been recognized only recently as pathological and in need of treatment. Physiologically, upper airway resistance syndrome (UARS) is caused by an increase in upper airway resistance short of complete obstruction, and appears to lie on a continuum between non-symptomatic snoring at one end and clinically significant OSA at the other. Unlike OSA, UARS does not include significant desaturation or obstructive apnea. However, the patient has a slightly increased arousal index and number of awakenings, with snoring and daytime sleepiness.

Although continuous positive airway pressure (CPAP) has been proposed for the treatment of OSA and UARS, it has been discovered that compliance with CPAP treatment is poor. Patient complaints relating to non-compliance include feelings of claustrophobia and a perceived lack of benefit. Also, many CPAP patients report significant side-effects such as nasal congestion, dry nose or throat, and discomfort associated with cold air. Epistaxis occurs infrequently but can be severe, and chronic nasal congestion may compromise a patient's ability to successfully utilize CPAP.

An obstructive apnea is defined as cessation of airflow for an extended period of time (such as more than 10 seconds) accompanied by an arousal or desaturation. It is believed that the introduction of 100% humidified air at a flow rate of 20 liters per minute can reduce the effects of OSA and UARS. The partial (UARS) or complete (OSA) airway blockage appears to be due to airway collapse under the negative pressure caused by normal inspiration. Conventional therapy (CPAP, BiPAP) depends on raising the airway pressure and is uncomfortable and poorly tolerated by most patients so that fewer than half of OSA patients routinely use their CPAP treatment. It has been discovered that a high nasal airflow (such as about 20 liters per minute, for example) will prevent or reduce the negative pressure of inspiration and hence reduce the incidence of airway collapse. Because high nasal flows of wann humid air will be tolerated by patients, the use of the system according to this invention for therapy of patients with OSA/UARS is beneficial.

Another condition that has been discovered to be treatable using the method and apparatus of this invention is xerostomia, occurring in post-irradiated head and neck cancer patients. Many people are diagnosed each year with head and neck cancer, and radiotherapy is an important treatment in head and neck cancer patients. However, some patients are kept awake at night because of troublesome oral dryness, and xerostomia can cause difficulty with mastication, deglutition, and articulation. It can also alter taste, change pH, and is associated with dental decay, infection, skin break down, and bone loss.

Current medical therapy for xerostomia includes frequent sips of water, chewing gum, using artificial saliva, and taking oral pilocarpine. Such therapies, however, have failed to provide adequate relief even when used in combination. Also, xerostomic patients find little benefit from standard bedside humidification devices, and previous attempts at humidification via nasal cannula have only worsened the problem by drying out the oronasal passageways from the increased airflow.

It is believed that hydrating the respiratory tract with warm, saturated (100% relative humidity) air at controlled variable flow rates through a nasal cannula of up to about 40 liters of water-saturated air per minute at dew points from room temperature to about 43° C. can provide a significant benefit. More specifically, at about 41° C., 57 milligrams of water per liter of air can be delivered to the patient's respiratory tract, which is five times the water vapor of normal room air.

Accordingly, it is believed that the introduction of heated and humidified air while the patient is sleeping as well as during periods of waking hours should reduce the severity of the symptoms associated with xerostomia.

It is also recognized that premature infants in natal intensive care units may require supplemental oxygen after they are weaned from mechanical ventilation. For example, premature infants may require supplemental oxygen and airflow for the following conditions: respiratory distress syndrome secondary to lung immaturity, transient tachypnea of the newborn, pneumonia, chronic lung disease, and/or apnea and bradycardia of prematurity.

Premature infants being weaned from mechanical ventilation are typically given nasal continuous positive airway pressure (NCPAP) for some period to keep the airway open. Conventional equipment is bulky and poorly tolerated, and there can be some risk of injury to the infant's nose from the patient interface and from the flow of inadequately humidified breathing gas. The administration of high flow fully humidified breathing gas by nasal cannula can provide sufficient respiratory support for such premature infants with reduced risk of trauma.

Conventionally, room-temperature, dry oxygen is delivered to premature infants. However, frequent adjustment of flow rate is necessary to maintain consistent oxygenation, and the amount of oxygen that can be delivered is limited by the drying effect of high nasal flow. It has been discovered, therefore, that conditioning of an air-oxygen mixture by warmth and humidity will allow a higher flow rate which will result in more consistent oxygenation. It has also been discovered that more oxygen can be safely delivered by this method than with dry cold oxygen flow so that infants with larger oxygen requirements can be supplied by nasal cannula. This is especially true in view of the fact that premature infants in natal intensive care units can sometimes undergo episodes of hypoxia despite the constant monitoring and adjustment of settings.

Stable oxygenation is especially important in the treatment of premature infants having respiratory distress syndrome. Even after a premature infant's syndrome has improved to the point that mechanical ventilation is no longer needed, the infant frequently will require supplemental oxygen and low continuous distending pressure that is delivered via nasal continuous airway pressure (CPAP). However, in the smallest infants, the diameter of the NCAP prongs is larger than the diameter of the infant's nares. When supplemental oxygen must be delivered by nasal prongs, it is dry and cold, thereby increasing the risk of mucous plugs and reflex bronchoconstriction, which would increase the work of breathing.

It has been discovered that the ability to deliver warm and humidified oxygen to infants makes it possible to deliver oxygen at higher flow rates than with conventional systems with less risk of airway damage. Accordingly, the method according to this invention of delivering supplemental oxygen to infants is especially beneficial in that it maintains a more constant level of oxygenation than with conventional systems, and it provides mild distending pressure with higher flow rates that will allow earlier respiratory development of the smallest infants. Also, since essentially all of the inspired air will come from the delivery system, infants will breathe sterile filtered air with almost no increased risk of infection. Also, heated and humidified air can be delivered to the infant for up to or more than two hours at a temperature set so that the air reaches the nose at a temperature of about 33-35° C.

For similar reasons the method according to this invention is also beneficial for use with infants with Broncho Pulmonary Dysplasia (BPD) for treatment in a step-down unit. Such infants require continuous supplemental oxygen to maintain their saturation. Conventional therapies use low-flow 100% oxygen, and it has been discovered to be difficult to maintain saturation within therapeutic limits. It has been discovered, however, that warmed, humidified air-oxygen mixtures can be supplied according to this invention at lower flows (such as about 5 liters per minute), in order to provide a more consistent oxygen saturation with fewer interventions.

The delivery of warm and humidified oxygen is also believed to be beneficial for rewarming of small premature infants after delivery and during stabilization. Small premature infants have little fat stores and lose heat quite rapidly after delivery and can become significantly hypothermic during the transition from delivery room to the neonatal intensive care unit. Even though these infants are stabilized on radiant warmers, the smallest of infants can still become hypothermic during catheter placement procedures. In addition to heat loss, premature infants also have high water losses secondary to immaturity of the skin. These fluid losses can be excessive during stabilization after birth. Infants less than 750 grams may have 100-200 cc/kg/day of insensible free water losses during the first several days of life even when placed in a heated, double-walled isolette. Humidified air or oxygen has been discovered to provide a means to give additional free water and warmth through the respiratory tract.

It is also believed that the introduction of heated and humidified air can enhance the effect of inhaled bronchodilators for the delivery of medication aerosol at body temperature. For example, during an acute asthma exacerbation, one may tend to breathe harder, faster and through the mouth thus decreasing the body's warming and humidifying apparatus. Also, with the administration of nebulized treatments, patients are offered cold or cool aerosolized medications, which may exacerbate or at least work against the desired effects. It is believed that pre-warming of the inhaled aerosol from a nebulizer should reduce or abolish any cold-induced bronchospasm and allow the medications to reach more lung airways.

Re-warming of Patients After Surgery

It has been recognized that reduced core body temperature during recovery from anesthesia can be associated with increased risk of heart attacks and infection. Many conventional re-warming methods rely on surface heating (e.g. circulating water mattresses, forced-air warming blankets) and can be slow to raise core temperature. Ideally, heat should be transferred directly into the core thermal compartment, but access to the core is difficult short of using extracorporeal bypass.

Hypothermia is known to occur in the majority of surgical patients since virtually all anesthetics impair the body's ability to regulate temperature. It has been estimated that 50-70% of patients leave the operating room with core temperatures less than 36° C., and 33% of patients have a core temperature that is less than 35° C. Hypothermia presents a greater risk of myocardial ischemia and cardiac morbidity. Anesthetic drugs are more slowly metabolized and hypothermia prolongs the length of stay of a patient in the recovery room. Hypothermia has also been associated with increased incidents of infections and patient discomfort. For these reasons, it has been recognized that it is advantageous to aggressively re-warm patients after surgery to restore body temperature.

It is also recognized that significant heat and moisture is lost through the respiratory tract from breathing cool dry gases, and therefore dry mouth is a common complaint after surgery. This is a result of anticholinergic medication that is routinely given as part of the anesthetic regimen.

It has been surprisingly discovered that breathing warm air (above body temperature) in accordance with this invention will transfer heat to the body core and will accelerate the re-warming process. Air delivered at 100% saturation, a controlled safe temperature, and a flow rate sufficient to supply almost all or all of the inspired air flow (so no room air is entrained and the heat transfer to the patient is maximized) can reduce the hypothermic condition of the patient.

The high humidity has been discovered to ensure that the patient's airways are not damaged by drying and significantly reduces the discomfort from post-operative dryness caused by drugs given during surgery. It has further been discovered that the evaporative heat loss associated with breathing cool dry gases can be eliminated by providing 100% humidified air. Heated and humidified air can be introduced at about liters per minute flow through a nasal cannula to accomplish patient re-warming.

EXAMPLE 3

Thirty patients were studied who were scheduled to undergo intra-abdominal surgical procedures. Exclusion criteria were preoperative fever (>38 C), history of hypo- or hyperthyroidism, and significant cardiac disease by history.

Intraoperatively, patients received a balanced general anesthetic consisting of thiopental, fentanyl and/or hydromorphone, rocuronium or pancuronium, and isoflurane or desflurane. All intravenous fluids were prewarmed to between 37 C and 38 C. Intraoperatively, one layer of surgical drapes and one layer of cotton blankets were used to cover the patients, but no active warming measures (i.e. forced-air devices) were used.

Upon admission to the recovery room, patients were randomly assigned to receive either (1) anhydrous room temperature oxygen delivered at 4 L·min$^{-1}$ by mask (control, n=15), or (2) warmed, humidified oxygen therapy at 20 L·min$^{-1}$ (test, n=15). One layer of warmed cotton blankets was used to cover the patients but no other warming methods were utilized.

In the test group the oxygen was warmed to 42 C measured at the tip of the nasal cannula. The therapy duration was 90 minutes followed by an additional 30 minutes of temperature monitoring, during which the subjects breathed room temperature anhydrous oxygen at 4 ·min$^{-1}$. core temperature was measured at the tympanic membrane using a tympanic thermocouple probe MONA-THERM (Mallinckrodt Medical, St. Louis, Mo.) and an ISO-THERMEX electronic thermometer (Columbus Instruments, Columbus, Ohio).

Discomfort from mouth dryness was evaluated using a 0-4 point scale where 0="as dry as your mouth has ever been," and 4="no dry mouth discomfort." Dry mouth scores were analyzed as a dichotomous outcome, with a score less than or equal to 1 defined as a dry mouth.

The system used during this evaluation allows high flow oxygen delivery that is 100% humidified and warmed. The system consists of a main unit and a delivery tube. In the main unit, air is taken in by a compressor and pumped through a Pall bacteriological filter into a cartridge where it passes through tubes of membrane material surrounded by water at about 41 C. The membrane pore size is about 0.01 micron, allowing molecular water vapor to pass but retaining bacteria and other particulates. Liquid water is retained by the hydrophobic (non-wettable) nature of the membrane material. On leaving the cartridge the air is sterile and 100% saturated with water vapor. The airway in the delivery tube is surrounded by a jacket that is heated to about 42 C by water pumped from the main unit, to maintain the air temperature and prevent condensation.

The two groups were similar for age, height, and body mass index. The test group had a greater body mass. (Table 1). The duration of surgery and core temperature upon admission were similar between the two groups (Table 2).

TABLE 1

Patient Demographics

|  | Control | Test | P Value |
|---|---|---|---|
| N | 15 | 15 |  |
| Age (yr) | 48 ± 4 | 49 ± 4 | 0.92 |
| Weight (kg) | 69 ± 3 | 82 ± 7 | 0.05 |
| Height (cm) | 167 ± 2 | 158 ± 18 | 0.48 |
| Body Mass Index (kg · m$^2$) | 24.7 ± 0.9 | 26.6 ± 1.6 | 0.29 |

TABLE 2

Preoperative Data

|  | Control | Test | P Value |
|---|---|---|---|
| N | 15 | 15 |  |
| Duration of surgery (min) | 180 ± 29 | 134 ± 15 | 0.19 |
| Core temperature Upon PACU Admit (° C.) | 35.9 ± 0.2 | 35.7 ± 0.1 | 0.57 |
| Core Rewarming Rate* (° C. · hr$^{-1}$) | 0.35 ± 0.06 | 0.67 ± 0.08 | 0.003 |

*-during the first postoperative hour

Figure 45:
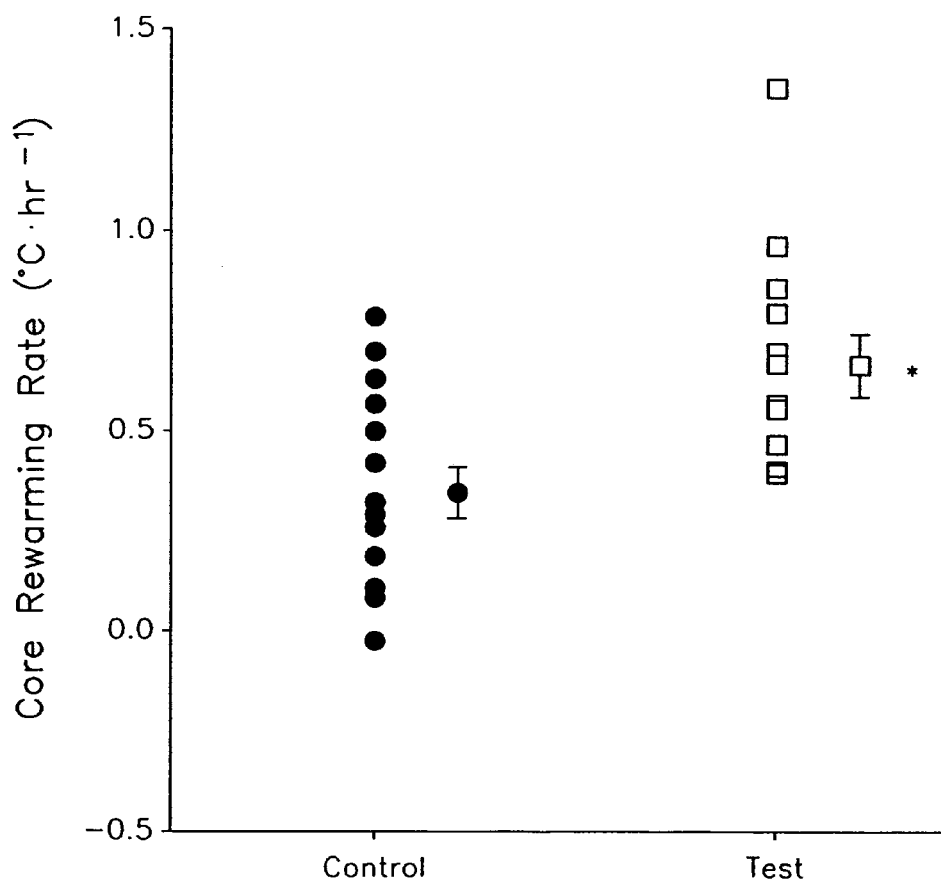
FIG. 45 is a graphical representation of core rewarming rates for a control group vs. a test group.
Figure 46:
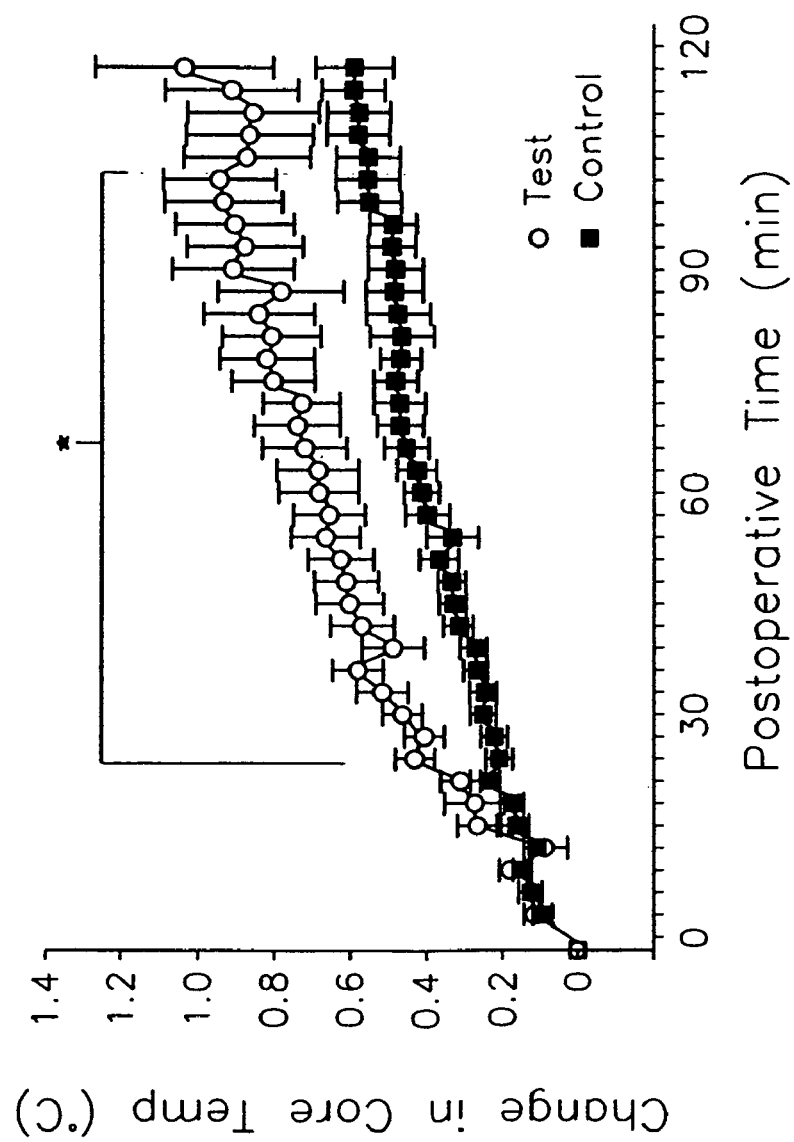
FIG. 46 is a graphical representation of changes in core temperatures for a control group vs. a test group vs. postoperative time.
Figure 47:
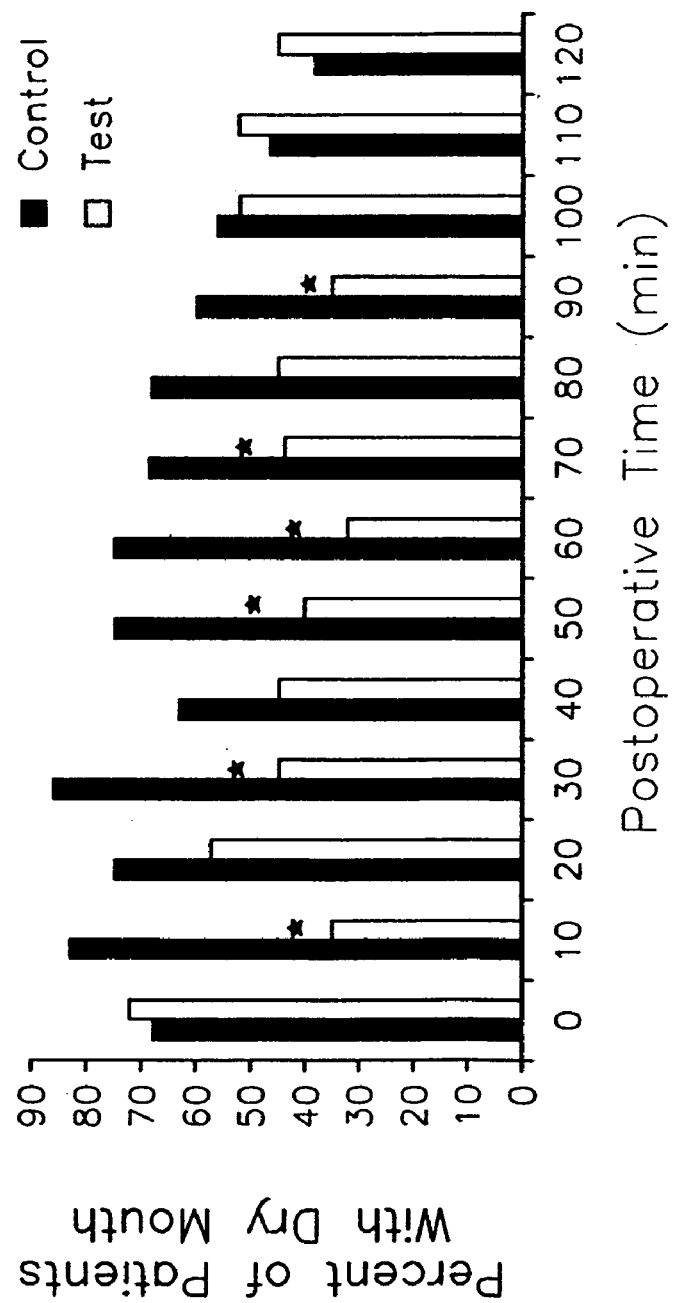
FIG. 47 is a graphical representation of percentages of patients with dry mouth for a control group vs. a test group vs. postoperative time.

The following charts illustrate the results of the evaluation:

FIGS. 45-47 illustrate the results of the evaluation. FIG. 45 shows core rewarming rate for patients receiving routine oxygen therapy (Control) or warmed, humidified oxygen therapy (Test) in the initial postoperative hour. Rewarming was accelerated in the Test treatment group (*-P=0.003 vs. Control). FIG. 46 shows change in core temperature from baseline, measured upon admission to the postanesthesia care unit. Core temperature increased more rapidly in the Test treatment group (*-P<0.05 vs. Control). FIG. 47 shows patients in the Test group had a lower incidence of dry mouth in the postoperative period (*-P<0.05 vs. Control).

In the initial postoperative hour, core rewarming rates were greater in the test group (0.67±0.08° C.·hr$^{-1}$) than in the control group (0.35±0.06° C.·hr$^{-1}$) (P=0.003) (Chart 1). The change in core temperature from baseline was greater in the test group than in the control group at 1 hour (0.6±0.1° C.·vs. 0.4±0.1° C.) (P<0.03) and at 2 hours (1.0±0.1° C. vs. 0.6±0.1° C.·)(P<0.04) (Chart 2).

The incidence of dry mouth was similar upon PACU admission, then lower in the test group during the treatment period (P<0.05) (Chart 3). After 90 min, when the treatment was discontinued, the incidence of dry mouth was similar between groups.

As illustrated in Example 3 above, the delivery of warmed, humidified oxygen has been discovered to accelerate the rate of core rewarming by approximately two-fold in mildly hypothermic postoperative patients. This effect is believed to be partially related to direct heat transfer though the respiratory tract into the pulmonary vasculature. In addition, the elimination of evaporative heat loss is believed to contribute to the accelerated rate of rewarming.

It has been discovered that significant heat can be lost through the respiratory tract from breathing cool dry gases, and evaporative heat loss can be significantly reduced by providing 100% humidification. Active warming and humidification of the inspired mixture can prevent heat loss and reduce the magnitude of hypothermia in small children undergoing general anesthesia and surgery. In adult patients, however, intraoperative warming and humidification appears to have little or no effect on core temperature. This age-related difference in effect is probably explained by a relatively greater proportion of total heat loss through the respiratory tract in children compared to adults.

Postoperatively, the percent of total body heat loss through the respiratory tract is likely to be greater than during the intraoperative period. Compared to the intraoperative period, there should be less cutaneous heat loss via radiation since anesthetic-induced vasodilatation is significantly less, and there is less exposure of the body surface and body cavities to the atmosphere. These intra- and postoperative differences may explain the greater effect of warmed humidified breathing gases according to this invention on body temperature in the postoperative period.

An estimation of heat transfer can be calculated to compare rewarming rates between the test and control groups if several assumptions are made, i.e., that total body heat production and heat losses are similar in the two groups, and that the respiratory duty cycle and mean inspiratory flow rate are about 1:1 and 20 L·min$^{-1}$, respectively. Given the specific heat of the human body (0.83 cal·kg$^{-1}$·°C.$^{-1}$); 57 mg water vapor per liter; 540 cal per gram of water for heat of condensation; and using the average body mass of the subjects of the evaluation in Example 3, the estimated effect of treatment on rewarming rate is about 0.33° C. per hour. Accordingly, the average patient receiving treatment is believed to rewarm 0.33° C. more rapidly each hour relative to a patient breathing conventional oxygen therapy.

There was a difference in body mass between the test and control groups in Example 3, and the greater body mass in the test group may have influenced rewarming. The effect of a greater body mass, however, would be a decreased rewarming rate, since the amount of heat transfer per unit of body mass would be decreased. Therefore the average is patient receiving treatment would be likely to rewarm more than about 0.33° C./hr faster as compared to conventional therapy.

As discussed above, dry mouth is a common complaint after surgery which often results from anticholinergic medications (i.e. glycopyrrolate or atropine) that are routinely given as part of the anesthetic regimen. Example 3 demonstrated that humidified warmed breathing gases according to this invention alleviate this discomfort. This effect is likely to increase patient satisfaction following surgery.

In summary, the delivery of warmed, humidified oxygen as described in Example 3 has been discovered to accelerate core rewarming rate by approximately two-fold in mildly hypothermic patients. In addition, there is less discomfort from dry mouth in patients receiving this therapy.

Although the foregoing discussion generally relates to post operative patients, it is recognized that the system and method according to this invention can be utilized for any hypothermic subject. In other words, the system and method of this invention can be applied to raise the body temperature whenever needed and for whatever reason.

Improvement of Peak Performance of Athletes

It has been surprisingly discovered that high flow, humidified, heated room air can improve the pulmonary function and peak exercise performance in human athletes. Moreover, many professional and amateur athletic teams compete under dry-air conditions (e.g. fall-to-winter sports, such as football, and winter sports, such hockey, basketball, skiing, and skating). It has been discovered that athletes performing in such conditions can benefit from pre-exercise treatment by the introduction of heated and humidified air. Also, it has been discovered that such treatment can limit pulmonary stress and help to prevent exercise-induced bronchospasm and bronchitis in a manner that is not prohibited by regulations such as the regulations of the International Olympic Committee. Such treatment can also provide improved therapy for exercise-induced asthma.

EXAMPLE 4

The effects of pre-exercise breathing with high-flow, humidified air were evaluated on treadmill-running time to exhaustion in simulated sprinting and 10-kilometer endurance running conditions in trained, well-conditioned athletes. University at Buffalo Track Team members exercised to exhaustion in two protocols: (1) short intense exercise to simulate sprinting uphill on a treadmill 10% incline at 95% VO$_2$max (n=15 runners, mean VO$_2$max=56.61 ml/kg/min); and (2) running with no incline on the treadmill, at each runner's 10-kilomoeter racing speed (n=6 runners, mean VO$_2$max=54.91 ml/kg/min.).

Runners were randomly assigned to either run with pre-exercise breathing (37° C.) or the control, without pre-exercise breathing for one hour prior to exercise. Heart rate (HR), respiratory rate (RR), minute ventilation (V$_E$), oxygen consumption (VO$_2$), end-tidal carbon dioxide (P$_{ET}$CO$_2$), and arterial oxygen saturation (S$_a$P$_2$) were measured continuously. Subjective comments after each exercise also were recorded.

The hyperthermic humidification system used in Example 4 provides warmed, soothing inhalation therapy. The system delivers a 100% humidified air stream directly to the patient via a high flow nasal cannula at flow rates between 5-20 liters/min, safely heated to just above body temperature (range, 34° C.-41° C.). A replaceable microporous membrane cartridge accomplishes air stream humidification into the vapor phase. Bacteria, molds, and other pathogens cannot pass into the air circuit. The output of the system contains molecular phase water with water particles 0.5 micron or less in size. This allows the inhaled water vapor to reach the alveoli due to the small size of the water particles having purely diffusive characteristics. The system does not tend to produce aerosolized or nebulized particles of water, which may precipitate in the upper airway of the nasopharynx Humidifying the air stream to a dew point at temperatures above 37° C. provides many times the water vapor normally available to the patient. At 41° C., the system according to this invention can deliver 57 mg of water per liter of airflow. This is approximately five times the water vapor inhaled in a typical hospital room at 21.1° C. (70° F.) room temperature having only 30-40% relative humidity. During operation of the system, the delivery tube can remain completely dry, thereby eliminating condensation in the breathing line. Heating the delivery tube with circulating liquid allows the device to carry 100% oxygen as safely as air.

In this Example, twenty university student athletes, male and female, on the track team at the University at Buffalo were selected. The following conditions were exclusionary: smoking, exercise induced asthma, any cardiopulmonary disease, taking any medications, or having any upper respiratory illness.

Maximum oxygen consumption (VO$_2$max) was pre-determined for each experimental subject. Athletes were monitored by electrocardiogram (ECG), a cardio-tachometer for instantaneous heart rate, beat-to-beat measurement of transcutaneous arterial oxygen saturation (SaO$_2$), and breath measurement of respiratory rate, minute ventilation, oxygen consumption and end-tidal carbon dioxide.

Maximal exercise performance was defined as the duration of exercise to exhaustion under both simulated, short duration (5-15 min) high-intensity sprinting and moderate duration (30-40 min) endurance conditions. In the first study, the athletes exercised twice on a treadmill at 10% incline, at 95% of their individually pre-determined $VO_2$max until they could not continue. Prior to exercise, athletes were randomly assigned to either pre-exercise breathe at body-temperature (37° C.) inspired temperature for 60 minutes at 30 lpm or to simply pre-exercise breathe room-air as the control condition prior to exercise on a separate testing day. During exercise testing, athletes breathed room air.

The second study simulated longer-duration running conditions. The athlete ran with the treadmill level (0% incline) at their individually pre-determined racing speed for a 10-kilometer race until they could not continue. These subjects were randomly assigned to either pre-exercise breathe at 37° C. inspired temperature exercise at 31 lpm for 60 minutes prior to exercise or pre-exercise breathe room-air.

The results of uphill sprinting and endurance running are summarized in the tables provided below.

TABLE ONE

Uphill Sprinting

| | A With Treatment (@ Termination) | B Without Treatment (@ Termination) | C With Treatment (@ same time as termination without Treatment) | P value |
|---|---|---|---|---|
| Time to termination (min) | 14.7 (9.25) | 11.5 (5.36) | — | A vs. B <0.001 (+24.2%) |
| $VO_2$ (ml/kg/min) | 53.3 (2.59) | 55.8 (2.42) | — | A vs. B <0.051 (−4.4%) |
| $SaO_2$ (%) | 90.0 (1.33) | 89.8 (1.23) | 90.4 (1.64) | NS |
| $PetCO_2$ (mmHg) | 31.0 (0.89) | 32.2 (0.99) | 32.9 (0.90) | A vs. B <0.028 (−3.1%); A vs. C <0.001 (−5.7%) |
| RR ($min^{-1}$) | 61.4 (2.69) | 59.4 (2.70) | 56.8 (2.33) | B vs. C <0.038 (−4.4%); A vs. C <0.001 (+8.2%) |
| $V_E$ (l/min) | 120.8 (8.36) | 120.8 (7.08) | 116.0 (7.89) | A vs. C <0.008 (−3.9%); B vs. C <0.008 (+4.1%) |
| HR ($min^{-1}$) | 191.7 (1.94) | 188.2 (2.09) | 189.7 (2.15) | NS |
| $VO_2/VO_2$ max (%) | 93.8 (2.08) | 98.3 (1.70) | — | A vs. B <0.048 (−4.5%) |
| Time to recovery to 97% $SaO_2$ (sec) | 109.9 (20.27) | 79.5 (11.3) | — | NS |

$VO_2$ = peak oxygen consumption at steady state;
$SaO_2$ = estimated arterial $O_2$ saturation;
$P_{ET}CO_2$ = end-tidal $CO_2$;
RR = respiratory rate;
$V_E$ = minute ventilation;
HR = heart rate. (mean ± SE)

TABE TWO

Endurance Run

| | A With Treatment (@ Termination) | B Without Treatment) @ Termination) | C With Treatment (@ same time as termination without Treatment) | P value |
|---|---|---|---|---|
| Time to termination (min) | 20.5 (3.22) | 16.6 (2.52) | — | A vs. B <0.006 + 23.4%) |
| $VO_2$ (ml/kg/min) | 50.5 (3.39) | 49.1 (2.98) | — | NS |
| $SaO_2$ (%) | 92.5 (0.56) | 93.7 (0.49) | 92.8 (0.88) | NS |
| $PETCO_2$ (mmHg) | 28.6 (1.69) | 29.7 (1.97) | 31.0 (1.75) | A vs. C <0.024 (−7.9%) |
| RR ($min^{-1}$) | 74.3 (5.08) | 66.5 (4.36) | 65.9 (6.34) | NS |
| $V_E$ (l/min) | 108.1 (12.95) | 102.6 (12.89) | 98.4 (9.22) | NS |
| HR ($min^{-1}$) | 187.1 (7.85) | 184.7 (7.27) | 187.7 (5.43) | NS |
| $VO_2/VO_2$ max (%) | 92.5 (3.50) | 90.9 (2.85) | — | NS |

TABE TWO-continued

Endurance Run

|  | A<br>With Treatment<br>(@<br>Termination | B<br>Without<br>Treatment) @<br>Termination) | C<br>With Treatment<br>(@ same time as<br>termination<br>without<br>Treatment) | P value |
|---|---|---|---|---|
| Time to recovery to 97% SaO$_2$ (sec) | 140.0 (39.95) | 63.3 (14.31) | — | A vs. B<br><0.031<br>(+121.1%) |

VO$_2$ = peak oxygen consumption at steady state;
SaO$_2$= estimated arterial O$_2$ saturation;
PETCO$_2$ = end-tidal CO$_2$;
RR = respiratory rate;
V$_E$ = minute ventilation;
Hr = heart rate. (mean ± SE)

Twenty university student athletes were recruited to participate in this study. Fifteen completed this study. The mean age of the 15 experimental subjects, eight females and seven males, in the uphill sprinting study was 18.9±0.06 (SD) yrs. There was a mixture of 8 sprinters and 7 mid-distance runners. For the uphill sprinting study, the mean VO$_2$max for all 15 runners was 56.61 ml/kg/min±2.09 (SE). In the 10-Kilometer endurance running study, the mean VO$_2$max was 54.9 ml/kg/min±4.4(SE).

In the sprinting uphill study, the endurance running time for all 15 runners without treatment was 11.54±5.36 min (SD) compared to pre-exercise breathing with treatment, 14.70±9.25 (SD), an improvement of +24.23% (p<0.001). In the second study, simulating 10-kilometer running conditions, the endurance running time for all six runners without treatment was 16.60±2.52 min (SD) and with treatment was 20.54±3.22 min (SD), an improvement of +23.35% (p=0.006).

In the uphill sprinting study, the steady state oxygen consumption was 55.76 ml/kg/min±2.42 (SE) without treatment and 53.31 ml/kg/min±2.59 (SE) compared to using treatment, a difference of −4.39% (p=0.051). When these values are normalized by percentage to the individual's maximum oxygen consumption (VO$_2$max), uphill running without treatment had a steady state V0$_2$ of 98.25%±1.70 (SE) compared to 93.79%±2.08(SE) with treatment, a reduction of −4.54% (p=0.048).

Following the 10-Kilometer endurance runs, there was an increase (+121.6%,p=0.031) in the recovery time for SaO2 to return to 97% using treatment (140.00 sec±39.95 (SE)) compared to not using treatment (63.33 sec±14.31 (SE)). A Wilcoxon Signed Rank Test was used to determine this significance.

In the uphill running study, there was a reduction of −3.11% (p=0.028) in P$_{ET}$CO$_2$ at the termination of the longer runs with treatment (31.04 mmHg±0.89 (SE)) compared to the shorter runs without treatment (32.16 mmHg±0.99 (SE)). With treatment there was also a reduction of −5.99% (p<0.001) in P$_{ET}$CO$_2$ at the equivalent running time from not using the treatment (32.90 mm/Hg±0.90 (SE)) to the termination of these runs with treatment (31.04 mmHg±00.89 (SE)).

In the 10 kilometer endurance study, with treatment there was a reduction (−7.86%, p=0.024) in P$_{ET}$CO$_2$ at the equivalent running time from not using the treatment (31.03 mmHg±1.75 (SE)) to the termination of these same runs with treatment (28.59 mmHg±1.69 (SE)).

In the uphill running study, there was a decrease (−4.39%, p=0.038) in respiratory rate (RR) from the termination of the shorter runs without treatment (59.41 breaths/min±2.70 (SE)) to the same equivalent running time with treatment (56.80 breaths/min±2.33 (SE)). With treatment, there was an increase (+8.17%, p<0.001) in RR at the equivalent running time from not using the treatment (36.80 breaths/min±2.33 (SE)) to the termination of these same runs with treatment (61.44 breaths/min±2.69 (SE)).

In the 10-kilometer endurance study, there was an increase (+11.79%, p=0.03) in RR at the termination of runs without treatment (66.49 breaths/min±4.36 (SE)) compared to runs with treatment (74.33 breaths/min±5.08 (SE)).

In the uphill running study, there was a decrease (−3.94%, p=0.008) between maximum minute ventilation (V$_E$) from the shorter runs without treatment (120.80 l/min (BTPS) ±7.08 (SE)) compared to the same equivalent running time with treatment (116.04 l/min (BTPS)±7.89 (SE)). With treatment, there was an increase (+4.08%, p=0.008) in V$_E$ at the equivalent running time from not using the treatment (116.04 l/min (BTPS)±7.89 (SE)) to the termination of these same runs with treatment (120.77 l/min (BT)±8.36 (SE)).

Accordingly, pre-exercise breathing with treatment caused an improvement in both uphill sprinting running time (+24.23%) and simulated 10-kilometer endurance running time (+23.35). The use of treatment was also accompanied by a reduction in steady state VO$_2$ (−4.54%), RR (−4.39%) and V$_E$ (−3.94%) at the termination of the runs.

It is believed that pre-exercise treatment breathing may prevent airway drying during exercise. Intense exercise can result in the development of high hydrostatic pressure in the pulmonary capillaries, subsequent interstitial pulmonary edema, limiting gas exchange and resulting in hypoxemia. Pre-exercise breathing with treatment is believed to improve gas exchange during intense exercise by limiting hydrostatic damage to the pulmonary vasculature. Also, it is believed that treatment may increase running time by decreasing energy expenditures as suggested by a reduction in VO$_2$ (−4.54%). The decrease in V$_E$ after treatment suggests that the work of breathing may be reduced compared to without treatment. The decrease in RR and V$_E$ may reflect a decrease in the work of breathing caused by treatment.

It is recognized that the maximum airflow rate during inspiration at rest is often about 30 to 35 liters per minute. Preferably, heated and humidified breathing gas is introduced according to this invention at a flow rate that is high enough to ensure that almost all of a subject's inspired gas comes from the nasal cannula so that they entrain a minimum amount of room air, thereby avoiding dilution of the warm humid air with cool dry room air. Under some circumstances, flows above about 40 liters per minute can become uncomfortable and can start to make exhalation more difficult. The most preferred range of flow rates is therefore about 30 to about 35 liters per minute for pre-exercise therapy.

Also, a temperature of introduced breathing gas of about 37° C. is preferred. A higher temperature would deliver more moisture but has also been discovered to raise body temperature. A temperature lower than 37° C. would deliver less moisture.

Although a shorter or longer duration can be selected, a duration of about one hour prior to exercise is preferred as an upper limit although longer durations also appear to be therapeutically beneficial.

Although the foregoing Example relates to pre-exercise treatment, it has also been discovered that the delivery of high flow oxygen at high humidity can improve performance during exercise. Specifically, the delivery of heated and humidified breathing gas to a subject can help reduce their work of breathing and enhance exercise performance through the same mechanism as for pre-exercise treatment. One example of treatment during exercise might apply to pulmonary rehabilitation programs (e.g., after lung surgery), which programs are based on improving lung function by exposing the patient to exercise so that they exercise the respiratory system. By enhancing exercise performance in such patients according to this invention, they can do more work and accelerate the rehabilitation process.

It has been discovered that another beneficial application of the system and method of this invention is the introduction of high flow oxygen to patients requiring supplemental oxygen. For example, patients with severe lung disease often require supplemental oxygen, but conventional systems often have a maximum gas flow of about 6 liters per minute by nasal cannula. Higher flow rates using conventional systems have been discovered to cause drying and cooling in the upper airway. The drying and cooling can cause discomfort and airway damage. If higher oxygen flows are needed, it is often necessary to use a breathing mask, which causes difficulty for the patient with respect to speaking and feeding. Some patients are also claustrophobic and can be subject to panic attacks while wearing a mask.

Using the system and method according to this invention, it has been discovered that airflow rates up to about 40 liters per minute (or even higher) by nasal cannula are well tolerated when the humidity is greater than about 90% and the temperature is at or above 37° C.

In another application of the system according to this invention, it has been discovered that the introduction of heated and humidified breathing gas is beneficial for voice treatment. Dry air inhalation can impair voice production and, for professionals who depend on the use of their voice, this can reduce their ability to work. The system and method of this invention provide an improved manner in which heated and humidified breathing gas can be introduced to the upper respiratory tract for voice treatment. Also, the system and method according to this invention can be comfortably administered while the subject is asleep.

It has further been discovered that atrophic rhinitis is beneficially treated using the system and method according to this invention. Maintenance of high humidity in the nasal passages is believed to significantly promote healing of the lesions in atrophic rhinitis with improvements in quality of life.

The supply unit according to this invention has also been discovered to have application in connection with ventilator weaning using a trans-tracheal cannula. Cannulas for delivering breathing gas to the trachea of a patient are available under the trademark SCOOP from Trans-Tracheal Inc. of Denver, Colo. Although it is believed to be beneficial to provide breathing gas at flows 6 to 10 liters per minute, it has been discovered that some patients benefit from higher flows of 15-20 liters per minute. Such higher flows can be humidified according to the system and method of this invention, thereby removing the risk of drying of the tracheal airway. Flow rates of up to 15 liters/min, humidified according to this invention, have been found effective in maintaining normal blood oxygen levels in patients with severe obstructive lung disease. Most preferably, flow rates of about 10 to about 15 liters per minute are provided for oxygen saturation levels of about 90% to about 98%.

It is also noted that nasal mucociliary clearance (mcc) helps to move matter, including bacteria, away from the nasal epithelia. If secretions are not moved, then they can dry and become infected. The system and method of this invention can be used to supply moisture and mobilize such secretions. More specifically, the system and method of this invention makes it possible to introduce heated and humidified breathing gas through a nasal cannula over a prolonged period of time (e.g., overnight).

Although the apparatus and methods according to this invention have been described with reference to particular embodiments selected for illustration, and with reference to particular examples, it will be appreciated that variations and modifications to the described embodiments and examples can be made without departing from the spirit and scope of this invention. The scope is separately defined in the appended claims.

What is claimed is:

1. A tubing assembly for delivering gas to a patient from a supply unit having a port defining a gas outlet, a fluid outlet, and a fluid inlet, said tubing assembly comprising:

a tube having a gas passage to deliver gas toward a patient and a fluid passage to circulate fluid and transfer heat to gas in the gas passage;

a fitting connected to said tube, said fitting having a gas inlet oriented to provide gas flow between the gas outlet of the supply unit and said gas passage of said tube, said fitting further comprising a fluid inlet oriented to provide fluid flow between the fluid outlet of the supply unit and said fluid passage of said tube, and said fitting further comprising a fluid outlet oriented to provide fluid flow between said fluid passage of said tube and the fluid inlet of the supply unit;

said fitting of said tubing assembly being configured to provide flow communication between the gas outlet, the fluid outlet, and the fluid inlet of the supply unit and said gas passage and said fluid passage of said tube upon insertion of said fitting of said tubing assembly into the port of the supply unit;

said fluid passage of said tube comprising a fluid supply passage extending from a proximal end to a distal end of said tube and a fluid return passage extending from said distal end to said proximal end of said tube, said fluid passage being configured to circulate fluid from said proximal end to said distal end of said tube through said fluid supply passage and from said distal end to said proximal end of said tube through said fluid return passage;

said tubing assembly defining a passage for fluid flow between said fluid supply passage and said fluid return passage adjacent said distal end of said tube.

2. The tubing assembly defined in claim 1, said fitting of said tubing assembly being coupled to a proximal end of said tube.

3. The tubing assembly defined in claim 2, said tubing assembly further comprising a supply fitting coupled to a distal end of said tube.

4. The tubing assembly defined in claim 1, said gas passage of said tube of said tubing assembly extending from a proximal end to a distal end of said tube.

5. The tubing assembly defined in claim 1, said gas inlet of said fitting of said tubing assembly extending axially for flow communication with the gas outlet of the supply unit.

6. The tubing assembly defined in claim 1, said fluid outlet of said fitting of said tubing assembly being configured for longitudinal alignment with the fluid inlet of the supply unit.

7. The tubing assembly defined in claim 1, said fluid inlet of said fitting of said tubing assembly extending radially for flow communication with the fluid outlet of the supply unit.

8. The tubing assembly defined in claim 1, said fluid outlet of said fitting of said tubing assembly extending radially for flow communication with the fluid inlet of the supply unit.

9. The tubing assembly defined in claim 1, said fluid inlet and said fluid outlet of said fitting of said tubing assembly extending along a common axis oriented at an angle to the longitudinal axis of said tube.

10. A tubing assembly for delivering gas to a patient from a supply unit having a port defining a gas outlet, a fluid outlet, and a fluid inlet, said tubing assembly comprising:
a tube having a gas passage to deliver gas toward a patient and a fluid passage to circulate fluid and transfer heat to gas in the gas passage;
a fitting connected to said tube, said fitting having a gas inlet oriented to provide gas flow between the gas outlet of the supply unit and said gas passage of said tube, said fitting further comprising a fluid inlet oriented to provide fluid flow between the fluid outlet of the supply unit and said fluid passage of said tube, and said fitting further comprising a fluid outlet oriented to provide fluid flow between said fluid passage of said tube and the fluid inlet of the supply unit;
said fitting of said tubing assembly being configured to provide flow communication between the gas outlet, the fluid outlet, and the fluid inlet of the supply unit and said gas passage and said fluid passage of said tube upon insertion of said fitting of said tubing assembly into the port of the supply unit,
said fluid passage of said tube comprising a fluid supply passage extending from a proximal end to a distal end of said tube and a fluid return passage extending from said distal end to said proximal end of said tube, said fluid passage being configured to circulate fluid from said proximal end to said distal end of said tube through said fluid supply passage and from said distal end to said proximal end of said tube through said fluid return passage,
said fluid inlet of said fitting of said tubing assembly being positioned for flow communication with said fluid supply passage of said tube adjacent said proximal end of said tube.

11. The tubing assembly defined in claim 10, said fluid outlet of said fitting of said tubing assembly being positioned for flow communication with said fluid return passage of said tube adjacent said proximal end of said tube.

12. A tubing assembly for delivering gas to a patient from a supply unit having a port defining a gas outlet, a fluid outlet, and a fluid inlet, said tubing assembly comprising:
a tube having a gas passage to deliver gas toward a patient and a fluid passage to circulate fluid and transfer heat to gas in the gas passage;
a fitting connected to said tube, said fitting having a gas inlet oriented to provide gas flow between the gas outlet of the supply unit and said gas passage of said tube, said fitting further comprising a fluid inlet oriented to provide fluid flow between the fluid outlet of the supply unit and said fluid passage of said tube, and said fitting further comprising a fluid outlet oriented to provide fluid flow between said fluid passage of said tube and the fluid inlet of the supply unit;
said fitting of said tubing assembly being configured to provide flow communication between the gas outlet, the fluid outlet, and the fluid inlet of the supply unit and said gas passage and said fluid passage of said tube upon insertion of said fitting of said tubing assembly into the port of the supply unit, said fluid inlet of said fitting of said tubing assembly being configured for longitudinal alignment with the fluid outlet of the supply unit.

13. In combination:
a supply unit configured to supply gas for delivery to a patient and to supply fluid for heating the gas, said supply unit comprising a port defining a gas outlet, a fluid outlet, and a fluid inlet; and
a tubing assembly for delivering gas to a patient, said tubing assembly comprising:
a tube having a gas passage to deliver gas toward a patient and a fluid passage to circulate fluid and transfer heat to gas in the gas passage;
a fitting connected to said tube, said fitting having a gas inlet oriented to provide gas flow between the gas outlet of the supply unit and said gas passage of said tube, said fitting further comprising a fluid inlet oriented to provide fluid flow between the fluid outlet of the supply unit and said fluid passage of said tube, and said fitting further comprising a fluid outlet oriented to provide fluid flow between said fluid passage of said tube and the fluid inlet of the supply unit;
said fitting of said tubing assembly being configured to provide flow communication between the gas outlet, the fluid outlet, and the fluid inlet of the supply unit and said gas passage and said fluid passage of said tube upon insertion of said fitting of said tubing assembly into the port of the supply unit;
said fitting of said tubing assembly being releasably engaged in said port of said supply unit;
said gas outlet of said supply unit being in flow communication with said gas inlet of said fitting of said tubing assembly;
said fluid outlet of said supply unit being in flow communication with said fluid inlet of said fitting of said tubing assembly; and
said fluid inlet of said supply unit being in flow communication with said fluid outlet of said fitting of said tubing assembly.

14. The combination defined in claim 13, said fluid passage of said tube comprising a fluid supply passage extending from a proximal end to a distal end of said tube and a fluid return passage extending from said distal end to said proximal end of said tube, said fluid passage being configured to circulate fluid from said proximal end to said distal end of said tube through said fluid supply passage and from said distal end to said proximal end of said tube through said fluid return passage.

15. The combination defined in claim 13, said supply unit being configured to humidify gas and to deliver humidified gas to said gas outlet of said supply unit.

16. The combination defined in claim 13, said supply unit being configured to heat fluid and to circulate heated fluid from said fluid inlet of said supply unit to said fluid outlet of said supply unit.

17. The combination defined in claim 13, said tube having a longitudinal axis, said gas inlet of said fitting of said tubing assembly and said gas outlet of said supply unit extending along the longitudinal axis of said tube of said tubing assembly.

18. The combination defined in claim 13, said fluid inlet and said fluid outlet of said fitting of said tubing assembly extending radially outwardly.

19. The combination defined in claim 18, said fitting of said tubing assembly comprising a flange configured to engage a surface of said port for rotation of said fitting into locking engagement with said port, said fluid inlet and said fluid outlet of said fitting of said tubing assembly being in flow communication with said fluid outlet and said fluid inlet of said port, respectively, upon said rotation of said fitting into locking engagement with said port.

20. The combination defined in claim 13, said port of said supply unit comprising valves to close said fluid inlet and said fluid outlet upon removal of said fitting of said tubing assembly from said port.

21. The combination defined in claim 20, said valves of said port being configured to be opened upon insertion of said fitting of said tubing assembly into said port, thereby permitting flow communication between said fluid inlet and said fluid outlet of said port and said fluid passage of said tubing assembly.

22. The combination defined in claim 13, said supply unit further comprising a sensor mounted to detect the presence of liquid in gas delivered to said gas outlet.

23. The combination defined in claim 22, said sensor being configured to sense the intensity of a light beam generated through the gas, wherein the presence of liquid in the gas decreases the intensity of said light beam.

24. The combination defined in claim 22, said supply unit being configured to prevent the delivery of gas to said gas outlet when the presence of liquid is detected in the gas.

* * * * *